(12) United States Patent
Itami et al.

(10) Patent No.: US 7,101,551 B2
(45) Date of Patent: Sep. 5, 2006

(54) REMEDIES FOR HEPATITIS C

(75) Inventors: Seima Itami, Tokyo (JP); Tatsurou Shibui, Tokyo (JP); Makoto Seki, Tokyo (JP); Yoshihisa Yotsumoto, Tokyo (JP); Yoshiharu Matsuura, Osaka (JP); Tatsuo Miyamura, Tokyo (JP)

(73) Assignees: Mitsubishi Pharma Corporation, Osaka (JP); Japan as Represented by Director General of Agency of National Institute of Infectious Diseases, Tokyo (JP)

( * ) Notice: Subject to any disclaimer, the term of this patent is extended or adjusted under 35 U.S.C. 154(b) by 309 days.

(21) Appl. No.: 10/203,754

(22) PCT Filed: Feb. 13, 2001

(86) PCT No.: PCT/JP01/00967

§ 371 (c)(1),
(2), (4) Date: Nov. 26, 2002

(87) PCT Pub. No.: WO01/58459

PCT Pub. Date: Aug. 16, 2001

(65) Prior Publication Data

US 2003/0157132 A1 Aug. 21, 2003

(30) Foreign Application Priority Data

Feb. 14, 2000 (JP) .............................. 2000-034906

(51) Int. Cl.
*A61K 39/42* (2006.01)
*C12P 21/08* (2006.01)
*G01N 33/53* (2006.01)
*C12Q 21/08* (2006.01)
*A61K 39/12* (2006.01)
*C12P 21/04* (2006.01)

(52) U.S. Cl. .............................. 424/149.1; 424/228.1; 424/161.1; 530/388.3

(58) Field of Classification Search ............. 424/149.1, 424/228.1, 161.1; 530/388.3
See application file for complete search history.

(56) References Cited

U.S. PATENT DOCUMENTS 6,692,907 B1 * 2/2004 Weiner et al. .................. 435/5

FOREIGN PATENT DOCUMENTS

| CN | 1181929 | 5/1998 |
|----|---------|--------|
| WO | 99/18198 | 4/1999 |
| WO | 00/05266 | 2/2000 |
| WO | 00/26418 | 5/2000 |
| WO | 01/94571 | 12/2001 |

OTHER PUBLICATIONS

Pileri, P. "Binding of Hepatitis C Virus to CD81" Science (Oct. 20, 1998) vol. 282, p. 938-941.*
Schildbach, J.F. "Contribution of a single heavy chain residue to specificity of an anti-digoxin monoclonal antibody" Prot. Sci. (1994) vol. 3, 737-749.*
Winkler, K. "Changing the Antigen Binding Specificity by Single Point Mutations of an Anti-p24 (HIV-1) Antibody" J. Immun. (2000) vol. 165, No. 8, 4505-4514.*
Kessler, R.E. "Effects of Subsititution on Polyglycerol Phosphate-Specific Antibody Binding to Lipoteichoic Acids" Infec. Immun. (1983) vol. 41, No. 2, 549-555.*
Kussie, P.H. "A Single Engineered Amino Acid Substituiion Changes Antibody Fine Specificity" J. Immun. (1994) vol. 152, No. 1, 146-152; J. Immun. (2000) vol. 165, No. 8, 146-152.*
Keck, Z.Y. "Hepatitis C Virsus E2 Has Three Immunogenic Domains Containing Conformational Epitopes with Distinct Properties and Biological Functions" J. Virol. (Sep. 2004) vol. 78, No. 17 9224-9232.*
Kabat et al. "Sequence of Proteins of Immunological Interest" Fourth Edition, NIH, pp. vii-xiiv (1987).
Kabat et al. "Sequence of Proteins of Immunological Interest" Fifth Edition, NIH, pp. xii-xcvi, 103-150, and 310-338 (1991).
Yoshiharu Matsuura et al., "Characterization of Pseudotype VSV Possessing HCV Envelope Proteins", Virology, 286, pp. 263-275 (2001).
Koji Ishii et al., "Structural Analysis of Vaccina Virus Dls Strain: Application as a New Replication-Deficient Viral Vector", Virology, 302, pp. 433-444 (2002).
Chinese Office Action dated Jun. 3, 2005 (with translation).
K. Masakazu et al., "Antibody response to E2NS1 hepatitis C virus protein in patients with acute hepatitis C", Journal of Gastroenterology and Hepatology, vol. 12, No. 1, pp. 73-76 (1997).
Qui-Lim Choo et al., "Isolation of a cDNA Clone Derived from a Blood-Borne Non-A, Non-B Viral Hepatitis Genome", *SCIENCE*, vol. 244, pp. 259-362 (1989).
Nobuyuki Kato et al., "Molecular Cloning of the Human Hepatitis C Virus Genome from Japanese Patients with non-A, non-B Hepatitis", *Proc. Natl. Acad. Sci. USA*, vol. 87, pp. 9524-6528 (1990).
A. Takamizawa et al., "Structure and Organization of the Hepatitis C Virus Genome Isolated from Human Carriers", *Journal of Virology*, vol. 65, No. 3, pp. 1105-1113 (1991).
Kunihiko Hino et al., "Genotypes and Titers of Hepatitis C Virus for Predicting Response to Interferon in Patients With Chronic Hepatitis C", *Journal of Medical Virology*, vol. 42, pp. 299-305 (1994).
Takeshi Okanoue et al., "Side Effects of Interferon on Endocrine and Repiratory System in 545 Cases of Chronic Hepatitis C", *Journal of Gastroenterology*, vol. 91, pp. 995-1002 (1994).

(Continued)

*Primary Examiner*—James Housel
(74) *Attorney, Agent, or Firm*—Greenblum & Bernstein, P.L.C.

(57) ABSTRACT

The present invention provides a substance which inhibits the binding between E2/NS1 protein of hepatitis C virus and a cell infectious with hepatitis C virus, a cell expressing CD81, or CD81. The present invention can provide a novel medicament which has an anti-viral effects such as an inhibitory action against HCV infection.

5 Claims, 9 Drawing Sheets

OTHER PUBLICATIONS

Olle Reichard et al., "Ribavirin Treatment for Chronic Hepatitis C", *The LANCET*, vol. 337, pp. 1058-1061 (1991).

Nobuyuki Kato et al., "Humoral Immune Response to Hypervariable Region 1 of the Putative Envelope Glycoprotein (gp70) of Hepatitis C Virus", *Journal of Virology*, vol. 67, No. 7, pp. 3922-3930 (1991).

Nobuyuki Kato et al., "Genetic Drift in Hypervariable Region 1 of the Viral Genome in Persistent Hepatitis C Virus Infection", *Journal of Virology*, vol. 68, No. 8, pp. 4776-4784 (1994).

Koji Ishii et al., "High Titers of Antibodies Inhibiting the Binding of Envelope to Human Cells Correlate With Natural Resolution of Chronic Hepatitis C", *Hepatology*, vol. 28, pp. 1117-1120 (1998).

Piero Pileri et al., "Binding of Hepatitis C Virus to CD81", *SCIENCE*, vol. 282, pp. 938-941 (1998).

John Hopwood et al., "Anticoagulant Activity of Heparin: Isolation of Antithrombin-Binding Sites", *FEBS Letters*, vol. 69, No. 1, pp. 51-54 (1976).

Avner Yayon et al., "Cell Surface, Heparin-like Moleucles are Required for Binding of Basic Fibroblast Growth Factor to its High Affinity Receptor", *Cell*, vol. 64, pp. 841-848 (1991).

Detlef Güssow et al., "Humanization of Monoclonal Antibodies", *Methods in Enzymology*, vol. 203, pp. 99-121 (1991).

Frank Lee et al., "Glucocorticoids Regulate Expression of Dihydrofolate Reductase cDNA in Mouse Mammary Tumour Virus Chimaeric Plasmids", *Nature*, vol. 294, pp. 228-232 (1981).

*Bio Manual Series 4, Gene Introduction and Expression—Analytical Method*, pp. 28-35 (1994).

*Introductory Antibody Engineering*, Chijinshokan Co., Ltd., pp. 20-23.

Shingo Takikaw et al., "Cell Fusion Ativity of Hepatitis C Virus Envelope Protein", *Journal of Virology*, vol. 74, No. 11, pp. 5066-5074 (2000).

James D. Marks et al., "By-Passing Immunization: Human Antibodies from V-Gene Libraries Displayed on Phage", *J. Mol. Biol.*, vol. 222, pp. 581-597 (1991).

*Molecular Cloning*, pp. 1.76-1.84 (1982).

*Molecular Cloning*, pp. 6.46-6.48 (1982).

Tatsurou Shibui et al., "High-Level Production and Secretion of a Mouse-Human Chimeric Fab Fragment with Specificity to Human Carcino Embryonic Antigen in *Escherichia Coli*", *App. Microbiol Biotechnol*, vol. 38, pp. 770-775 (1993).

Yoichiro Aoki et al., "A Human Liver Cell Line Exhibits Efficient Translation of HCV RNAs Produced by a Recombinant Adenovirus Expressing T7 RNA Polymerase", *Virology*, vol. 250, pp. 140-150 (1998).

Hide Kikuchi, "Ketsueki Baikai Kansencho HCV", *Rinshou to Kenkyu*, vol. 76, No. 7, pp. 1260-1266 (1999).

Tobias Allander et al., "Recombinant Human Monoclonal Antibodies Against Different Conformational Epitopes of the E2 Envelope Glycoprotein of Hepatitis C Virus that Inhibit its Interaction with CD81", *Journal of General Virology*, vol. 81, pp. 2451-2459 (2000).

Mike Flint et al., "Functional Analysis of Cell Surface-Expressed Hepatitis C Virus E2 Glycoprotein", *Journal of Virology*, vol. 73, No. 8, pp. 6782-6790 (1999).

Mike Flint et al., "Functional Characterization of Intracellular and Secreted Forms of a Truncated Hepatitis C Virus E2 Glycoprotein", *Journal of Virology*, vol. 74, No. 2, pp. 702-709 (2000).

* cited by examiner

REMEDIES FOR HEPATITIS C

TECHNICAL FIELD

The present invention relates to various substances which bind to an envelope glycoprotein of hepatitis C virus (hereinafter sometimes referred to as "HCV"), and more particularly to proteins such as antibodies, sulfated polysaccharides and low molecular weight compounds, which have anti-viral effects such as inhibitory actions against HCV infection by binding to the envelope glycoprotein of HCV.

BACKGROUND ART

In 1989, Chiron Corporation (U.S.A.) cloned a gene fragment of human hepatitis virus which had been heretofore referred to as "non-A non-B hepatitis virus," and the fragment was named "HCV" (SCIENCE, Vol. 244, 359–362, 1989). HCV is a virus, the genome of which is single strand (+) strand RNA. Besides Chiron Corporation, Shimotohno et al. of the National Cancer Center (Proc. Natl. Acad. Sci. USA, Vol. 87, 9524–9528, 1990) and Takamizawa et al. of the Research Institute for Microbial Diseases at Osaka University (J. Virol, Vol. 65, No. 3, 1105–1113, 1990) thereafter published the entire gene sequences of hepatitis C virus. Thereafter, it was found that HCV comprise three types of structural proteins, i.e., core protein, envelope 1 protein (hereinafter sometimes referred to as "E1" or "E1 protein") and envelope 2 protein (hereinafter sometimes referred to as "E2/NS1" or "E2/NS1 protein") and 6 types of non-structural proteins.

Once HCV is developed, acute hepatitis, chronic hepatitis, and hepatocirrhosis are highly likely to be developed, and the disease condition is eventually transited to liver cancer leading a patient to death. Conventionally, interferon, an anti-viral agent, has been typically used in the treatment. However, there are problems of variation in the therapeutic effects for each patient and side effects such as fever (J. Med. Virol., Vol. 42, 299–305, 1994) (Journal of Gastroenterology, Vol. 91, 995–1002, 1994).

Although a treatment using other anti-viral agents such as ribavirin has been also studied, this could not provide sufficient effect (Lancet, Vol. 337, 1058–1061, 1991), and therefore the development of a novel anti-HCV agent has been awaited.

HCV gene is considered to very easily undergo mutation and HCV, because of its high mutation ability, was presumed to escape from the immunity in the body of a patient. In particular, at the N-terminus of E2/NS1 of HCV, there is presumed to be a region of 25 to 30 amino acids, referred to as a "hyper variable region," which is rich in mutation, and Kato et al. deduce that an epitope of a human immune system is a hyper variable region (J. Virol., Vol. 67, No. 7, 3923–3930, 1993) (J. Virol., Vol. 68, No. 8, 4776–4784, 1994). More specifically, since the region which is recognized by the human immune system such as neutralizing antibody is in the hyper variable region, even though the neutralizing antibody is generated in the body of the infected patient, it is considered that the hyper variable region immediately undergoes mutation and viruses escape from the antibody. However, Ishii et al. have reported that an antibody which inhibits the binding between E2/NS1 and human T cell Molt-4 is present in a highly active state only in the blood of a patient who naturally recovered from HCV, and it is suggested that a humoral immunity is involved in the treatment of HCV in spite of the high mutation ability of HCV (Hepatology, Vol. 28, No. 4, 1117–1120, 1998).

In 1999, Chiron Corporation (U.S.A.) isolated CD81 as a protein on a cell surface to which E2/NS1 bound (SCIENCE, Vol. 282, 938–941, 1999). CD81 and E2/NS1 which were expressed in *Escherichia coli*, bound to each other in the same manner as reported by Ishii et al. and the serum of a patient who naturally recovered from HCV inhibited this binding. This result suggested that CD81 was a receptor of HCV.

From the foregoing, it has been considered that the use, as an agent, of a substance such as an antibody, which binds to an envelope protein that is presumably deeply involved in the infection of HCV to a cell and inhibits the binding to a human cell infectious with HCV, can inhibit HCV in the blood from infecting organs capable of being infected such as liver again, and can lead the HCV patient to the recovery. However, as yet, infection-inhibiting substances for HCV-derived diseases have not been sufficiently studied.

DISCLOSURE OF THE INVENTION

HCV is known to be RNA virus and, thus, is highly likely to undergo mutation. This mutation causes mutation in many sites, both in the structural protein and the non-structural protein of HCV. Because of this mutation, the development of a substance for inhibiting HCV infection, for example, an antibody which recognizes a given protein sequence, has been considered to be difficult. However, the present inventors have focused on the point that the neutralizing antibody reported by Ishii et al. inhibits the binding to only one type of E2/NS1 even though the sequence of the infected virus are different for each recovered patient. More specifically, they have considered that a substance recognizing a specific region or a configuration of the antigen can inhibit the binding between E2/NS1 and a human cell infectious with HCV, a CD81 expressing cell, or CD81 and prevent infection regardless of the diversity of viral sequences.

In the present invention, for the purpose of developing an agent for improving the symptoms of hepatitis C patients, the present inventors have conducted concentrated search on substances which inhibit the binding between E2/NS1 and the cell infectious with HCV, the cell expressing CD81, or CD81, and as a result, succeeded in obtaining a substance capable of inhibiting the binding and infection of HCV to a cell infectious with HCV.

Thus, the present invention provides a substance which inhibits the binding between E2/NS1 protein of hepatitis C virus and a cell infectious with hepatitis C virus, a cell expressing CD81, or CD81.

The preferred embodiment of the present invention provides: a substance which inhibits, upon binding to a region having a positively charged regions of E2/NS1 protein of hepatitis C virus, the binding between E2/NS1 protein of hepatitis C virus and a cell infectious with hepatitis C virus, a cell expressing CD81, or CD81; a substance in which E2/NS1 protein of hepatitis C virus is a protein prepared by adding a substance capable of recognizing E2/NS1 protein to E2/NS1 protein of hepatitis C virus; a substance in which E2/NS1 protein of hepatitis C virus is a protein prepared by adding a substance capable of detecting E2/NS1 protein by a fluorescence method or a luminescence method to E2/NS1 protein of hepatitis C virus; a substance in which E2/NS1 protein of hepatitis C virus is a protein prepared by adding a tag to E2/NS1 protein of hepatitis C virus; a substance in which E2/NS1 protein of hepatitis C virus is a protein prepared by adding a tag to the C-terminus of E2/NS1 protein of hepatitis C virus; a substance in which a cell expressing CD81 is a cell which expresses human CD81; a substance in which CD81 is human CD81 and expressed by solubilized form; a substance which has an association constant to E2/NS1 protein of hepatitis C virus is higher than $10^8$, or a dissociation constant to E2/NS1 protein of hepatitis C virus is lower than $10^{-8}$; a substance which has an association constant to E2/NS1 protein of hepatitis C virus is higher than $10^9$, or a dissociation constant tQ E2/NS1 protein of hepatitis C virus is lower than $10^{-9}$; a substance which is a protein, sulfated polysaccharide, or a low molecular weight compound; a substance in which a protein is an antibody; a substance in which an antibody is derived from the B cell of a patient who recovered from hepatitis C; a substance in which an antibody is derived from genes in the B cell of a patient who recovered from hepatitis C; and a substance in which a patient is recovered from hepatitis C without any antiviral treatment and the B cell is peripheral blood mononuclear cell.

Another aspect of the present invention provides:

an antibody in which CDR-1, CDR-2, and CDR-3 of a variable region of the H chain respectively comprise amino acid sequences shown by SEQ ID NOS: 1, 2, and 3 in the Sequence Listing or the amino acid sequences having a deletion, a substitution, or an addition of one or several amino acids in the amino acid sequences shown by SEQ ID NOS: 1, 2, and 3, and which has an affinity to E2/NS1 protein of hepatitis C virus;

said antibody which comprises an amino acid sequence shown by SEQ ID NO: 16 or 34 in the Sequence Listing or the amino acid sequence having a deletion, a substitution, or an addition of one or several amino acids in the amino acid sequence shown by SEQ ID NO: 16 or 34;

an antibody in which CDR-1, CDR-2, and CDR-3 of a variable region of the L chain respectively comprise amino acid sequences shown by SEQ ID NOS: 4, 5, and 6 in the Sequence Listing or the amino acid sequences having a deletion, a substitution, or an addition of one or several amino acids in the amino acid sequences shown by SEQ ID NOS: 4, 5, and 6, and which has an affinity to E2/NS1 protein of hepatitis C virus;

said antibody which comprises an amino acid sequence shown by SEQ ID NO: 17 in the Sequence Listing or the amino acid sequence having a deletion, a substitution, or an addition of one or several amino acids in the amino acid sequence shown by SEQ ID NO: 17;

an antibody in which CDR-1, CDR-2, and CDR-3 of a variable region of the L chain respectively comprise amino acid sequences shown by SEQ ID NOS: 7, 8, and 9 in the Sequence Listing or the amino acid sequences having a deletion, a substitution, or an addition of one or several amino acids in the amino acid sequences shown by SEQ ID NOS: 7, 8, and 9, and which has an affinity to E2/NS1 protein of hepatitis C virus;

said antibody which comprises an amino acid sequence shown by SEQ ID NO: 18 in the Sequence Listing or the amino acid sequence having a deletion, a substitution, or an addition of one or several amino acids in the amino acid sequence shown by SEQ ID NO: 18;

an antibody in which CDR-1, CDR-2, and CDR-3 of a variable region of the L chain respectively comprise amino acid sequences shown by SEQ ID NOS: 10, 11, and 12 in the Sequence Listing or the amino acid sequences having a deletion, a substitution, or an addition of one or several amino acids in the amino acid sequences shown by SEQ ID NOS: 10, 11, and 12, and which has an affinity to E2/NS1 protein of hepatitis C virus;

said antibody which comprises an amino acid sequence shown by SEQ ID NO: 19 in the Sequence Listing or the amino acid sequence having a deletion, a substitution, or an addition of one or several amino acids in the amino acid sequence shown by SEQ ID NO: 19;

an antibody in which CDR-1, CDR-2, and CDR-3 of a variable region of the L chain respectively comprise amino acid sequences shown by SEQ ID NOS: 13, 14, and 15 in the Sequence Listing or the amino acid sequences having a deletion, a substitution, or an addition of one or several amino acids in the amino acid sequences shown by SEQ ID NOS: 13, 14, and 15, and which has an affinity to E2/NS1 protein of hepatitis C virus; and said antibody which comprises an amino acid sequence shown by SEQ ID NO: 20 in the Sequence Listing or the amino acid sequence having a deletion, a substitution, or an addition of one or several amino acids in the amino acid sequence shown by SEQ ID NO: 20;

A further aspect of the present invention provides:

an antibody in which CDR-1, CDR-2, and CDR-3 of a variable region of the L chain respectively comprise amino acid sequences shown by SEQ ID NOS: 42, 43, and 44 in the Sequence Listing or the amino acid sequences having a deletion, a substitution, or an addition of one or several amino acids in the amino acid sequences shown by SEQ ID NOS: 42, 43, and 44, and which has an affinity to E2/NS1 protein of hepatitis C virus;

said antibody which comprises an amino acid sequence shown by SEQ ID NO: 54 in the Sequence Listing or the amino acid sequence having a deletion, a substitution, or an addition of one or several amino acids in the amino acid sequence shown by SEQ ID NO: 54;

an antibody in which CDR-1, CDR-2, and CDR-3 of a variable region of the L chain respectively comprise amino acid sequences shown by SEQ ID NOS: 45, 46, and 47 in the Sequence Listing or the amino acid sequences having a deletion, a substitution, or an addition of one or several amino acids in the amino acid sequences shown by SEQ ID NOS: 45, 46, and 47, and which has an affinity to E2/NS1 protein of hepatitis C virus;

said antibody which comprises an amino acid sequence shown by SEQ ID NO: 55 in the Sequence Listing or the amino acid sequence having a deletion, a substitution, or an addition of one or several amino acids in the amino acid sequence shown by SEQ ID NO: 55;

an antibody in which CDR-1, CDR-2, and CDR-3 of a variable region of the L chain respectively comprise amino acid sequences shown by SEQ ID NOS: 48, 49, and 50 in the Sequence Listing or the amino acid sequences having a deletion, a substitution, or an addition of one or several amino acids in the amino acid sequences shown by SEQ ID NOS: 48, 49, and 50, and which has an affinity to E2/NS1 protein of hepatitis C virus;

said antibody which comprises an amino acid sequence shown by SEQ ID NO: 56 in the Sequence Listing or the amino acid sequence having a deletion, a substitution, or an addition of one or several amino acids in the amino acid sequence shown by SEQ ID NO: 56;

an antibody in which CDR-1, CDR-2, and CDR-3 of a variable region of the L chain respectively comprise amino acid sequences shown by SEQ ID NOS: 51, 52, and 53 in the Sequence Listing or the amino acid sequences having a deletion, a substitution, or an addition of one or several amino acids in the amino acid sequences shown by SEQ ID NOS: 51, 52, and 53, and which has an affinity to E2/NS1 protein of hepatitis C virus; and said antibody which comprises an amino acid sequence shown by SEQ ID NO: 57 in the Sequence Listing or the amino acid sequence having a deletion, a substitution, or an addition of one or several amino acids in the amino acid sequence shown by SEQ ID NO: 57 ;

A further aspect of the present invention provides:

an antibody which comprises, as an amino acid sequence of a heavy chain, an amino acid sequences shown by SEQ ID NO: 40 in the Sequence Listing or the amino acid sequences having a deletion, a substitution, or an addition of one or several amino acids in the amino acid sequences shown by SEQ ID NO: 40, and which has an affinity to E2/NS1 protein of hepatitis C virus; and an antibody which comprises, as an amino acid sequence of a light chain, an amino acid sequences shown by SEQ ID NO: 41 in the Sequence Listing or the amino acid sequences having a deletion, a substitution, or an addition of one or several amino acids in the amino acid sequences shown by SEQ ID NO: 41, and which has an affinity to E2/NS1 protein of hepatitis C virus;

A further aspect of the present invention provides a single-chain antibody having an affinity to E2/NS1 protein of hepatitis C virus, which comprises an amino acid sequence shown by SEQ ID NO: 26, 27, 28, or 29 in the Sequence Listing or the amino acid sequence having a deletion, a substitution, or an addition of one or several amino acids in the amino acid sequence shown by SEQ ID NO: 26, 27, 28, or 29.

A further aspect of the present invention provides a single-chain antibody having an affinity to E2/NS1 protein of hepatitis C virus, which comprises an amino acid sequence shown by SEQ ID NO: 36, 37, 38, or 39 in the Sequence Listing or the amino acid sequence having a deletion, a substitution, or an addition of one or several amino acids in the amino acid sequence shown by SEQ ID NO: 36, 37, 38, or 39.

A further aspect of the present invention provides a single-chain antibody having an affinity to E2/NS1 protein of hepatitis C virus, which comprises an amino acid sequence shown by SEQ ID NO: 62, 63, 64, or 65 in the Sequence Listing or the amino acid sequence having a deletion, a substitution, or an addition of one or several amino acids in the amino acid sequence shown by SEQ ID NO: 62, 63, 64, or 65.

A further aspect of the present invention provides a nucleic acid which encodes the aforementioned antibody of the present invention. Preferably, there is provided: the nucleic acid which comprises a nucleotide sequence shown by any of SEQ ID NO: 21, 22, 23, 24, 25, 35, 58, 59, 60, or 61 in the Sequence Listing; the nucleic acid which comprises a nucleotide sequence shown by SEQ ID NO: 40 or 41 in the Sequence Listing; the nucleic acid which comprises a nucleotide sequence shown by any of SEQ ID NO: 26, 27, 28, or 29 in the Sequence Listing; the nucleic acid which comprises a nucleotide sequence shown by any of SEQ ID NO: 36, 37, 38, or 39 in the Sequence Listing; and the nucleic acid which comprises a nucleotide sequence shown by any of SEQ ID NO: 62, 63, 64, or 65 in the Sequence Listing.

A still further aspect of the present invention provides a method for producing an antibody using any of the above-described nucleic acids.

A further aspect of the present invention provides a recombinant antibody which can be obtained by the above method and has an affinity to E2/NS1 protein of hepatitis C virus. Preferably, a recombinant antibody in which the Fc region is of a human type, and a recombinant antibody which is a single-strand antibody, are provided.

A further aspect of the present invention provides: a medicament which comprises the aforementioned substance of the present invention as an active ingredient; a medicament which comprises the aforementioned antibody of the present invention as an active ingredient; and a medicament which comprises the aforementioned recombinant antibody of the present invention as an active ingredient. Preferably, there are provided a medicament for treating and/or preventing hepatitis C and a medicament for diagnosing hepatitis C. Further, the present invention provides an anti-HCV agent which comprises the aforementioned substance of the present invention as an active ingredient, an anti-HCV agent which comprises the aforementioned antibody of the present invention as an active ingredient, and an anti-HCV agent which comprises the recombinant antibody of the present invention as an active ingredient.

A further aspect of the present invention provides a method for obtaining a sequence of the variable region of the antibody binding to E2/NS1 in which the B cell of a patient who recovered from hepatitis C is stimulated to express mRNA of the antibody against E2/NS1 protein of hepatitis C virus, and thereby mRNA of the antibody and cDNA of the antibody are obtained from the B cell. Preferably, a method for obtaining a sequence of the variable region of the antibody is provided in which a patient who recovered from hepatitis C is one who recovered without antiviral treatment and the B cell is a peripheral blood mononuclear cell.

A further aspect of the present invention provides an antibody having a sequence of the variable region obtained by the above-described method.

A further aspect of the present invention provides a method for screening a substance which inhibits the binding between E2/NS1 of hepatitis C virus and a cell infectious with hepatitis C, a cell expressing CD81, or CD81, which comprises steps of: contacting E2/NS1 of hepatitis C virus with a cell infectious with hepatitis C, a cell expressing CD81, or CD81 in the presence and absence of a test substance; and comparing the bindings between E2/NS1 of hepatitis C virus and the cell infectious with hepatitis C, the cell expressing CD81, or CD81 in the presence and absence of a test substance. Preferably, there are provided: a screening method in which E2/NS1 protein of hepatitis C virus is a protein prepared by adding a substance capable of recognizing E2/NS1 protein to E2/NS1 protein of hepatitis C virus; a screening method in which E2/NS1 protein of hepatitis C virus is a protein prepared by adding a substance capable of detecting E2/NS1 protein by a fluorescence method or a luminescence method to E2/NS1 protein of hepatitis C virus; a screening method in which E2/NS1 protein of hepatitis C virus is a protein prepared by adding a tag to E2/NS1 protein of hepatitis C virus; a screening method in which E2/NS1 protein of hepatitis C virus is a protein prepared by adding a tag to the C-terminus of E2/NS1 protein of hepatitis C virus; a screening method in which the cell expressing CD81 is a cell which expresses human CD81; a screening method in which CD81 is human CD81 and expressed by solubilized form; and a screening method in which the test substance is a protein, sulfated polysaccharides, or a low molecular weight compound.

A still further aspect of the present invention provides a substance which inhibits the binding between E2/NS1 protein of hepatitis C virus and the cell infectious with hepatitis C, the cell expressing CD81, or CD81, which is obtained by any of the above screening methods.

A further aspect of the present invention provides a substance which inhibits a life cycle of hepatitis C virus, which is obtained by the screening method which comprises steps of assaying the binding between a cell infectious with HCV and a cell expressing HCV protein in the presence and absence of the test substance, and comparing it with the binding in the absence of the test substance; and a substance which inhibits a life cycle of hepatitis C virus, which is obtained by the screening method which comprises steps of, after the cell infectious with HCV has bound with the HCV protein expressing cell in the presence or absence of the test substance, assaying the fusion between the cell infectious with HCV and the HCV protein expressing cell, and comparing it with the fusion in the absence of the test substance. Preferably, the test substance is a protein, sulfated polysaccharides, or a low molecular weight compound.

A further aspect of the present invention provides: an anti-HCV agent which comprises the above substance as an active ingredient, and a method for producing the anti-HCV agent which comprises formulating the anti-HCV agent using the above substance. The method for production preferably comprises a step of confirming the inhibition of proliferation of hepatitis C virus by the above screening method.

BEST MODE FOR CARRYING OUT THE INVENTION

Figure 1:
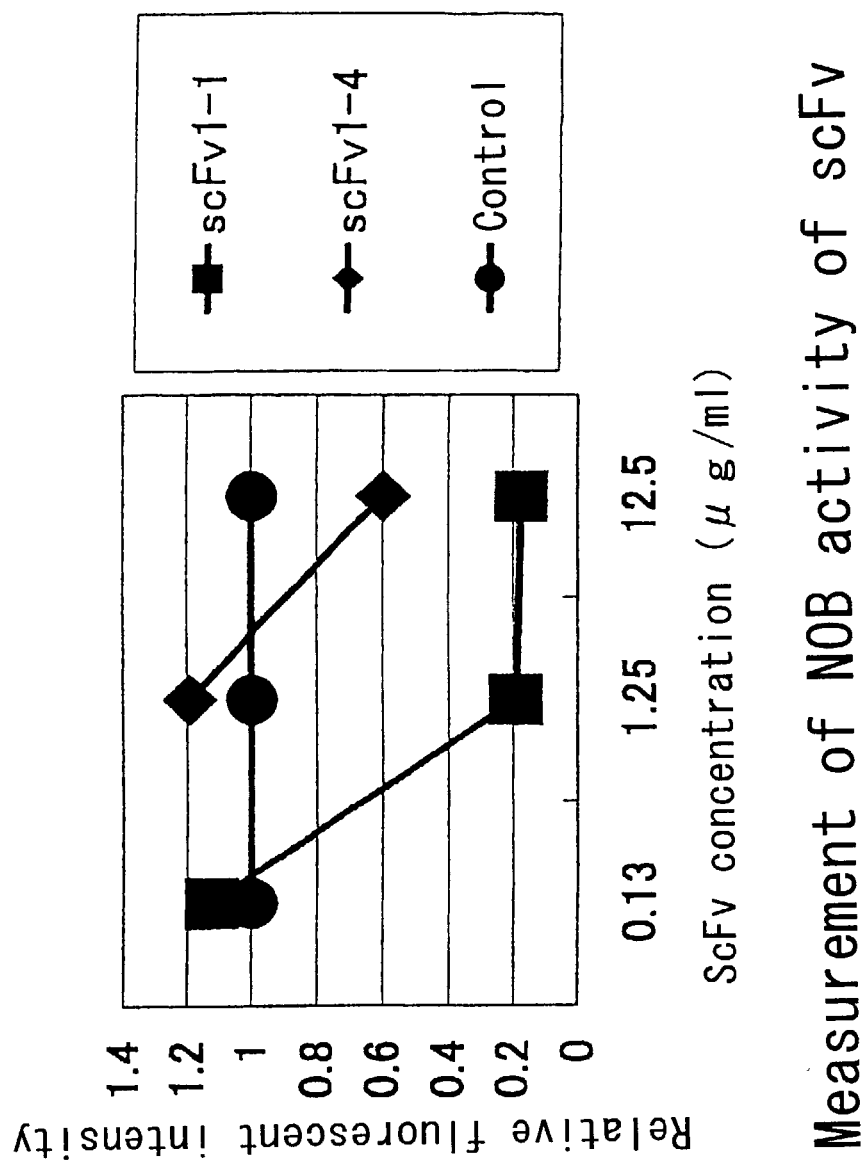
FIG. 1 is a diagram showing neutralizing activities of antibodies scFv1-1 and scFv1-4 according to the present invention.

The present invention is described in more detail below.

The substance according to the present invention is a substance which inhibits the binding between E2/NS1 protein of hepatitis C virus and a cell infectious with hepatitis C virus (hereinafter sometimes referred to as "HCV infectious cell"), a cell expressing CD81 (hereinafter sometimes referred to as "CD81 expressing cell"), or CD81.

A method for selecting such substances as described above and confirming whether or not each of these substances can inhibit the binding between E2/NS1 and the HCV infectious cell, the CD81 expressing cell, or CD81, is described below.

As described above, an HCV envelope protein comprises E1 and E2/NS1. A region in E2/NS1 which is rich in mutation, referred to as a "hyper variable region," is deduced to be an epitope of a human immune system. More specifically, E2/NS1 is deduced to be deeply involved in the binding to a cell, which is the first stage of viral infection. Therefore, in the present invention, a substance which inhibits the binding between E2/NS1 and the HCV infectious cell, the CD81 expressing cell, or CD81 has been developed as an inhibitor of binding of HCV to a cell or HCV infection.

E2/NS1 comprises the amino acids 384 to 746 in the protein expressed from the HCV genome. In the present invention, the binding of E2/NS1 to the HCV infectious cell was confirmed, for example, by expressing a protein prepared by adding a tag to the C-terminus of E2/NS1 of HCV genes in a solubilized state, binding it to the HCV infectious cell or the CD81 expressing cell, and confirming the binding of E2/NS1 to the above cell by a light-emission method or a luminescence method using an antibody against the tag. A substance which inhibits the binding was confirmed by mixing E2/NS1 with a substance for which the binding inhibition was to be confirmed before binding a solubilized E2/NS1 with the above cell in a system for confirming the binding, followed by the assay of changes in light emission or color development by mixing with the cells. Substances which inhibits the binding are described below in detail, and examples include an antibody which comprises amino acid sequences shown by SEQ ID NOS: 1 to 3 in the H chain and amino acid sequences shown by SEQ ID NOS: 4 to 6 in the L chain, heparin, and suramin. A substance is not limited to these as long as the substance inhibits the binding between E2/NS1 and the HCV infectious cell or the CD81 expressing cell. Since the binding between solubilized CD81 and E2 has also been reported (SCIENCE, Vol. 282, 938–941), it is easily deduced that the binding between solubilized CD81 and E2 can be inhibited by using the above substance.

Sulfated polysaccharides such as heparin are known to be of strong negative charge and are known to bind to a region having a strong positive charge in proteins such as antithrombin III and a fibroblast growth factor (FEBS Lett, Vol. 69, 51–54, 1976) (Cell, Vol. 64, 841–848, 1991). Further, as described in Examples below, in the present invention it was found that E2/NS1 bound to heparin. That is, among the substances described in Examples, because heparin couples to a region in E2/NS1 with a strong positive charge, it is easily deduced that it inhibits the binding between E2/NS1 and the HCV infectious cell, the CD81 expressing cell, or CD81. Any substance which binds to the region having a positive charge in E2/NS1 can inhibit the binding between E2/NS1 and the HCV infectious cell, the CD81 expressing cell, or CD81.

Since sulfated polysaccharides such as heparin could affect the charge on the surface of the protein and impart a structural change upon binding to a glycoprotein, the binding between sulfated polysaccharides and E2/NS1 was confirmed in the present invention. A structural change as described above is deduced to be involved in the binding between E2/NS1 and the HCV infectious cell, the CD81 expressing cell, or CD81.

"Negative charge" and "positive charge" used herein refer to charged sites which are present on the protein or the sugar chain bound thereto. In the present invention, the site is a domain in which E2/NS1 binds to Heparin sepharose CL-6B (Pharmacia) and binds to a column when it is not eluted by 10 mM phosphate buffer containing 0.15 M NaCl.

According to the present invention, "a substance which can recognize E2/NS1 protein of hepatitis C virus" refers to a tagged protein as described below and a substance capable of detecting E2/NS1 protein by an antibody such as hapten.

"A protein prepared by adding a tag to E2/NS1 protein of hepatitis C virus" used herein is not particularly limited, as long as the protein is prepared by adding a sequence which can be recognized by a specific antibody and has at least 5 amino acids such as known Etag (Pharmacia), Histag, myctag, FLAGtag, HAtag, GST and IgG Fc regions to for example the C-terminus of a protein of the amino acids 384 to 711 on the HCV genome. As described above, an epitope of an immune system, referred to as a "hyper variable region," is considered to be present at the N-terminus of E2/NS1 of HCV. Accordingly, when E2/NS1 is expressed after binding a tag thereto, use of those having a tag bound to the C-terminus is preferred. Proteins thus obtained are soluble. This soluble E2/NS1 can be used without particular limitation as long as the outermembrane domain of E2/NS1 between the amino acid 384 and the amino acid 746 is expressed. A tagged and solubilized E2/NS1 protein can be expressed in cells capable of adding a sugar chain to proteins, such as animal cells, insect cells, and yeast.

The protein prepared by adding a substance detectable by antibodies such as hapten to E2/NS1 protein of hepatitis C virus refers to a substance prepared by expressing an outermembrane domain of E2/NS1 between the amino acid 384 and the amino acid 746 of E2/NS1, and binding it with a low molecular weight compound which can be recognized by antibodies, such as biotin, fluorescein or DIG. Regarding the substances which recognize a low molecular weight compound, in the case of the exemplified biotin, for example, the substance can be recognized by proteins such as avidin and streptoavidin in addition to antibodies. Therefore, it is not particularly limited to an antibody and a protein, as long as it is capable of recognizing the substance.

The protein prepared by adding a substance detectable by a fluorescent method or a luminescence method to E2/NS1 protein of hepatitis C virus, refers to, for example, a substance prepared by expressing an outermembrane domain of E2/NS1 between the amino acid 384 and the amino acid 746 of E2/NS1, and binding it with a fluorescence-emitting substance or a substance prepared by binding the substance to certain substance, for example, a substance which develops a color upon mixing with an enzyme substrate, such as FITC, alkali phosphatase or HRP.

In the present invention, "HCV infectious cell" refers to human hepatic cells such as Huh7, HepG2, and WRL68 and lymphocyte cells such as Molt-4, MT-2, and Daudi as cells in which HCV could proliferate or infect. The cells are not limited to these as long as the cell shows the HCV infectivity.

Examples of cells expressing CD81 include those prepared by introducing a vector which is obtained by inserting human CD81 genes (GenBank Registration No. M33680) into a multicloning site of pCDNA3.1(+) (Invitrogen), in the NIH3T3 cell using Lipofectin (GIBCO BRL). In the present invention, a vector for expressing CD81, an expression cell, and a method for introducing a gene are not particularly limited, as long as the human CD81 expression can be confirmed in the cell constructed by a conventional gene recombination technique by means of a method for detecting protein or mRNA such as Western blotting, a fluorescence detection method using an anti-CD81 antibody or Northern blotting.

When a substance which inhibits the binding between E2/NS1 and CD81 is selected in the present invention, CD81 used herein can be a solubilized human CD81. Any solubilized human CD81 can be used without particular limitation so far as the outermembrane domain of CD81 is expressed. The solubilized CD81 can be expressed in accordance with a conventional gene recombination technique using animal cells, insect cells, yeast, *Escherichia coli,* and the like. Further, it is not necessary that the solubilized CD81 is one obtained by expressing only the outermembrane domain. For example, a tagged one or a modified one can be used without any problem for the purpose of purification or detection.

Examples of the light emission method and the luminescence method mentioned in the method for detecting the binding between E2/NS1 and the HCV infectious cell, the CD81 expressing cell, or CD81 using an antibody against a tag preferably include flow cytometry, cell ELISA, and ELISA. The methods are not particularly limited so far as the binding between E2/NS1 and the CD81 expressing cell or CD81 can be detected.

The "antibody" used herein includes, in addition to an antibody normally existing in a living organism, a peptide comprising at least one antigen binding site formed by the variable region in the H chain or L chain of the antibody or a combination thereof, Fab composed of a set of H chain fragment and L chain fragment, F(ab')2 composed of two sets of H chain fragments and L chain fragments, and a single-chain antibody composed of H chain fragment and L chain fragment bound in series to the same peptide (hereinafter sometimes referred to as "scFv"). In the present invention, the whole antibody is most preferred.

In the present invention, a monoclonal antibody was prepared by obtaining a gene of an antibody from the B-cell of a patient who recovered from hepatitis C. Conventional methods for isolating only the genes of antibody of interest from a plurality of B-cells derived from human include a method in which EBV is transformed into the B-cell of a patient to immortalize the B cell, followed by the cloning of only the cells which produce the antibody of interest. As a result of concentrated studies, the present inventors have succeeded in obtaining scFv by the phage display method.

For example, an antibody was obtained by the phage display method by sampling heparin blood from a patient who recovered from hepatitis C, obtaining peripheral blood mononuclear cells by the Ficoll method, and purifying the B-cells only using an anti-CD19 antibody support. Thereafter, human IL-2, human IL-10, E2/NS1 antigen(1 ng/ml), and anti-human CD40 antibody (1 μg/ml) were used to stimulate the B-cell for the transcription of genes of antibody to mRNA. The purification of B-cell is not particularly limited as long as the B-cells can be specifically separated. The stimulation of B-cell can be carried out in a manner different from the above method and can be carried out in an appropriately abbreviated manner without problem. Thereafter, antibody mRNA and antibody cDNA were obtained from the B-cell. Further, a frame of a gene of a single chain antibody was prepared which was capable of incorporating genes in the H chain and the L chain variable regions into scFv expression plasmid, and gene 3 gene of M13 phage was ligated to the downstream thereof. An H chain and an L chain randomly obtained from the cDNA by PCR were incorporated into the sites into which the variable regions of the H chain and the L chain were to be incorporated. Using this plasmid, a single chain antibody which was incorporated in the form of fused protein with gene 3 protein at the end of M13 phage was expressed, and only those bound to E2/NS1 were selected therefrom. Thus, a single chain antibody scFv1-1 and a phage expressing the scFv1-1 in which CDR-1, CDR-2, and CDR-3 of the variable region of the H chain were, respectively, the amino acid sequences shown by SEQ ID NOS: 1, 2, and 3 in the Sequence Listing and CDR-1, CDR-2, and CDR-3 in the variable region of the L chain were, respectively, the amino acid sequences shown by SEQ ID NOS: 4, 5, and 6 in the Sequence Listing, were obtained. It was found that scFv1-1 and a phage expressing the scFv1-1 had a particularly strong affinity to E2/NS1 and strongly inhibited the binding between E2/NS1 and the HCV infectious cell, the CD81 expressing cell, or CD81.

The method for screening a single-chain antibody using the M13 phage system was described above. In the present invention, any method can be used without particular limitation so far as the "antibody" and the protein expressed on the surface of the phage can be expressed in the form of a fusion protein.

In the present invention, "a patient who recovered from hepatitis C" refers to a patient whose mRNA of HCV in the blood became lower than the lower limit of the detection limit and for whom a measured value of liver function such as the ALT value, has been in a normalized state for 6 months or longer after having been in what is called a "hepatitis C condition" with mRNA of HCV being detected in the blood and abnormality observed in a value for measuring the liver function such as ALT.

scFv1-1, which was exemplified as a representative example of the antibody according to the present invention, showed the binding constant Ka to E2/NS1 of $4.5 \times 10^8$ (M) and the dissociation constant Kd of $2.2 \times 10^{-9}$ (1/M) as a result of measurement using BIACORE (BIACORE). The present inventors obtained a plurality of single chain antibodies having the same variable region of the H chain as that of scFv1-1 and a variable region of the L chain that was different from that of scFv1-1, and for each single chain antibody the binding ability and the ability of inhibiting the binding between E2/NS1 and the HCV infectious cell and the human CD81 expressing cell were compared. As a result, there was a correlation between the binding ability and the ability of inhibiting the binding between E2/NS1 and cells. Among those, a single-chain antibody scFv1-1 having a binding constant of $10^8$(M) or more and a dissociation constant of $10^{-8}$(1/M) or less can be judged as being satisfactory as a medicament from the viewpoint of the inhibitory activity. That is, an antibody having a binding constant to E2/NS1 of $10^8$(M) or more and a dissociation constant of $10^{-8}$(1/M) or less as a result of measurement using BIACORE is more preferred as a medicament for inhibiting infection to the HCV infectious cell. In order to further enhance the ability of the antibody, an antibody having a binding constant of $10^9$(M) or more and a dissociation constant of $10^{-9}$(1/M) or less is further preferred.

In general, an antibody comprises two types of polypeptides, i.e., a large polypeptide and a small polypeptide, and a larger subunit is referred to as an "H chain" and a smaller subunit is referred to as an "L chain." The peptides respectively comprise a "variable region" which is present at the N-terminal side and forms an antigen binding site and a "constant region" which is defined by each antibody class. The variable region is further divided into complementarity-determining regions "CDRs" which are deeply involved in the formation of the antigen binding site and "frameworks" which are present therebetween. A CDR is known to have three regions, "CDR-1," "CDR-2," and "CDR-3" from the N-terminal side for each of the H chain and the L chain.

The antibodies ScFv1-1, ScFv1-2, ScFv1-3, and ScFv1-4 of the present invention are described below as examples. The amino acid sequences of the antibodies ScFv1-1, ScFv1-2, ScFv1-3, and ScFv1-4 are shown in SEQ ID NOS: 1 to 20 in the Sequence Listing, and the DNA sequences are shown in SEQ ID NOS: 21 to 25.

The amino acids which constitute a variable region of the antibody often vary depending on the antibody. The amino acid sequence in the H chain portion of ScFv1-1 is shown in SEQ ID NO: 16. SEQ ID NO: 16 represents a sequence for expressing scFv in *Escherichia coli*, i.e., a sequence having 2 amino acids added to the N terminus of the H chain of scFv1-1. Accordingly, considered in terms of an antibody framework, the amino acids 3 to 32 in SEQ ID NO: 16 represent framework 1, the amino acids 33 to 37 represent "CDR-1," the amino acids 38 to 51 represent framework 2, the amino acids 52 to 68 represent "CDR-2," the amino acids 69 to 100 represent framework 3, the amino acids 101 to 117 represent "CDR-3," and the amino acids 118 to 128 represent framework 4. The amino acid sequence in the L chain portion of ScFv1-1 is shown in SEQ ID NO: 17. The amino acids 1 to 23 in SEQ ID NO: 17 represent framework 1, the amino acids 24 to 34 represent "CDR-1," the amino acids 35 to 49 represent framework 2, the amino acids 50 to 56 represent "CDR-2," the amino acids 57 to 88 represent framework 3, the amino acids 89 to 97 represent "CDR-3," and the amino acids 98 to 111 represent framework 4. The amino acid sequences of the H chain of ScFv1-2, 1-3, and 1-4 are all shown in SEQ ID NO: 16. The L chain is as described below. The amino acid sequence in the L chain portion of ScFv1-2 is shown in SEQ ID NO: 18. The amino acids 1 to 23 in SEQ ID NO: 18 represent framework 1, the amino acids 24 to 34 represent "CDR-1," the amino acids 35 to 49 represent framework 2, the amino acids 50 to 56 represent "CDR-2," the amino acids 57 to 88 represent framework 3, the amino acids 89 to 97 represent "CDR-3," and the amino acids 98 to 111 represent framework 4. The amino acid sequence in the L chain portion of ScFv1-3 is shown in SEQ ID NO: 19. The amino acids 1 to 23 in SEQ ID NO: 19 represent framework 1, the amino acids 24 to 34 represent "CDR-1," the amino acids 35 to 49 represent framework 2, the amino acids 50 to 56 represent "CDR-2," the amino acids 57 to 88 represent framework 3, the amino acids 89 to 97 represent "CDR-3," and the amino acids 98 to 111 represent framework 4. The amino acid sequence in the L chain portion of ScFv1-4 is shown in SEQ ID NO: 20. The amino acids 1 to 22 in SEQ ID NO: 20 represent framework 1, the amino acids 23 to 36 represent "CDR-1," the amino acids 37 to 51 represent framework 2, the amino acids 52 to 58 represent "CDR-2," the amino acids 59 to 90 represent framework 3, the amino acids 91 to 102 represent "CDR-3," and the amino acids 103 to 116 represent framework 4. The boundary between these frameworks and CDRs was determined based on Kabat et al., "Immunologically useful protein sequence" (National Institutes of Health, Bethesda, Md., (1987) and (1991)).

ScFv can be prepared using, for example, Recombinant Phage Antibody System (Pharmacia). When the single-chain antibody is toxic to *Escherichia coli* as a production host and causes extinction of *Escherichia coli* or decomposition of the single-chain antibody, the kit cannot be effectively used and a lot of contrivances are required. The single-chain antibody can be prepared by selecting inducible vectors such as pSE380 plasmid (Invitrogen) or pET24d(+) plasmid (Novagen) and host bacterial cells. In addition to the above method, in the production of the single-chain antibody, an animal cell expression system, an insect cell expression system, and a yeast cell expression system can be effectively utilized. In Examples, 15 amino acid residues of 3 repeats of (Gly-Gly-Gly-Gly-Ser) were used as a linker for linking the H chain and the L chain. In the present invention, however, any linker can be used without being limited to this sequence.

SEQ ID NO: 21 in the Sequence Listing represents the nucleotide sequence of the nucleic acid corresponding to the amino acids 1 to 128 of SEQ ID NO: 16 in the Sequence Listing. SEQ ID NO: 22 in the Sequence Listing represents the nucleotide sequence of the nucleic acid corresponding to the amino acids 1 to 111 of SEQ ID NO: 17 in the Sequence Listing. SEQ ID NO: 23 in the Sequence Listing represents the nucleotide sequence of the nucleic acid corresponding to the amino acids 1 to 111 of SEQ ID NO: 18 in the Sequence Listing. SEQ ID NO: 24 in the Sequence Listing represents the nucleotide sequence of the nucleic acid corresponding to the amino acids 1 to 111 of SEQ ID NO: 19 in the Sequence Listing. SEQ ID NO: 25 in the Sequence Listing represents the nucleotide sequence of the nucleic acid corresponding to the amino acids 1 to 116 of SEQ ID NO: 20 in the Sequence Listing. Regarding these nucleotide sequences, a nucleotide sequence having a deletion, a substitution, or an addition of one or several nucleotides is included in the scope of the present invention as long as the sequence exhibits the effects as described in the present application.

The fact that the antigen-specificity of the antibody and the binding intensity to the antigen are mainly determined by the amino acid sequences of the CDR is demonstrated by the humanizaition of the mouse antibody (Methods in Enzymology, 203, 99–121, 1991).

Further, an antibody of a form which is usually present in a living organism can be prepared from scFv. For example, only the variable regions of the H chain and the L chain are amplified by PCR from scFv plasmid which binds to E2/NS1. Each fragment is, for example, integrated into a plasmid having the H chain gene and/or the L chain gene of the human antibody, thereby forming an antibody having a variable region on the scFv and being a form usually present in a living organism. More specifically, for example, suitable restriction enzyme cleavage sites are introduced at both ends of the gene fragment obtained when amplifying the variable regions of the H chain and the L chain from the plasmid, and they are combined with a suitable restriction enzyme cleavage site on the plasmid having the H chain and/or the L chain of the human antibody, thereby replacing genes in the variable region without causing frame-shift. Thus, an antibody of a form usually present in a living organism which has a sequence of the variable region on a plasmid as it is, can be prepared. Further, a peptide containing at least one antigen binding site formed by the variable region of the H chain or L chain of the antibody or a combination thereof, Fab composed of a set of an H chain fragment and an L chain fragment, and (Fab'2) composed of 2 sets of H chain fragments and L chain fragments can also be prepared from the antibody.

Further, substitution of sequences of antibodies mentioned below can enhance the binding force to E2/NS1 and the neutralizing activity; an antibody in which CDR-1, CDR-2, and CDR-3 in the variable region of the H chain in the present invention are, respectively, amino acid sequences shown by SEQ ID NOS: 1, 2, and 3 in the Sequence Listing and CDR-1, CDR-2, and CDR-3 in the variable region of the L chain are, respectively, amino acid sequences shown by SEQ ID NOS: 4, 5, and 6 in the Sequence Listing; an antibody in which CDR-1, CDR-2, and CDR-3 in the variable region of the H chain are, respectively, amino acid sequences shown by SEQ ID NOS: 1, 2, and 3 in the Sequence Listing and CDR-1, CDR-2, and CDR-3 in the variable region of the L chain are, respectively, amino acid sequences shown by SEQ ID NOS: 7, 8, and 9 in the Sequence Listing; an antibody in which CDR-1, CDR-2, and CDR-3 in the variable region of the H chain are, respectively, amino acid sequences shown by SEQ ID NOS: 1, 2, and 3 in the Sequence Listing and CDR-1, CDR-2, and CDR-3 in the variable region of the L chain are, respectively, amino acid sequences shown by SEQ ID NOS: 10, 11, and 12 in the Sequence Listing; or an antibody in which CDR-1, CDR-2, and CDR-3 in the variable region of the H chain are, respectively, amino acid sequences shown by SEQ ID NOS: 1, 2, and 3 in the Sequence Listing and CDR-1, CDR-2, and CDR-3 in the variable region of the L chain are, respectively, amino acid sequences shown by SEQ ID NOS: 13, 14, and 15 in the Sequence Listing. For example, the sequence of CDR-3 can be randomly substituted to obtain another antibody. A highly active antibody can be also obtained by substituting the amino acid sequences and gene sequences of CDR-1, CDR-2, and CDR-3 of the H chain and the L chain. In this case, an antibody having a modified amino acid sequence has no problem unless the neutralizing activity is deteriorated. That is, in the present invention, an amino acid sequence having modifications such as a substitution, a deletion, or an insertion is included in the scope of the present invention as long as the sequence has ability to inhibit the binding between E2/NS1 and the HCV infectious cell, the CD81 expressing cell, or CD81.

The antibodies of the present invention, ScFv2-1, ScFv2-2, ScFv2-3, and ScFv2-4, are antibodies having amino acid substitutions in the H chains of the above-described antibodies ScFv1-1, ScFv1-2, ScFv1-3, and ScFv1-4. The amino acid sequences and the DNA sequences of the H chains of the antibodies ScFv2-1, ScFv2-2, ScFv2-3, and ScFv2-4 are shown in SEQ ID NOS: 34 and 35 in the Sequence Listing.

Further, the amino acid sequences and the DNA sequences of the antibodies ScFv3-1, ScFv3-2, ScFv3-3, and ScFv3-4 of the present invention are shown in SEQ ID NOs: 42 to 65 in the Sequence Listing.

The descriptions on the antibodies ScFv2-1, ScFv2-2, ScFv2-3, ScFv2-4, ScFv3-1, ScFv3-2, ScFv3-3, and ScFv3-4 are the same as those given on the antibodies ScFv1-1, ScFv1-2, ScFv1-3, and ScFv1-4.

In the present invention, a full-length antibody is preferably used.

The expression of antibody in the present invention can carried out by employing *Escherichia coli,* yeast, insect cells, animal cells, and the like. If the antibody is to be administered to a human as a medicament, an animal cell showing a sugar chain modification which is closer to that of human, is preferably used. For example, when an antibody is expressed in COS cell or CHO cell, pCDNA3.1(+) or pMAMneo (CLONETECH) can be used. For example, a gene of the H chain of the antibody obtained in the above method is incorporated into a multicloning site of pCDNA3.1(+), and a gene of the L chain is incorporated into pMAMneo. An expression unit having a gene of the L chain between a promoter and poly A is then incorporated into an adequate site of the vector having the H chain incorporated therein. Introduction of this vector into a COS cell, a CHO-K1, or a CHO DG44 by a conventional genetic engineering technique enables the production of the antibody of interest. Further, the expression unit of the DHFR gene is cleaved out from for example, pSV2/DHFR (Nature, 1981. Vol. 294, Lee F. et al.) into the above prepared vector, and is incorporated into a vector which expresses the H chain and the L chain. This vector is introduced into the CHO DG44 by a conventional genetic engineering technique. The thus selected cells can be used to significantly improve the producibility of antibodies by utilizing the DHFR gene amplification system using MTX. In the COS cell, the antibody can be expressed only in the transient manner. In the CHO cell, the antibody can be expressed in a state in which the antibody genes are incorporated into a chromosome. Also, the above-described DHFR gene amplification system can be used to express an antibody at a high level, and the use of the CHO cell is more preferred in the industrial production since the antibody can be produced in a serum-free medium.

The COS cell is generally cultured in Dulbecco's Modified Eagle's Medium (DMEM) supplemented with 10% fetal bovine serum (FBS) under 5% $CO_2$ at 37° C. The method for breeding and producing cells after gene introduction into the COS cell is described in protocols such as "Bio Manual Series 4, Gene Introduction and Expression—Analytical Method); Takashi Yokota, Ken-ichi Arai" (YODOSHA Co., Ltd., 1994). A method for introducing a gene into the COS cell may be electroporation, as well as a DEAE-dextran method and a method using a transfection reagent such as lipofectin.

CHO K-1 cell and CHO-DG44 cell can be cultured in DMEM supplemented with 10% FBS, as well as a commercially available serum-free medium such as CHO S SFM2 (GIBCO), under 5% $CO_2$ at 37° C. As in the case of COS cells, gene introduction into the CHO cell can be carried out by electroporation, as well as a DEAE-dextran method and a method using a transfection reagent such as lipofectin. In particular, in the case of the CHO DG44, the producibility of the antibody can be enhanced by gene amplification by culturing the cell in a medium free from hypoxanthine or thymidine and adding a DHFR inhibitor, i.e., MTX, in the medium.

At the time of production of antibody in the present invention, the cells are preferably cultured in a serum-free medium in order to prevent the contamination of a serum-derived bovine antibody. COS and CHO cells which are not acclimatized in a serum-free medium but are cultured in serum media, are preferably cultured in DMEM free from serum. The antibody of the present invention, which is thus obtained in the culture supernatant, can be easily purified by a conventional method for purifying IgG antibodies using, for example, Protein A column and Protein G column.

The antibody produced in the present invention can be used in the treatment of HCV. As a form of the antibody, the produced antibody molecules can be used as it is. It is also possible to use Fab, F(ab')2, Fv, or Fd, which are fragments containing antigen binding sites obtained by various protease treatments, and the whole antibody is most preferred. These fragments are described in detail in "Introductory Antibody Engineering" (Chijinshokan Co., Ltd.). Fragmented peptides can be obtained by enzymatic treatment of antibody molecules. Alternatively, fragmented peptides can be produced by bacteria, yeast, or the like by a genetic engineering technique. By the combination of the thus obtained monoclonal antibody, monoclonal antibody-derived antibody fragment, peptide and the like, stronger binding properties can be made.

The antibody produced in the present invention can be used to decrease HCV particles in the blood of an HCV infected patient. For example, by administering the antibody produced in the present invention to a patient where mRNA of HCV or the anti-HCV antibody is observed by a commercially available HCV diagnostic agent, the amount of HCV particles in the blood can be decreased, thereby preventing re-infection with HCV and leading the patient to recovery from HCV. Further, upon administration to the HCV patient, this antibody can bind in particular to cells which present E2/NS1 on the cell surface among HCV infected cells in the body of the HCV patient. It can also be expected that this binding and the activation of an immune system such as a complement in the living organism will result in killing ability against HCV infected cells. Further, combination with a gene of a variable region derived from other antibodies enables the production of a bispecific antibody and a multispecific antibody. A "multispecific antibody" refers to an antibody which has at least two antigen binding sites which recognize different antigens or different epitopes of the same antigen. Among them, a "bispecific antibody" refers to an antibody which has at least two antigen binding sites which recognize different antigens or epitopes. For example, it is considered that a bispecific antibody wherein the antigen binding site of a general antibody is different from the other antigen binding site can bind more strongly to an antigen, and can bind to HCV of broad sequences as compared to a general antibody. Further, an antibody which recognizes an antigen in a more multivalent manner as IgM can also be prepared. In addition to the procedure to make the antibody bispecific at the time of production, a bispecific or multispecific antibody can be produced by producing and purifying monoclonal antibodies and then binding the antibodies to each other. This procedure to make the antibody bispecific can be carried out by combining not only with the same antigen, but also with another antigen. For example, an antibody against E1 which is considered to be presented on the surface of the HCV particles can be used to prepare a bispecific antibody and a multispecific antibody.

The amino acid sequences of the single-chain antibodies ScFv1-1, ScFv1-2, ScFv1-3, and ScFv1-4 are shown in SEQ ID NO: 26, SEQ ID NO: 27, SEQ ID NO: 28, and SEQ ID NO: 29 in the Sequence Listing. Examples of nucleic acid sequences encoding those are shown together with the amino acid sequences. The amino acids 1 to 22 of the amino acid sequence shown by SEQ ID NO: 26 represent a sequence containing a secretion signal from *Escherichia coli*, the amino acids 23 to 148 represent a variable region of the H chain, the amino acids 149 to 165 represent a linker, the amino acids 166 to 276 represent a variable region of the L chain, and the amino acids 277 to 299 represent a sequence containing a tag. The amino acids 1 to 22 of the amino acid sequence shown by SEQ ID NO: 27 represent a sequence containing a secretion signal from *Escherichia coli*, the amino acids 23 to 148 represent a variable region of the H chain, the amino acids 149 to 165 represent a linker, the amino acids 166 to 276 represent a variable region of the L chain, and the amino acids 277 to 299 represent a sequence containing a tag. The amino acids 1 to 22 of the amino acid sequence shown by SEQ ID NO: 28 represent a sequence containing a secretion signal from *Escherichia coli*, the amino acids 23 to –148 represent a variable region of the H chain, the amino acids 149 to 165 represent a linker, the amino acids 166 to 276 represent a variable region of the L chain, and the amino acids 277 to 299 represent a sequence containing a tag. The amino acids 1 to 22 of the amino acid sequence shown by SEQ ID NO: 29 represent a sequence containing a secretion signal from *Escherichia coli*, the amino acids 23 to 148 represent a variable region of the H chain, the amino acids 149 to 165 represent a linker, the amino acids 166 to 281 represent a variable region of the L chain, and the amino acids 282 to 304 represent a sequence containing a tag.

It is also possible to delete the amino acids 1 to 22 of the amino acid sequences shown by SEQ ID NO: 26, SEQ ID NO: 27, SEQ ID NO: 28, and SEQ ID NO: 29 and express a single-chain antibody in the cells of *Escherichia coli*. The amino acids 277 to 299 of the amino acid sequences shown by SEQ ID NO: 26, SEQ ID NO: 27, and SEQ ID NO: 28 represent a sequence for detecting and purifying the single-chain antibody, and this sequence can be deleted or substituted with any sequence. Similarly, the amino acids 282 to 304 of the amino acid sequence shown by SEQ ID NO: 29 are a sequence for detecting and purifying the single-chain antibody, and the sequence can be deleted or substituted with any sequence. A vector comprising a secretion signal from *Escherichia coli* and a sequence for purification is prepared in a manner described in Examples. The linker sequences of the amino acids 149 to 165 of the amino acid sequences shown by SEQ ID NO: 26, SEQ ID NO: 27, SEQ ID NO: 28, and SEQ ID NO: 29 can be substituted with any sequence as long as the sequence can maintain the steric structure of the variable regions of the H chain and the L chain substantially the same as scFv1-1. The single-chain antibody can be produced in animal cells, insect cells, and yeast cells, as well as *Escherichia coli*.

The amino acid sequences of single-chain antibodies ScFv2-1, ScFv2-2, ScFv2-3, and ScFv2-4 are shown in SEQ ID NO: 36, SEQ ID NO: 37, SEQ ID NO: 38, and SEQ ID NO: 39 in the Sequence Listing, and examples of nucleic acid sequences encoding those are shown together with the amino acid sequences.

Further, the amino acid sequences of single-chain antibodies ScFv3-1, ScFv3-2, ScFv3-3, and ScFv3-4 are shown in SEQ ID NO: 62, SEQ ID NO: 63, SEQ ID NO: 64, and SEQ ID NO: 65 in the Sequence Listing. Examples of nucleic acid sequences encoding those are shown together with the amino acid sequences.

The descriptions on single-chain antibodies ScFv2-1, ScFv2-2, ScFv2-3, ScFv2-4, ScFv3-1, ScFv3-2, ScFv3-3, and ScFv3-4 are the same as those given on ScFv1-1, ScFv1-2, ScFv1-3, and ScFv1-4.

A single-chain antibody can be made bispecific and multispecific. For example, it can be produced by repeatedly arranging the H chains and the L chains of a plurality of combinations of antigen recognition sites in a peptide. Ligation after production and purification is also possible. The H chain or the L chain can be used alone instead of a combined use of the H chain and the L chain. The type of the antibody can be selected depending on the application for use, and can be selected based on a binding intensity, an antigen binding site, and the like.

The present invention further provides a medicament which comprises, as an active ingredient, the above-described antibody, a substance having the function equivalent thereto and inhibiting the binding between E2/NS1 and the HCV infectious cell, the CD81 expressing cell, or CD81 as defined in the present invention, for example, a pharmaceutical composition comprising the above substance and a pharmaceutically acceptable carrier. More particularly, the anti-E2/NS1 antibody gene of the present invention can efficiently produce the anti-E2/NS1 antibody, and provides various forms of therapeutic preparations. The recombinant antibodies thus produced may be contained in the pharmaceutical composition together with the substance which is used for sustaining the activity of the antibody at the time of administration to human, such as a carrier having a pharmaceutically acceptable composition and a stabilizer. Examples of such carriers and stabilizers include human serum albumin and gelatin. The term "pharmaceutically acceptable" means that neither undesirable side-effects accompanying administration, such as nausea, vertigo and retching, nor an immune response to the preparation at a time of frequent administration occurs. Further, the antibody prepared by binding a substance such as a toxin to the antibody of the present invention can be used as a medicament. A liquid pharmaceutical composition dissolved with a pharmaceutically acceptable suitable solvent, diluent, or stabilizer, may also be used. In addition to the above pharmaceutical composition, in the case of parenteral administration (injection) of microsphere and liposome for the purpose of controlling concentration in the living organism, 1 μg to 50 mg/kg (body weight) of an antibody and a single-chain antibody is suitable, although it is not limited to this range.

In the foregoing, the antibody was described as a representative example. Applicable examples of a substance which inhibits the binding between E2/NS1 and the HCV infectious cell, CD81 expression cell, or CD81 in the present invention include the antibody, as well as a protein other than an antibody, sulfated polysaccharides, or low molecular weight compounds, unless the activity of the present invention is deteriorated.

Proteins other than the antibody include lactoferrin, and the preparation as a pharmaceutical composition and the administration method can be selected in accordance with those in the case of the aforementioned antibody.

"Sulfated polysaccharides" used in the present invention refers to, for example, what are called glycosaminoglycans and dextran sulfate, such as heparin, heparan sulfate, chondroitin sulfate A, chondroitin sulfate C, dermatan sulfate, keratan sulfate 1, and keratan sulfate 2, having an average molecular weight of 5,000 Da to 1,000,000 Da. Heparin having a size of about 5,000 Da to 30,000 Da is preferred. Examples of administration methods include, but are not limited to: intravenous drip of 10,000 to 30,000 units diluted with 5% liquid glucose, physiological saline, or Ringer's solution; intermittent intravenous infusion administering 5,000 to 10,000 units per dose every 4 to 8 hours, from 3 hours after the initiation of injection, every 2 to 4 hours; and subcutaneous/intramuscular injection of 15,000 to 20,000 units of concentrated solution preparation initially, followed by administration of a maintenance dosage twice a day of 10,000 to 15,000 units per dose.

The low molecular weight compound used in the present invention is sumarin and the like described below in the Examples, but it is not limited thereto as long as the substance can inhibit the infection of E2/NS1 of HCV and HCV.

Various binding sites of the low molecular weight compound can be considered. If the substance binds to a site to which the heparin binds, a compound having a sulfate group added thereto is preferred.

When proteins such as an antibody, sulfated polysaccharides, and low molecular weight compounds cited herein are used as a medicament, they are not necessarily used alone. A plurality of substances can be administered in an amount within the range described in the present specification regarding each substance.

In the case of the single-chain antibody, it can be preferably used for diagnosing hepatitis C virus.

The present invention relates to a substance which inhibits a life cycle of hepatitis C virus, which is obtained by the screening method which comprises steps of assaying the binding between a cell infectious with HCV and a cell expressing HCV protein in the presence and absence of the test substance, and comparing it with the binding in the absence of the test substance; and a substance which inhibits a life cycle of hepatitis C virus, which is obtained by the screening method which comprises steps of, after the cell infectious with HCV has bound with the HCV protein expressing cell in the presence or absence of the test substance, assaying the fusion between the test substance and the cell infectious with HCV or the HCV protein expressing cell, and comparing it with the fusion in the absence of the test substance. Examples of a life cycle of hepatitis C virus referred to herein include infection and proliferation of hepatitis C virus.

The literature by Takikawa et al. (Takikawa et al., J. Virol., 74, 5066–5074, 2000) describes an assay system capable of assaying the binding and the fusion of the HCV infectious cells (HepG2) and CHO cells expressing HCV protein and a mechanism of HCV infection using the same.

The antibody obtained in the present invention is a novel substance which can competitively neutralize the assay system.

The cell fusion assay system is a system used in the assay of the cell fusion activity of viruses in HTLV-1 and the like. The assay system of the present invention is a system which falsely exhibits cell fusion of HCV. Thus, it is expected that a substance which inhibits this assay system has an effect of inhibiting HCV infection, particularly inhibiting the binding to cells and the enucleation.

EXAMPLES

The present invention is described below in more detail with reference to the examples, but the present invention is not limited to the following examples.

1. Expression of E2

(Construction of E2tag Expression Vector)

100 ng of a region of 711 amino acids from the amino acid 384 in HCV genome of E2/NS1 of HCV J1 clone gene (Genbank Registration No: D89815) was used, and the DNA (tPA signal+E2(384-711)+tag) fragment was amplified by PCR using a PCR primer for the 5' side of the gene (5'CCC AAG CTT ACC ATG GAT GCA ATG AAG AGA GGG CTC TGC TGT GTG CTG CTG CTG TGT GGA GCA GTC TTC GTT TCG GCT AGC CAT ACC CGC GTG ACG GGG GGG GTG CAA GG 3'; SEQ ID NO: 30) having a signal peptide sequence for promoting secretion in animal cells and a PCR primer for 3' side of the gene (5'CCC CCT CGA GTC TAG ATT AAC GCG GTT CCA GCG GAT CCG GAT ACG GCA CCG GCG CAC CGG AGA CGA CCG CCG ACC CTA TAC C 3'; SEQ ID NO: 31) having an E-tag sequence as primers for PCR amplification. PCR reaction was performed using Perkin Elmer Cetus DNA Thermal Cycler and KOD polymerase (purchased from Toyobo Co., Ltd., the reaction conditions were in accordance with the instructions). Thereafter, a desired DNA fragment was purified by 5% acrylamide electrophoresis in accordance with the method described in "Molecular Cloning, Section 6.46–6.48, Cold Spring Harbor." 1 μg of the purified DNA fragment was reacted in 50 μL of system M (10 mM Tris-HCl, 50 mM NaCl, 2 mM $MgCl_2$) using 1 unit of HindIII and XbaI at 37° C. for 2 hours and cleaved. The enzyme was deactivated by heating at 70° C. for 10 minutes. The product and 1 μg of expression vector pCDNA3.1(+) for animal cells (purchased from Invitrogen) was reacted in 50 μL of system M (10 mM Tris-HCl, 50 mM NaCl, 2 mM $MgCl_2$) using 1 unit of HindIII and XbaI at 37° C. for 2 hours and cleaved, and the enzyme was deactivated by heating at 70° C. for 10 minutes. A solution containing phenol, chloroform and isoamyl alcohol at a ratio of 25:24:1, the amount of which is the same as that of the enzyme solution, was added thereto and mixed. The resultant mixture was centrifuged, and only a water layer was collected (this operation is hereinafter referred to as "phenol-chloroform extraction"). Further, 1/10 volume of 3M sodium acetate and 2.5× volume of ethanol were mixed with the collected water layer, and the mixture was allowed to stand at −20° C. overnight or at −80° C. for 15 minutes. The mixture was centrifuged to collect a DNA fragment. After the addition of 70% ethanol, decantation was performed and vacuum drying was conducted (this series of operations of adding ethanol followed by collection of DNA fragments is hereinafter referred to as "ethanol precipitation"). Thereafter, the collected DNA fragments were dissolved in 5 μL of sterilized water. These purified DNA fragments were ligated to each other using a ligase kit (purchased from Takara Shuzo Co., Ltd., the reaction was in accordance with the instructions), and *Escherichia coli* strain JM109 (purchased from Takara Shuzo Co., Ltd., the reaction was in accordance with the instructions) was transformed to obtain the desired E2tag expression plasmid, pE2tag.

(Expression of E2tag in Animal Cell)

*Escherichia coli* carrying plasmid pE2tag was cultured in a 50 mL baffle flask overnight. Bacterial cells were collected by centrifugation at 8,000 rpm for 10 minutes and a plasmid was purified using QIAGEN Plasmid Midi kit (purchased from QIAGEN) in accordance with the instructions.

The purified plasmid was transfected to strain CHO DG44 cultured in EX-CELL302 (purchased from JRH) supplemented with 5% FBS by using lipofectin (purchased from LIFETECH) in accordance with the instructions. CHO DG44 was cultured in 5% $CO_2$ at 37° C. 2 days after the transfection, cells were treated with 0.25% trypsin, and the cells were then inoculated in EX-CELL302 supplemented with G418 at 400 μg/mL. Media were exchanged using G418-added media for about 2 weeks and the rise of colonies was observed.

E2tag expression in the obtained cell was observed by Western blotting of the cell supernatant. Western blotting was performed in accordance with the instructions of Anti-E Tag Antibody purchased from Pharmacia. HRP-bound goat anti-mouse IgG antibody was used as a detection antibody. The light emission reaction was performed using ECL Western blotting detection reagents (purchased from Amersham Pharmacia Biotech) in accordance with the instructions by exposing X-ray film. Among the selected clones, the cell expressing the highest amount of E2tag was used in the later experiments.

(Purification of E2tag)

The clone expressing E2tag which obtained by the above method was cultured in EX-CELL302 so as to obtain a necessary amount of supernatant. When the logarithmic growth phase of the cell was terminated, the cells were removed by centrifugation and the supernatant was collected. Contaminant was further removed from the supernatant using a 0.45 μm filter. The supernatant thus obtained was subjected to affinity purification using RPAS Purification Module (purchased from Pharmacia). Purification was performed in accordance with the instructions attached to RPAS Purification Module. E2tag was substituted into PBS since E2tag can be obtained in the Elution buffer attached to RPAS Purification Module. More specifically, the elution fraction containing the above E2tag was added to the upper portion of the filter of Centricon 30 (purchased from Amicon), and centrifugation was performed at 5,000 rpm until the amount of the buffer contained therein became 100 μL or below. About 2 mL of PBS was added thereto and centrifugation was performed in the same manner. This procedure was repeated four times or more to collect E2tag dissolved in PBS.

2. Construction of NOB Assay System (Construction of CD81 Expression Vector)

In order to obtain the full length DNA of human CD81 gene (Genbank Registration No. M33680), cDNA was synthesized from 1 µg of mRNA purified from Hela cell using RT-PCR kit ver 2.1 (TAKARA) in accordance with the attached information and using a random primer. Subsequently, in accordance with the information attached to this kit, PCR reaction was carried out by setting GCGCCGC-CATGGGAGTGGAGGGCTGC (SEQ ID NO: 32) for the 5'-side and CTCAGTACACGGAGCTGTTCCGGA (SEQ ID NO: 33) for the 3'-side as primers for PCR amplification. The PCR product was subjected to 0.8% agarose gel electrophoresis, and the band of interest was purified using QIAEX II Gel Extraction Kit (purchased from QIAGEN) in accordance with the attached instructions. By using TOPO TA Cloning KIT with TOP10F' Cells (purchased from Invitrogen), pCR2.1-TOPO was ligated with the fragment of the CD81 of interest, and Escherichia coli was transformed with the ligation product in accordance with the attached instructions, thereby obtaining pCRhCD81 of interest. Further, 1 µg of pCRhCD81 was reacted using 1 unit of EcoRI in 50 µL of system H (10 mM Tris-HCl, 100 mM NaCl, 2 mM $MgCl_2$) at 37° C. for 2 hours and cleaved, and the enzyme was deactivated by heating at 70° C. for 10 minutes. Then, the fragment containing CD81 genes was purified using QIAEXII Gel Extraction Kit (purchased from QIAGEN) in accordance with the attached instructions. Separately, pCDNA3.1(+) was also treated with EcoRI in the similar system and the enzyme was deactivated. Thereafter, 1 µL of bacterial alkali phosphatase (purchased from Toyobo Co., Ltd.) was added, and the mixture was incubated at 65° C. for 1 hour. After purification by phenol-chloroform extraction and ethanol precipitation, the collected DNA fragments were dissolved in 5 µL of sterilized water. Further, both fragments were ligated to each other using a ligase kit (purchased from Takara Shuzo Co., Ltd., the reaction was in accordance with the instructions), and Escherichia coli strain JM109 (purchased from Takara Shuzo Co., Ltd., the reaction was in accordance with the instructions) was transformed to obtain the desired CD81 expression plasmid, pCDNA3.1(+)/CD81.

(Construction of CD81 Expression Cell)

Escherichia coli carrying plasmid pCDNA3.1(+)/CD81 was cultured in a 50 mL baffle flask overnight. Bacterial cells were centrifuged at 8,000 rpm and a plasmid was purified using QIAGEN Plasmid Midi kit (purchased from QIAGEN) in accordance with the instructions.

The purified plasmid was transfected into NIH3T3 strain cultured in Dulbecco's Modified Eagle's Medium (DMEM) supplemented with 10% FBS using lipofectin (purchased from LIFETECH) in accordance with the instructions. NIH3T3 was hereinafter cultured in 5% $CO_2$ at 37° C. 2 days after the transfection, the cells were treated with 0.25% trypsin and the cells were then inoculated in DMEM supplemented with 10% FBS and 800 µg/mL of G418. The medium was exchanged using G418-added medium for about 2 weeks, and the rise of colonies was confirmed.

CD81 expression in the obtained cell lines was confirmed in accordance with the following procedure. The obtained cell lines were cultured in the selective medium on the 6-well plate until the cell lines became confluent. The cells were washed once with PBS/0.05% EDTA, then detouched using PBS/0.05% EDTA, and suspended in 20 µL of PBS containing 0.1% BSA and 0.1% azide (hereinafter referred to as "FACS buffer"). An anti-CD81 antibody (purchased from Pharmingen) was added in the final concentration of 0.025 mg/mL and mixed, and the mixture was then incubated on ice for 1 hour. 200 µL of FACS buffer was added and the cells were then collected by centrifugation at 3,000 rpm. This procedure was repeated twice. The collected cells were suspended in 30 µL of FACS buffer, FITC-labeled rabbit anti-mouse Igs antibody (purchased from Cappel) was added in the final concentration of 0.05 mg/mL, followed by mixing. The mixture was incubated under a shaded condition on ice for 1 hour. 200 µL of FACS buffer was added, and the cells were then collected by centrifugation at 3,000 rpm. After this procedure was repeated twice, the cells were suspended in 200 µL of FACS buffer, and the fluorescence level of the cells was measured using FACScan (Becton Dickinson Company, Ltd.). The cell showing the highest fluorescence level was selected, and was designated "NIH3T3/CD81."

(Confirmation of Binding Between E2tag and Molt-4 or NIH3T3/CD81)

The final concentration of Molt-4 (RIKEN, RCB No. 0206) or NIH3T3/CD81 was set at $5 \times 10^6$ cell/mL, and mixed with E2tag by separately setting the concentrations so as to bring the final concentration of E2tag to 50 µg/mL or below, and the mixture was incubated in RPMI 1640 containing 1% FBS in 20 µL of system on ice for 1 hour. 200 µL of PBS containing 5% FBS was added and the cells were then collected by centrifugation at 3,000 rpm. This procedure was repeated twice. The anti-Etag antibody was diluted to 10 µg/mL with RPMI 1640 containing 1% FBS, and 10 µL of the diluted antibody was added to each sample and mixed. Thereafter, the mixture was incubated on ice for 1 hour. 200 µL of PBS containing 5% FBS was added, and the cells were then collected by centrifugation at 3,000 rpm. This procedure was repeated twice. 10 µL of solution prepared by diluting FITC-labeled rabbit anti-mouse Igs (purchased from Cappel) to a final concentration of 25 µg/mL with PBS containing 5% FBS was added to each sample and mixed. Thereafter, the mixture was incubated on ice for 1 hour. 200 µL of PBS containing 5% FBS was added, and the cells were then collected by centrifugation at 3,000 rpm. This procedure was repeated twice. The sample was suspended in 200 µL of PBS containing 5% FBS, and the change in the fluorescence level of cells was measured by FACScan (Becton Dickinson Company, Ltd.). Thus, the binding between E2tag and Molt-4 or NIH3T3/CD81 was confirmed.

(Confirmation of Inhibitor of Binding Between E2tag and Molt-4 or NIH3T3/CD81)

A solution prepared by diluting E2tag with RPMI 1640 containing 1% FBS to the final concentration of 50 µg/mL was mixed with 10 µL each of a solution prepared by diluting scFv (the antibody obtained by the screening method described below in the present specification) in the range of 0.125 µg/mL to 12.5 µg/mL, a solution prepared by diluting heparin (SIGMA, H3393) in the range of 4 µg/mL to 400 µg/mL, and a solution prepared by diluting suramin (SIGMA, S2671) in the range of 50 µg/mL to 5,000 u g/mL, with RPMI 1640 containing 1% FBS, respectively. The resultant mixtures were incubated at 37° C. for 30 minutes. 10 µL of solution prepared by suspending Molt-4 or NIH3T3/CD81 in RPMI 1640 containing 1% FBS at a concentration of $1 \times 10^7$ cell/mL was mixed therewith and the resultant mixture was incubated on ice for 1 hour. 200 µL of PBS containing 5% FBS was added and the cells were then collected by centrifugation at 3,000 rpm. This procedure was repeated twice. The anti-Etag antibody was diluted to 10 µg/mL with RPMI 1640 containing 1% FBS, 10 µL thereof was added to each sample, and mixed. The mixture was then incubated on ice for 1 hour. 200 μL of PBS containing 5% FBS was added and the cells were then collected by centrifugation at 3,000 rpm. This procedure was repeated twice. 10 μL of solution prepared by diluting FITC-labeled anti-mouse Igs (purchased from Cappel) with PBS containing 5% FBS to a final concentration of 25 μg/mL was added to each sample and mixed. Thereafter, the mixture was incubated on ice for 1 hour. 200 μL of PBS containing 5% FBS was added, and the cells were then collected by centrifugation at 3,000 rpm. This procedure was repeated twice. The sample was suspended in 200 μL of PBS containing 5% FBS, and the change in the fluorescence level of the cells was then measured by FACScan (Becton Dickinson Company, Ltd.). Thus, it was confirmed that the binding between E2tag and Molt-4 or NIH3T3/CD81 was inhibited by the added patient's serum or antibody.

Figure 2:
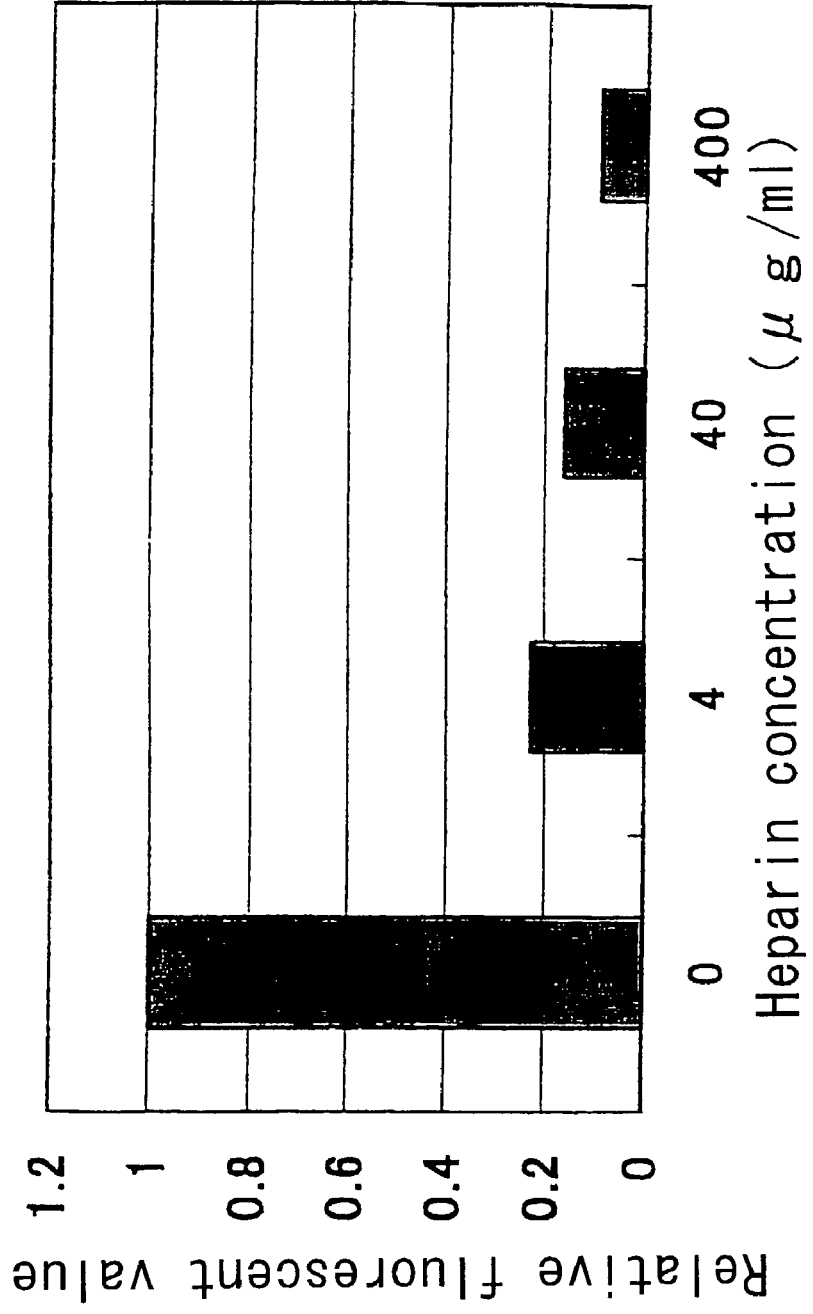
FIG. 2 is a diagram showing a neutralizing activity of heparin.
Figure 3:
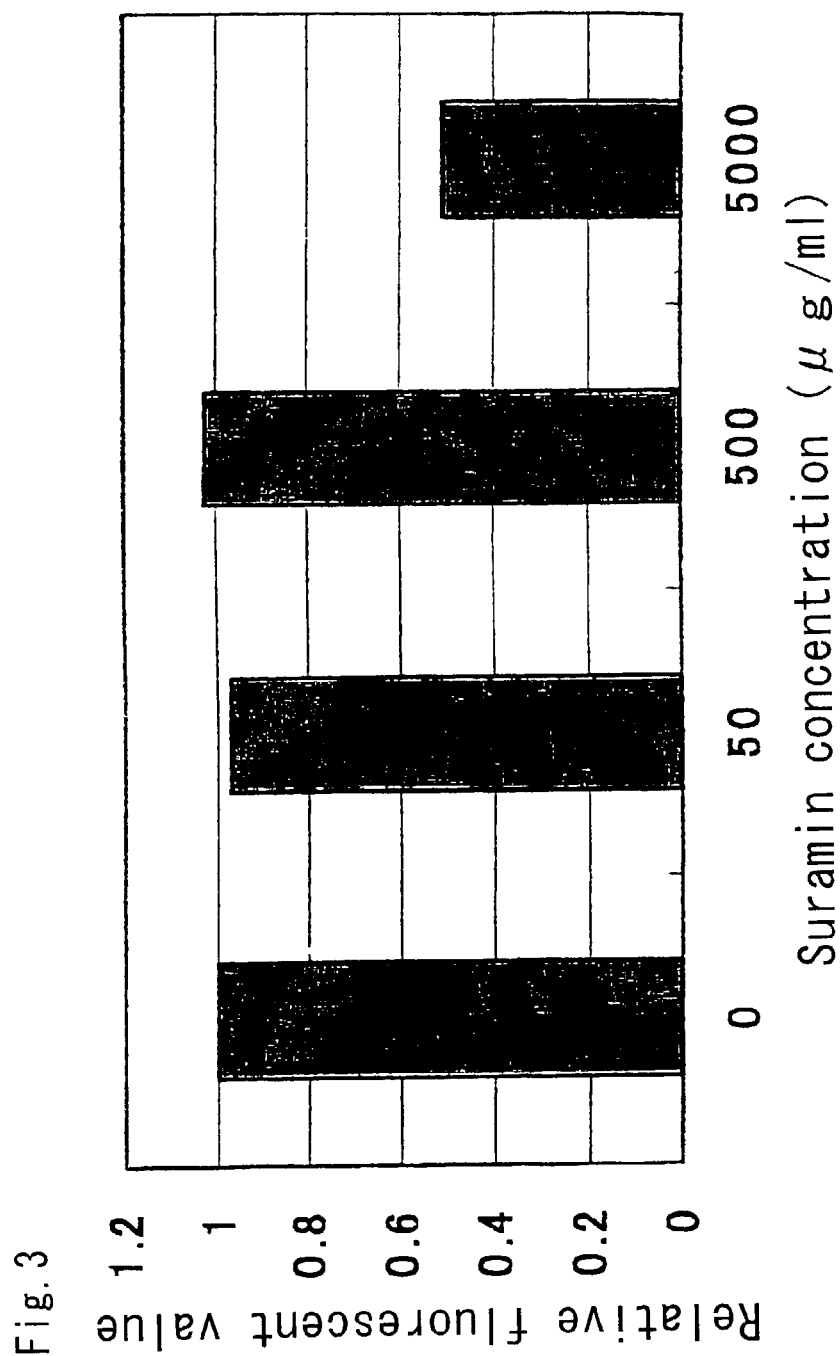
FIG. 3 is a diagram showing a neutralizing activity of suramin.
Figure 4:
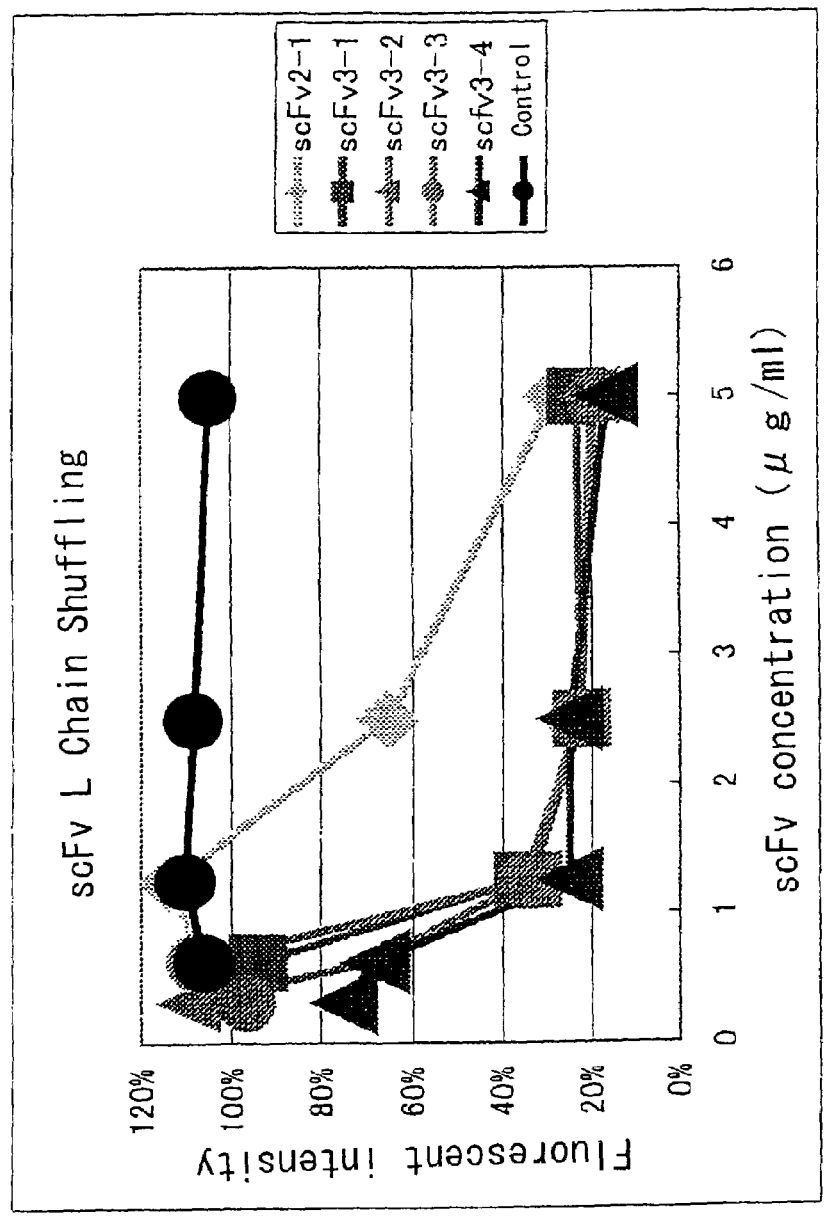
FIG. 4 is a diagram showing an NOB activity of modified scFv.
Figure 5:
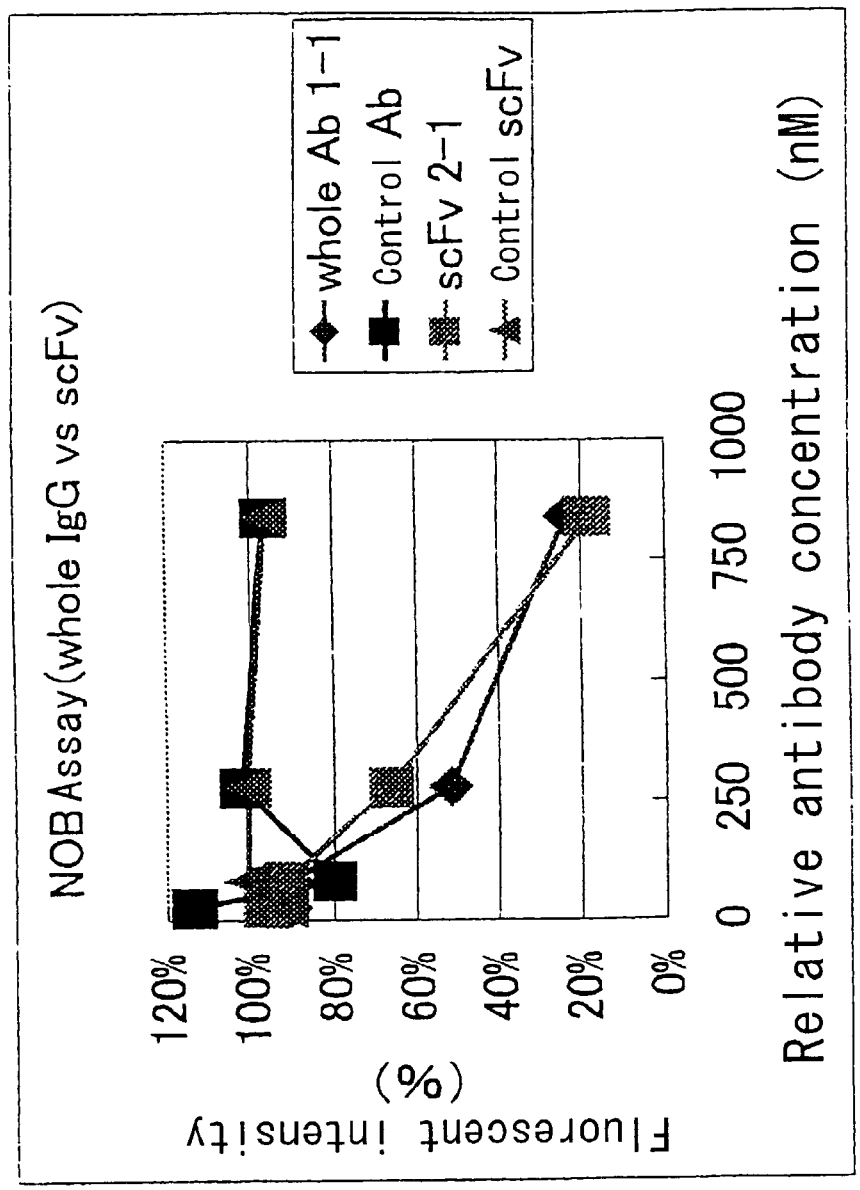
FIG. 5 is a diagram showing an NOB activity of a whole antibody.
Figure 6:
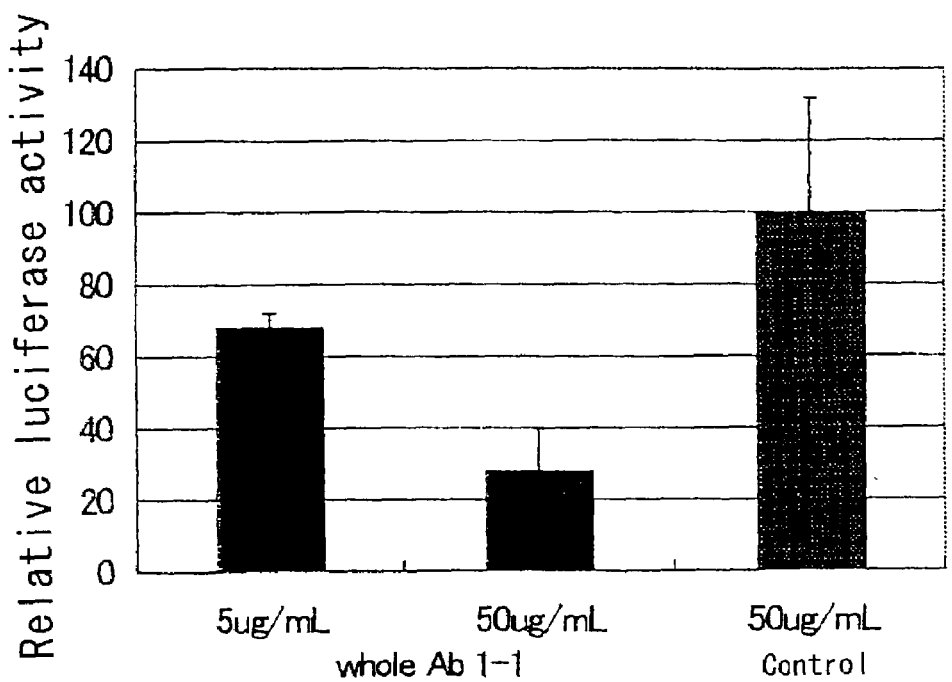
FIG. 6 is a diagram showing an inhibitory activity against cell fusion of the whole antibody.

Results are shown in FIGS. 1 to 3. FIG. 1 shows the neutralizing activity of the antibody shown by the aforementioned amino acid sequence. In FIG. 1, scFv1-1 and scFv1-4 correspond to antibodies shown by the aforementioned amino acid sequence, and the control shows a single-chain antibody which recognizes VLA 4. FIG. 2 shows the neutralizing activity when heparin is used, and FIG. 3 shows the neutralizing activity when suramin is used.

3. Preparation of Antibody Library (Purification of mRNA from Patient who Recovered from HCV)

From a patient who had recovered from HCV and has an antibody in the collected serum capable of inhibiting the binding between E2tag and Molt-4 or NIH3T3/CD81 expression cell, 40 mL heparin blood was sampled to collect blood. In order to separate peripheral blood lymphocyte, specific gravity centrifugation (Ficoll-Paque: Pharmacia) was performed to obtain $4 \times 10^7$ of lymphocytes. B-cell purification by anti-CD19 antibody using MACS (manufactured by Daiichi Pure Chemicals Co., Ltd.; Miltenyi Biotech GmbH) was performed to obtain $2.8 \times 10^6$ of cells. In order to confirm the purity of B-cells in the purified cells, the cells purified by the anti-CD19 antibody were stained to confirm by flow cytometry that the level of purification was 95% or higher. The purified B-cells were cultured for 72 hours under the stimulation of 200 unit/mL of human IL-2 (Genzyme), 10 ng/mL of human IL-10 (Genzyme), 1 ng/mL of E2/NS1 antigen and 1 μg/mL of anti-human CD40 antibody (Genzyme) in the condition of $5 \times 10^5$ B-cell/ml of 10% FCS RPMI. Activation of B-cells was confirmed using a microscope, the cells were washed with PBS twice, and mRNA was obtained and purified from B-cells using RNA later (Ambion) in accordance with the instructions.

(Preparation of Antibody Library)

The antibody library was prepared in accordance with the method described in "By-Passing Immunization Human Antibodies from V-gene Libraries Displayed on Phage (Journal of Molecular Biology 1991 222 582–597)." cDNA was synthesized from 1 μg of purified mRNA using RT-PCR kit ver 2.1 (TAKARA) in accordance with the attached information by using random primer. In accordance with the information attached to this kit, H chain and L chain (λ chain, κ chain) of the antibody were then amplified by PCR using this cDNA as a template. The primer and the linker for cloning antibody genes were prepared and used in accordance with the description in the above literature. The PCR product was subjected to 1% agarose gel electrophoresis, and the bands of H chain and L chain of the antibody were cut out. From the agarose gel which was cut out, DNA was extracted using QIAEX II Gel extraction kit (QIAGEN). Subsequently, the extracted H chain, L chain, and linker were mixed so that their moles became equivalent to each other, and PCR was performed using a primer for ligation. PCR was performed in 50 μL of system using 1 unit of Taq polymerase (Perkin Elmer) by heating at 94° C. for 5 minutes, repeating 30 cycles of 94° C. for 30 seconds, 55° C. for 30 seconds and 72° C. for 30 seconds, and then heating at 72° C. for 5 minutes. The PCR product was subjected to 1% agarose gel electrophoresis, and a band having H chain, L chain and the linker ligated to each other in single band was cut out. From the agarose gel which was cut out, DNA was extracted using QIAEX II Gel extraction kit (QIAGEN). Subsequently, the extracted DNA was reacted with a restriction enzyme SfiI in 50 μL of system M (10 mM Tris-HCl, 50 mM NaCl, 2 mM MgCl$_2$) at 55° C. for 2 hours and cleaved, and the enzyme was deactivated by heating at 70° C. for 10 minutes. The restriction enzyme NotI was further added, and the DNA was reacted in 50 μL of system M (10 mM Tris-HCl, 50 mM NaCl, 2 mM MgCl$_2$) at 37° C. for 2 hours and cleaved, and the enzyme was deactivated by heating at 70° C. for 10 minutes. The DNA was successively purified by phenol-chloroform extraction and ethanol precipitation and then dissolved in 50 μL of sterilized water. 100 ng of this DNA fragment and 50 ng of pCantab5MycHis (a vector prepared by substituting Etag sequence of pCantab5E (Amersham Pharmacia) with Myc-Histag) were ligated to each other using a ligase kit (TAKARA) in accordance with the instructions. The ligation sample was successively purified by phenol-chloroform extraction and ethanol precipitation and then dissolved in 10 μL of sterilized water. A half aliquot thereof was used to perform transformation in accordance with Molecular Cloning (1982) p249, Cold Spring Harbor Labs. Thus, $1 \times 10^6$ colonies were obtained. This colony was hereinafter used as a single-chain antibody library.

4. Screening of Library Phage (Preparation of Phage)

*Escherichia coli* grown on the plate was collected with 2 ml of 2×TY liquid medium, and 20 μl thereof was added to 20 ml of 2×TY liquid medium (containing 100 μg/L ampicillin and 2% glucose). The *Escherichia coli* was cultured until the absorbance at 600 nm became 1.0 while shaking at 37° C. at 200 rpm. $1 \times 10^{11}$ pfu/mL helper phage M13KO7 was added to the culture solution, and the mixture was allowed to stand at 37° C. for 30 minutes. Subsequently, the mixture was shaken at 37° C. at 200 rpm. 30 minutes later, the solution was centrifuged at 3,000 rpm for 10 minutes to collect *Escherichia coli*. The supernatant was discarded, and *Escherichia coli* was suspended in 20 ml of 2×TY liquid medium (containing 100 μg/L ampicillin and 50 μg/L kanamycin), and cultured overnight while shaking at 37° C. at 200 rpm. On the following day, the culture solution was centrifuged at 15,000 rpm to precipitate *Escherichia coli*, and the supernatant was collected. This supernatant was used as a phage solution.

(Screening Operation)

1 ml of E2 antigen (10 μg/ml) dissolved in a solution of 50 mM NaHCO$_3$ (pH 9.6) was added to a plastic tube (Nunc Maxisorp Tube) and allowed to stand at 4° C. overnight. On the following day, the antigen solution was discarded, and the tube was then washed with 5 mL of PBS solution. This procedure was repeated 3 times. 5 ml of 5% BSA was then added, and the mixture was allowed to stand at 37° C. 2 hours later, the BSA solution was discarded and the tube was washed with 5 ml of PBS solution. Subsequently, 250 µL of the prepared phage solution was mixed with 750 µL of 5% BSA solution, the mixture was added to the tube, and then allowed to stand at 37° C. 1 hour later, the added solution was discarded and the tube was washed with 5 ml of PBST (0.1%) solution. This procedure was repeated 20 times. Subsequently, the tube was washed with 5 mL of PBS solution. This procedure was repeated 20 times. 1 mL of 100 mM triethylamine was added to the tube and the tube was allowed to stand at room temperature for 10 minutes. Thereafter, the triethylamine solution was collected, and 500 µL of 1M Tris-HCl (pH 7.5) was added thereto, followed by thorough mixing. 750 µL of this solution was added to 10 mL of *Escherichia coli* TG-1 which had been cultured until the absorbance at 600 nm became 0.6, and the mixture was allowed to stand at 37° C. for 30 minutes. Subsequently, the mixture was shaken at 37° C. at 200 rpm. 30 minutes later, the solution was centrifuged at 3,000 rpm for 10 minutes to collect *Escherichia coli*. This *Escherichia coli* was inoculated on the 2×TY plate medium (containing 100 µg/L ampicillin and 2% glucose) and incubated at 37° C. overnight. On the following day, phages were collected from *Escherichia coli* grown on the plate in accordance with the operation described in (Preparation of phage), and the operation described in (Screening operation) was repeated. This screening operation was repeated 3 times.

As a result, the antibodies ScFv1-1, ScFv1-2, ScFv1-3, and ScFv1-4 having amino acid sequences shown by SEQ ID NOS: 1 to 29 in the Sequence Listing were obtained.

SEQ ID NOS: 1 to 3 in the Sequence Listing represent amino acid sequences of CDR-1, CDR-2, and CDR-3 of the H chains of the antibodies ScFv1-1, ScFv1-2, ScFv1-3, and ScFv1-4.

SEQ ID NOS: 4 to 6 in the Sequence Listing represent amino acid sequences of CDR-1, CDR-2, and CDR-3 of the L chain of the antibody ScFv1-1.

SEQ ID NOS: 7 to 9 in the Sequence Listing represent amino acid sequences of CDR-1, CDR-2, and CDR-3 of the L chain of the antibody ScFv1-2.

SEQ ID NOS: 10 to 12 in the Sequence Listing represent amino acid sequences of CDR-1, CDR-2, and CDR-3 of the L chain of the antibody ScFv1-3.

SEQ ID NOS: 13 to 15 in the Sequence Listing represent amino acid sequences of CDR-1, CDR-2, and CDR-3 of the L chain of the antibody ScFv1-4.

SEQ ID NO: 16 in the Sequence Listing represents the amino acid sequence of the H chains of the antibodies ScFv1-1, ScFv1-2, ScFv1-3, and ScFv1-4.

SEQ ID NOS: 17 to 20 in the Sequence Listing respectively represent the amino acid sequences of the L chains of the antibodies ScFv1-1, ScFv1-2, ScFv1-3, and ScFv1-4.

SEQ ID NO: 21 in the Sequence Listing represents the nucleotide sequence of the H chains of the antibodies ScFv1-1, ScFv1-2, ScFv1-3, and ScFv1-4.

SEQ ID NOS: 22 to 25 in the Sequence Listing respectively represent the nucleotide sequences of the L chains of the antibodies ScFv1-1, ScFv1-2, ScFv1-3, and ScFv1-4.

SEQ ID NOS: 26 to 29 in the Sequence Listing respectively represent the nucleotide sequences and the amino acid sequences of the antibodies ScFv1-1, ScFv1-2, ScFv1-3, and ScFv1-4.

The antibodies ScFv2-1, ScFv2-2, ScFv2-3, and ScFv2-4 in which the amino acid sequence of the H chain was the amino acid sequence shown by SEQ ID NO: 34 in the Sequence Listing, were obtained.

SEQ ID NO: 34 in the Sequence Listing represents the amino acid sequence of the H chains of the antibodies ScFv2-1, ScFv2-2, ScFv2-3, and ScFv2-4.

SEQ ID NO: 35 in the Sequence Listing represents the nucleotide sequence of the H chains of the antibodies ScFv2-1, ScFv2-2, ScFv2-3, and ScFv2-4.

SEQ ID NOS: 36 to 39 in the Sequence Listing represent the nucleotide sequences and the amino acid sequences of the antibodies ScFv2-1, ScFv2-2, ScFv2-3, and ScFv2-4.

5. ScFv Rearrangement (Preparation of Antibody Library)

The antibody library was prepared in the same manner as described in the above section of "Preparation of antibody library".

At first, a vector was prepared in which the L chain region of PCantab5scFv3-1MycHis (wherein the scFv1-1 gene described in Example is inserted between the SfiI site and the NotI site of pCantab5MycHis, and Alw44I is provided at the 5'-terminus of the L chain and NotI site is provided at the 3'-terminus of the L chain) had been replaced with the HCV antigen-unreactive L chain. This was designated "pCantab5scFv3-1/L-/MycHis."

cDNA was synthesized from 1 µg of purified mRNA using RT-PCR kit ver 2.1 (TAKARA) in accordance with the attached information and using a random primer. In accordance with the information attached to this kit, L chain (λ chain, κ chain) of the antibody were then amplified by PCR using this cDNA as a template. The primer for cloning antibody genes was prepared and used in accordance with the description in the above literature. The PCR product was subjected to 1% agarose gel electrophoresis, and the bands of H chain and L chain of the antibody were cut out. From the agarose gel which was cut out, DNA was extracted using QIAEX II Gel extraction kit (QIAGEN).

Subsequently, the DNA was reacted with a restriction enzyme Alw44I in 50 µL of system M (10 mM Tris-HCl, 50 mM NaCl, 2 mM MgCl$_2$) at 37° C. for 2 hours and cleaved, and the enzyme was deactivated by heating at 70° C. for 10 minutes. The restriction enzyme NotI was further added, and the DNA was reacted in 100 µL of system H (10 mM Tris-HCl, 50 mM NaCl, 2 mM MgCl$_2$) at 37° C. for 2 hours and cleaved, and the enzyme was deactivated by heating at 70° C. for 10 minutes. The DNA was successively purified by phenol-chloroform extraction and ethanol precipitation and then dissolved in 50 µL of sterilized water. 100 ng of this DNA fragment and 50 ng of pCantab5scFv3-1/L-/MycHis which was treated with Alw44I and NotI in the same manner, were ligated to each other using a ligase kit (TAKARA) in accordance with the instructions. The ligation sample was successively purified by phenol-chloroform extraction and ethanol precipitation, and then dissolved in 10 µL of sterilized water. A half aliquot thereof was used to perform transformation in accordance with Molecular Cloning (1982) p249, Cold Spring Harbor Labs. Thus, 1×10$^6$ colonies were obtained. The resultant colonies were hereinafter used as a single-chain antibody library.

(Screening of Library Phage)

Preparation of phages and screening operations were performed in the same manner as described above.

As a result, the antibodies ScFv3-1, ScFv3-2, ScFv3-3, and ScFv3-4 having amino acid sequences shown by SEQ ID NOS: 42 to 65 in the Sequence Listing were obtained.

SEQ ID NOS: 42 to 44 in the Sequence Listing represent amino acid sequences of CDR-1, CDR-2, and CDR-3 of the L chain of the antibody ScFv3-1.

SEQ ID NOS: 45 to 47 in the Sequence Listing represent amino acid sequences of CDR-1, CDR-2, and CDR-3 of the L chain of the antibody ScFv3-2.

SEQ ID NOS: 48 to 50 in the Sequence Listing represent amino acid sequences of CDR-1, CDR-2, and CDR-3 of the L chain of the antibody ScFv3-3.

SEQ ID NOS: 51 to 53 in the Sequence Listing represent amino acid sequences of CDR-1, CDR-2, and CDR-3 of the L chain of the antibody ScFv3-4.

SEQ ID NOS: 54 to 57 in the Sequence Listing respectively represent amino acid sequences of the L chains of the antibodies ScFv3-1, ScFv3-2, ScFv3-3, and ScFv3-4.

SEQ ID NOS: 58 to 61 in the Sequence Listing respectively represent nucleotide sequences of the L chains of the antibodies ScFv3-1, ScFv3-2, ScFv3-3, and ScFv3-4.

SEQ ID NOS: 62 to 65 in the Sequence Listing respectively represent nucleotide sequences and amino acid sequences of the antibodies ScFv3-1, ScFv3-2, ScFv3-3, and ScFv3-4.

6. Preparation of scFv from Screened Phages

A candidate colony was inoculated on 100 mL of 2×TY liquid medium (containing 100 µg/L ampicillin and 2% glucose), and the colony was cultured at 30° C. at 200 rpm overnight. On the following day, the culture solution was added to 900 ml of 2×TY liquid medium (containing 100 µg/L ampicillin and 0.1% glucose), and cultured for 1 hour at 30° C. at 200 rpm. 1 mL of 1M IPTG (isopropyl-β-D-thio-galactopyranoside) was added, and the mixture was further cultured under the same condition for 5 hours. The culture solution was centrifuged at 8,000 rpm for 10 minutes to precipitate bacteria. The supernatant was discarded, the precipitate was suspended in 50 ml of 50 mM Tris-HCl (pH 8), 20% sucrose and 1 mM EDTA solution, and then allowed to stand in ice for 15 minutes. Subsequently, the suspension was centrifuged at 10,000 rpm for 15 minutes, the supernatant was collected, and $MgCl_2$ was added to bring the solution to 1 mM.

7. Purification of ScFv

ScFv obtained from the *Escherichia coli* was purified using Ni-NTA agarose (purchased from QIAGEN) in accordance with the instructions. 1 mL of Ni-NTA agarose was washed by adding 30 ml of solution A (50 mM Na-phosphate, 300 mM NaCl, pH 7.4), stirred and centrifuged at 1,000 rpm for 2 minutes, and the supernatant was then discarded. The above-described supernatant was added to the Ni-NTA agarose. The mixture was stirred for 45 minutes at 4° C., and His tag site of ScFv was bound to Ni-NTA agarose. Thereafter, the product was centrifuged at 1,000 rpm for 2 minutes, and the supernatant was discarded. 30 ml of solution A was added to wash Ni-NTA agarose, the mixture was centrifuged at 1,000 rpm for 2 minutes, and the supernatant was discarded. Further, Ni-NTA agarose was washed with 30 ml of solution B (solution A+10 mM imidazole) in the same manner. The Ni-NTA agarose was then suspended in 10 ml of solution B, and the suspension was added to poly-prep column (Bio-Rad). Further, 10 ml of solution B was added, and the Ni-NTA agarose was washed. After the washing buffer was completely removed from the column, ScFv bound to Ni-NTA agarose was eluted using 2 ml of solution C (solution A+250 mM imidazole). Subsequently, the eluate was added to PD10 column (Amersham Pharmacia) washed with 25 ml of PBS (10 mM phosphate pH 7.4, 150 mM NaCl), eluted with a PBS solution, and buffers were exchanged. The absorbance at 280 nm of each elution fraction was measured, and the ScFv elution fractions was taken together into one solution, and used in the later experiments.

8. Confirmation of Binding Ability Between ScFv and E2

1 mL of E2tag (1 µg/ml) dissolved in a 50 mM $NaHCO_3$ (pH 9.6) solution was added to 96-well plates (FALCON) in an amount of 50 µL respectively, and was incubated at 37° C. for 1 hour. At this time, the same number of wells containing a buffer only and no E2tag, were also prepared as blank wells. The solution in each well was discarded by decantation, and 200 µL of PBS containing 0.1% Tween 20 was added to each well, followed by discard by decantation. This procedure was repeated 5 times. After the water content in each well was removed, PBS solution containing 5% BSA was added to each well in an amount of 200 µL, and the mixture was incubated at 37° C. for 1 hour. The solution in each well was discarded by decantation, and 200 µL of PBS containing 0.1% Tween 20 was added to each well, followed by discard by decantation. This procedure was repeated 5 times. The obtained scFv was diluted with PBS containing 1% BSA to bring the concentration to 10 µg/mL or below and added to each of the wells with E2tag and the wells without E2tag in amounts of 50 µL each, and was incubated at 37° C. for 1 hour. The solution in each well was discarded by decantation, and 200 µL of PBS containing 0.1% Tween 20 was added to each well, followed by discard by decantation. This procedure was repeated 5 times. After the water content in each well was removed, the anti-myc-tag antibody (purchased from Santa Cruz Biotechnology, Inc.) was diluted with PBS containing 1% BSA so as to bring the final concentration to 10 µg/mL, added to each well in amounts of 50 µL each, and the mixture was incubated at 37° C. for 1 hour. The solution in each well was discarded by decantation, and 200 µL of PBS containing 0.1% Tween 20 was added to each well, followed by discard by decantation. This procedure was repeated 5 times. HRP-labeled anti-mouse Igs was diluted with PBS containing 1% BSA so as to bring the final concentration to 1 µg/mL, added to each well in amounts of 50 µL each, and the mixture was incubated at room temperature for 1 hour. The solution in each well was discarded by decantation, and 200 µL of PBS containing 0.1% Tween 20 was added to each well, followed by discard by decantation. This procedure was repeated 5 times. A solution of 10 mg of orthophenylenediamine and 12.5 µL of 30% hydrogen peroxide solution in 25 mL of OPD buffer was added to each well in amounts of 100 µL each, and the mixture was incubated at room temperature until color sufficiently developed. 100 µL of 4N sulfuric acid was added to terminate the reaction, and the absorbance at 490 nm was measured to confirm whether or not scFv bound to E2tag.

9. Construction of Antibody Expression Vector

A region containing CMV promoter of pRC/CMV (purchased from Invitrogen), a multi-cloning site, a poly(A) signal sequence region (nucleotide 209 to 1250 in the gene map of Invitrogen) were amplified by PCR. The sequences of the used primers are 5'CCC TGA TCA GAA TTC GCA GGA TCC CTC GAG ACT AGT GAT GAT CGG GCC AGA TAT ACG CG 3' (SEQ ID NO: 66) for the 5'-side and 5'CCC TGA TCA AGA TCT GCT AGC GTC GAC TCC CCA GCA TGC CTG CTG CTA TTG 3' (SEQ ID NO: 67) for the 3'-side. The primers were synthesized using Applied Biosystems Model 394 and then prepared by a conventional method. PCR was performed using Perkin Elmer Cetus DNA Thermal Cycler and KOD polymerase (purchased from Toyobo Co., Ltd., the reaction conditions were set in accordance with the instructions). Thereafter, the desired about 1.0 Kbp DNA fragment was purified by 5% acrylamide electrophoresis in accordance with the method described in Molecular Cloning, sections 6.46–6.48, Cold Spring Harbor. About 1 µg of purified DNA fragment was reacted in 50 µl of system H using 1 unit of BclI at 37° C. for 2 hours and cleaved. Separately, 1 µg of ppUC119 (purchased from Takara Shuzo Co., Ltd.) DNA was reacted using 1 unit of BamHI in 50 µl of system H at 37° C. for 2 hours and cleaved. The cleaved DNA fragment and the cleaved plasmid were ligated to each other using a ligase kit (purchased from Takara Shuzo Co., Ltd., the reaction was carried out in accordance with the instructions), *Escherichia coli* strain JM109 (purchased from Takara Shuzo Co., Ltd., the reaction was carried out in accordance with the instructions) was transformed, and the desired expression plasmid pKS1 was obtained.

The above-obtained pKS1 (1 µg) was reacted using 1 unit of SpeI in 50 µl of system M at 37° C. for 2 hours and cleaved.

The loxP-Hygromycin fused gene was amplified by PCR using pcDNA3.1/Hygro(+) (purchased from Invitrogen). The sequences of the used primers were Hyg-stop: ccccagatctctattcctttgccctcggacgag (SEQ ID NO: 68) for the 5'-side and Hy-atg: ccccaagcttatgaaaaagcctgaactcaccgcg 3' (SEQ ID NO: 69) for the 3'-side. The synthesis was ordered to SciMedia Ltd. and purchased therefrom. PCR was performed using Perkin Elmer Cetus DNA Thermal Cycler and KOD polymerase (purchased from Toyobo Co., Ltd., the reaction conditions were set in accordance with the instructions). Thereafter, the desired DNA fragment was purified by 5% acrylamide electrophoresis in accordance with the method described in Molecular Cloning, sections 6.46–6.48, Cold Spring Harbor. About 1 µg of purified DNA fragment was reacted in 50 µl of system M using 1 unit of NheI and NaeI at 37° C. for 2 hours and cleaved.

DNA containing TK(A)n was amplified by PCR using pNeo•gal (purchased from Stratagene). The sequences of the used primers were cccgccggctgggtgtggcggaccgc3' (SEQ ID NO: 70) for the 5'-side and 5' ccctctagaaagtataggaacttcaagc 3' (SEQ ID NO: 71) for the 3'-side. The primers were synthesized using Applied Biosystems Model 394 and then prepared by a conventional method. PCR reaction was performed using Perkin Elmer Cetus DNA Thermal Cycler and KOD polymerase (purchased from Toyobo Co., Ltd., the reaction conditions were set in accordance with the instructions). Thereafter, a desired DNA fragment was purified by 5% acrylamide electrophoresis in accordance with the method described in Molecular Cloning, Section 6.46–6.48, Cold Spring Harbor. About 1 µg of purified DNA fragment was reacted in 50 µL of system M using 1 unit of XbaI and NaeI at 37° C. for 2 hours and cleaved.

The cleaved plasmid, the cleaved loxP-hygromycin DNA fragment, and the Tk(A)nDNA fragment were ligated to each other using a ligase kit (purchased from Takara Shuzo Co., Ltd., the reaction was carried out in accordance with the instructions), *Escherichia coli* strain JM109 (purchased from Takara Shuzo Co., Ltd., the reaction was carried out in accordance with the instructions) was transformed, and the desired expression plasmid, pEX loxP-Hyg was obtained.

A DNA fragment containing a heavy chain constant region was amplified by PCR using pEX1-3-1W (Japanese Patent Application No. 2000-1726984 which is published as International Publication No. WO 01/94571). The sequences of the used primers were 5'ccccaagcttctcgagactagtaccaagggcccatcggtcttccc3'(SEQ ID NO: 72) for the 5'-side and 5'ccccgggccctctagtagctttcatttacccggagacaggg3'(SEQ ID NO: 73) for the 3'-side. The synthesis was ordered to SciMedia Ltd. and purchased therefrom. PCR reaction was performed using Perkin Elmer Cetus DNA Thermal Cycler and KOD Polymerase (purchased from Toyobo Co., Ltd., the reaction conditions were set in accordance with the instructions). Thereafter, the desired DNA fragment was purified by 5% acrylamide electrophoresis in accordance with the method described in Molecular Cloning, sections 6.46–6.48, Cold Spring Harbor. About 1 µg of purified DNA fragment was reacted in 50 µl of system M using 1 unit of HindIII and ApaI at 37° C. for 2 hours and cleaved.

1 µg of pEX loxP-Hyg DNA was reacted using 1 unit of HindIII and ApaI in 50 µl of system M at 37° C. for 2 hours and cleaved.

The cleaved plasmid and the cleaved DNA fragment containing a heavy chain constant region were ligated to each other using a ligase kit (purchased from Takara Shuzo Co., Ltd., the reaction was carried out in accordance with the instructions), *Escherichia coli* strain JM109 (purchased from Takara Shuzo Co., Ltd., the reaction was carried out in accordance with the instructions) was transformed, and the desired expression plasmid, pEX gamma1 loxP-Hyg, was obtained.

A DNA fragment containing a heavy chain variable region was amplified by PCR using ScFv1-1. The sequences of the used primers were HB1-N 5' cccaagcttcaccATGAAACACCTGTGGTTCTTCCTCCTGCTGGTGGCAGCTCCCAGATGGGTCCTGTCCCAGGTGCAGCtggtgcagtctg3' (SEQ ID NO: 74) and HB1-C 5' cccgctagcACTCGAGACGGTGACCAGGGTGCC3' (SEQ ID NO: 75). The synthesis was ordered to SciMedia Ltd. and purchased therefrom. PCR reaction was performed using Perkin Elmer Cetus DNA Thermal Cycler and KOD polymerase (purchased from Toyobo Co., Ltd., the reaction conditions were set in accordance with the instructions). Thereafter, the desired DNA fragment was purified by 5% acrylamide electrophoresis in accordance with the method described in Molecular Cloning, sections 6.46–6.48, Cold Spring Harbor. About 1 µg of purified DNA fragment was reacted in 50 µl of system M using 1 unit of HindIII and NheI at 37° C. for 2 hours and cleaved.

1 µg of pEX gamma1 loxP-Hyg DNA was reacted using 1 unit of HindIII and SpeI in 50 µl of system M at 37° C. for 2 hours.

Figure 7:
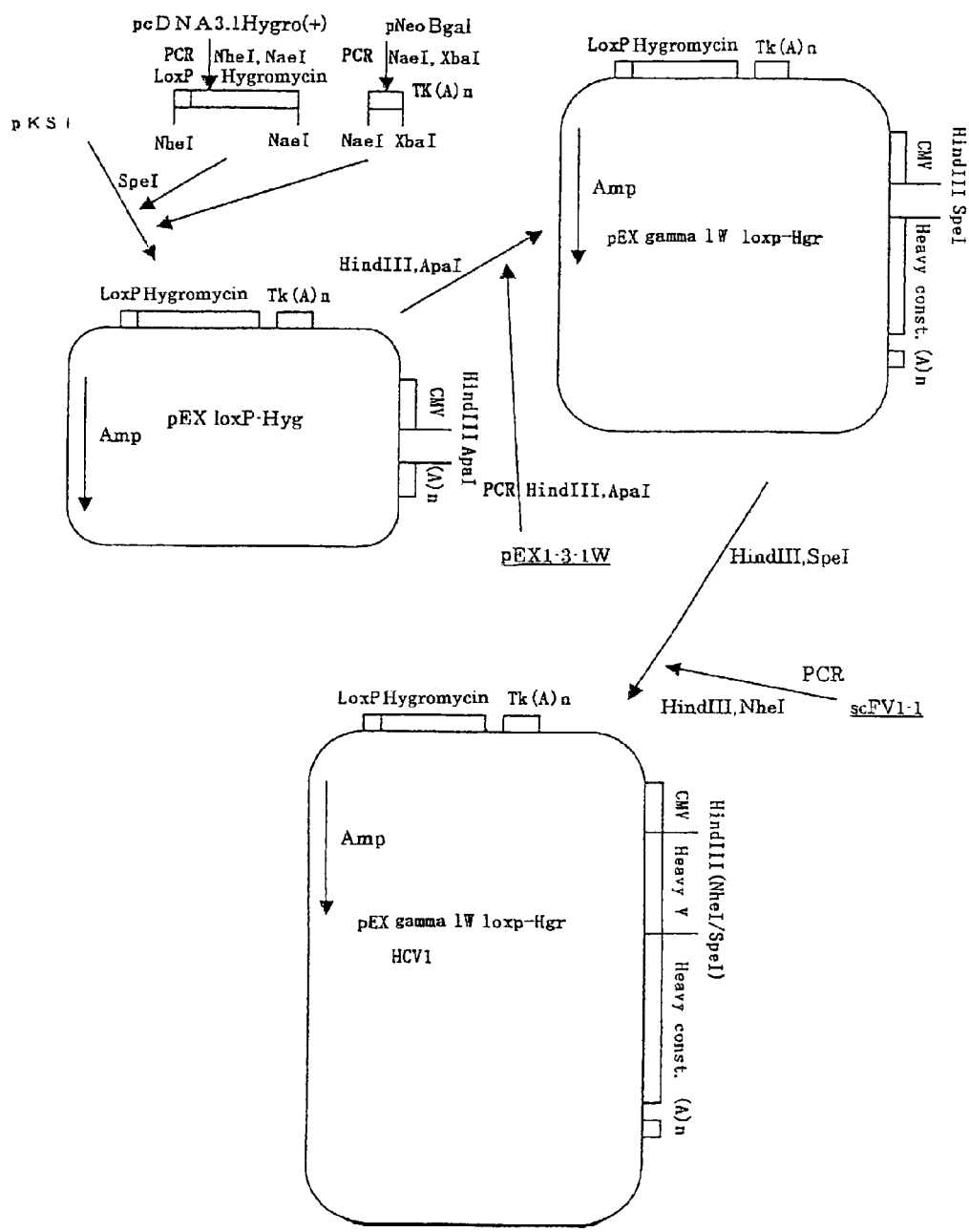
FIG. 7 is a diagram showing a construction of an expression plasmid, pEX gamma1 loxP-Hyg HCVI.

The cleaved plasmid and the cleaved DNA fragment containing a heavy chain variable region were ligated to each other using a ligase kit (purchased from Takara Shuzo Co., Ltd., the reaction was carried out in accordance with the instructions), *Escherichia coli* strain JM109 (purchased from Takara Shuzo Co., Ltd., the reaction was carried out in accordance with the instructions) was transformed, and the desired expression plasmid, pEX gamma1 loxP-Hyg HCV1 was obtained (FIG. 7).

A DNA fragment containing kanamycin-resistant genes was amplified by PCR using pEGFPN2 (purchased from Clonetech). The sequences of the used primers were 5'ccccagagctagtcctgcaggcggggaaatgtgcgcggaacccct3' (SEQ ID NO: 76) for the 5'-side of the H chain and 5'ccccgctagcctgcaagtcatttcgaaccccagcgtccc3' (SEQ ID NO: 77) for the 3'-side. The synthesis was ordered to SciMedia Ltd. and purchased therefrom. PCR reaction was performed using Perkin Elmer Cetus DNA Thermal Cycler and KOD polymerase (purchased from Toyobo Co., Ltd., the reaction conditions were set in accordance with the instruction). Thereafter, the desired DNA fragment was purified by 5% acrylamide electrophoresis in accordance with the method described in Molecular Cloning, sections 6.46–6.48, Cold Spring Harbor. About 1 µg of purified DNA fragment was reacted in 50 µl of system M using 1 unit of SpeI and NheI at 37° C. for 2 hours, and then reacted at 37° C. for 2 hours to be cleaved.

1 µg of pKS1 DNA was reacted using 1 unit of NheI in 50 µl of system M at 37° C. for 2 hours.

The cleaved plasmid and the cleaved DNA fragment containing kanamycin-resistant genes were ligated to each other using a ligase kit (purchased from Takara Shuzo Co., Ltd., the reaction was carried out in accordance with the instructions), *Escherichia coli* strain JM109 (purchased from Takara Shuzo Co., Ltd., the reaction was carried out in accordance with the instructions) was transformed, and the desired expression plasmid, pEX-1 Km, Amp, was obtained.

1 µg of pEX-1 Km, Amp 1 DNA was reacted using 1 unit of DraI and ScaI in 50 µl of system H at 37° C. for 2 hours and cleaved.

The cleaved plasmid was ligated using a ligase kit (purchased from Takara Shuzo Co., Ltd., the reaction was carried out in accordance with the instructions), *Escherichia coli* strain JM109 (purchased from Takara Shuzo Co., Ltd., the reaction was carried out in accordance with the instructions) was transformed, and the desired expression plasmid, pEX-1 Km, was obtained.

A DNA fragment containing a light chain constant region was amplified by PCR using pCZ0k (described in Shibui, T., et al., Appl. Microbiol. Biotechnol. (1993) 38, 770–775). The sequences of the used primers were 5'cccccaagcttcta-gagtcgacggtaccgtggaaatcaaacgaactgtgg3' (SEQ ID NO: 78) for the 5'-side of the H chain and 5'ccccgggccctctagcggc-cgcctaacactctcccctgttgaagc3' (SEQ ID NO: 79) for the 3'-side. The synthesis was ordered to SciMedia Ltd. and purchased therefrom. PCR reaction was performed using Perkin Elmer Cetus DNA Thermal Cycler and KOD polymerase (purchased from Toyobo Co., Ltd., the reaction conditions were set in accordance with the instructions). Thereafter, the desired DNA fragment was purified by 5% acrylamide electrophoresis in accordance with the method described in Molecular Cloning, sections 6.46–6.48, Cold Spring Harbor. About 1 µg of purified DNA fragment was reacted in 50 µl of system M using 1 unit of HindIII and ApaI at 37° C. for 2 hours and cleaved.

1 µg of pEX-1 Km DNA was reacted using 1 unit of HindIII and ApaI in 50 µl of system M at 37° C. for 2 hours and cleaved.

The cleaved plasmid and the cleaved DNA fragment containing a light chain constant region were ligated to each other using a ligase kit (purchased from Takara Shuzo Co., Ltd., the reaction was set in accordance with the instructions), *Escherichia coli* strain JM109 (purchased from Takara Shuzo Co., Ltd., the reaction was carried out in accordance with the instructions) was transformed, and the desired expression plasmid, pEX kappa Km, was obtained.

A DNA fragment containing a light chain variable region was amplified by PCR using scFv1-1. The sequences of the used primers were LK1-N 5'cccaagcttcaccATGGCGTTG-CAGACCCAGGTCTTCATTTCTCTGTTGCTCTGG ATCTCTGGTGCCTACGGGgacatccagatgacccagtcc3' (SEQ ID NO: 80) and LK1-C 5' CcccgtacgTTTGATTTC-CACCTTGGTCCCCCCG3' (SEQ ID NO: 81). The synthesis was ordered to SciMedia Ltd. and purchased therefrom. PCR reaction was performed using Perkin Elmer Cetus DNA Thermal Cycler and KOD polymerase (purchased from Toyobo Co., Ltd., the reaction conditions were set in accordance with the instructions). Thereafter, the desired DNA fragment was purified by 5% acrylamide electrophoresis in accordance with the method described in Molecular Cloning, sections 6.46–6.48, Cold Spring Harbor. About 1 µg of purified DNA fragment was reacted in 50 µl of system M using 1 unit of HindIII and BsiWI at 37° C. for 2 hours, and reacted at 50° C. for 2 hours to be cleaved.

1 µg of pEX kappa Km DNA was reacted using 1 unit of HindIII and Asp187I in 50 µl of system M at 37° C. for 2 hours and cleaved.

Figure 8:
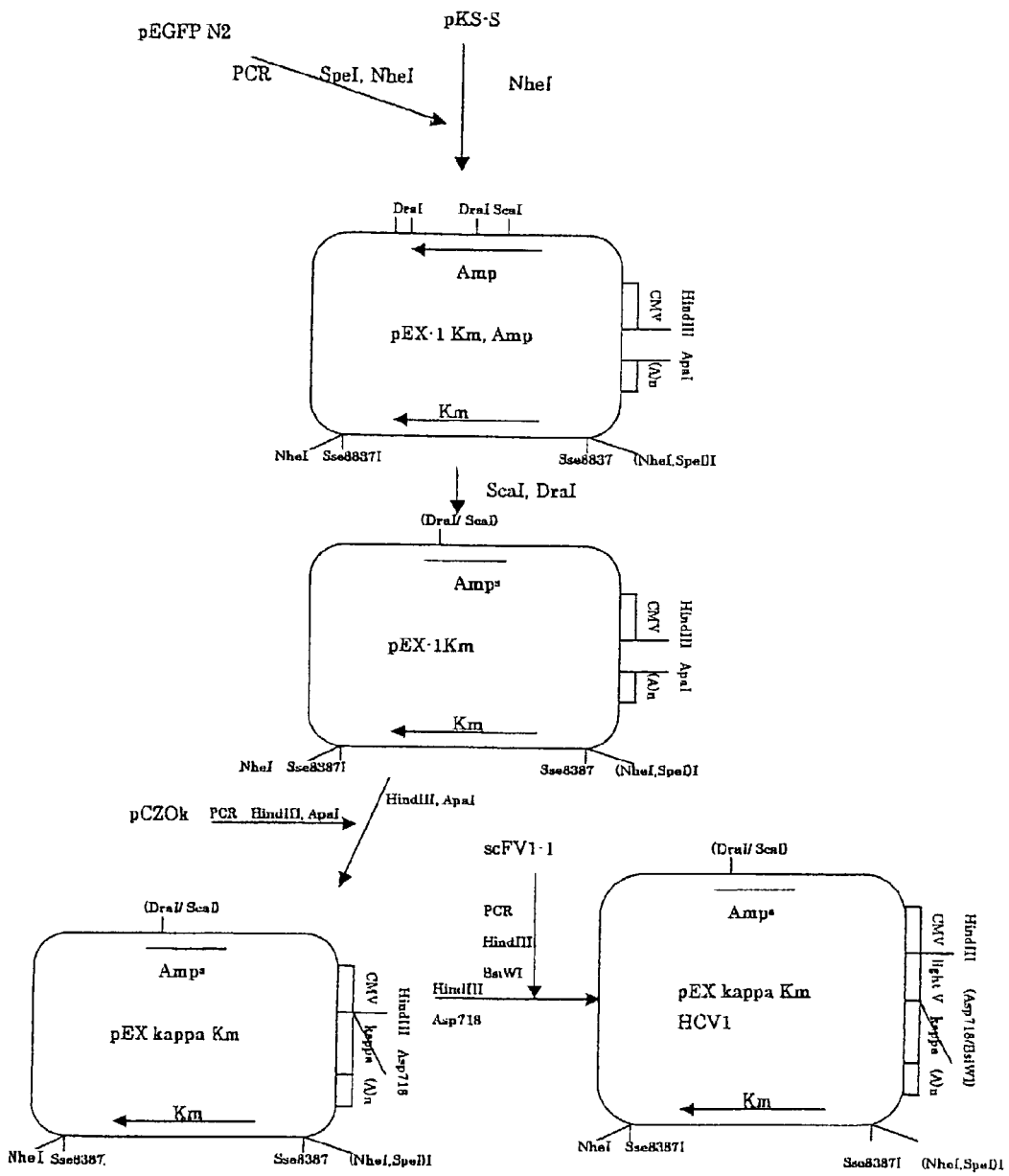
FIG. 8 is a diagram showing a construction of an expression plasmid, pEX kappa Km HCVI.

The cleaved plasmid and the cleaved DNA fragment containing a heavy chain variable region were ligated to each other using a ligase kit (purchased from Takara Shuzo Co., Ltd., the reaction was carried out in accordance with the instructions), *Escherichia coli* strain JM109 (purchased from Takara Shuzo Co., Ltd., the reaction was carried out in accordance with the instruction) was transformed, and the desired expression plasmid, pEX kappa Km HCVI, was obtained (FIG. 8).

1 µg of pEX kappa Km HCV1 DNA was reacted using 1 unit of SpeI and NheI in 50 µl of system M at 37° C. for 2 hours and cleaved.

1 µg of pEX gamma1 loxP-Hyg HCV1 DNA was reacted using 1 unit of NheI in 50 µl of system M at 37° C. for 2 hours and cleaved.

The above described cleaved plasmids were ligated to each other using a ligase kit (purchased from Takara Shuzo Co., Ltd., the reaction was carried out in accordance with the instructions), *Escherichia coli* strain JM109 (purchased from Takara Shuzo Co., Ltd., the reaction was carried out in accordance with the instructions) was transformed, and the desired plasmid, pEX loxp-Hyg HCV1 W Km, was obtained.

1 µg of pEX loxp-Hyg HCV1 W Km 1 DNA was reacted using 1 unit of Sse8387 in 50 µl of system M at 37° C. for 2 hours and cleaved.

Figure 9:
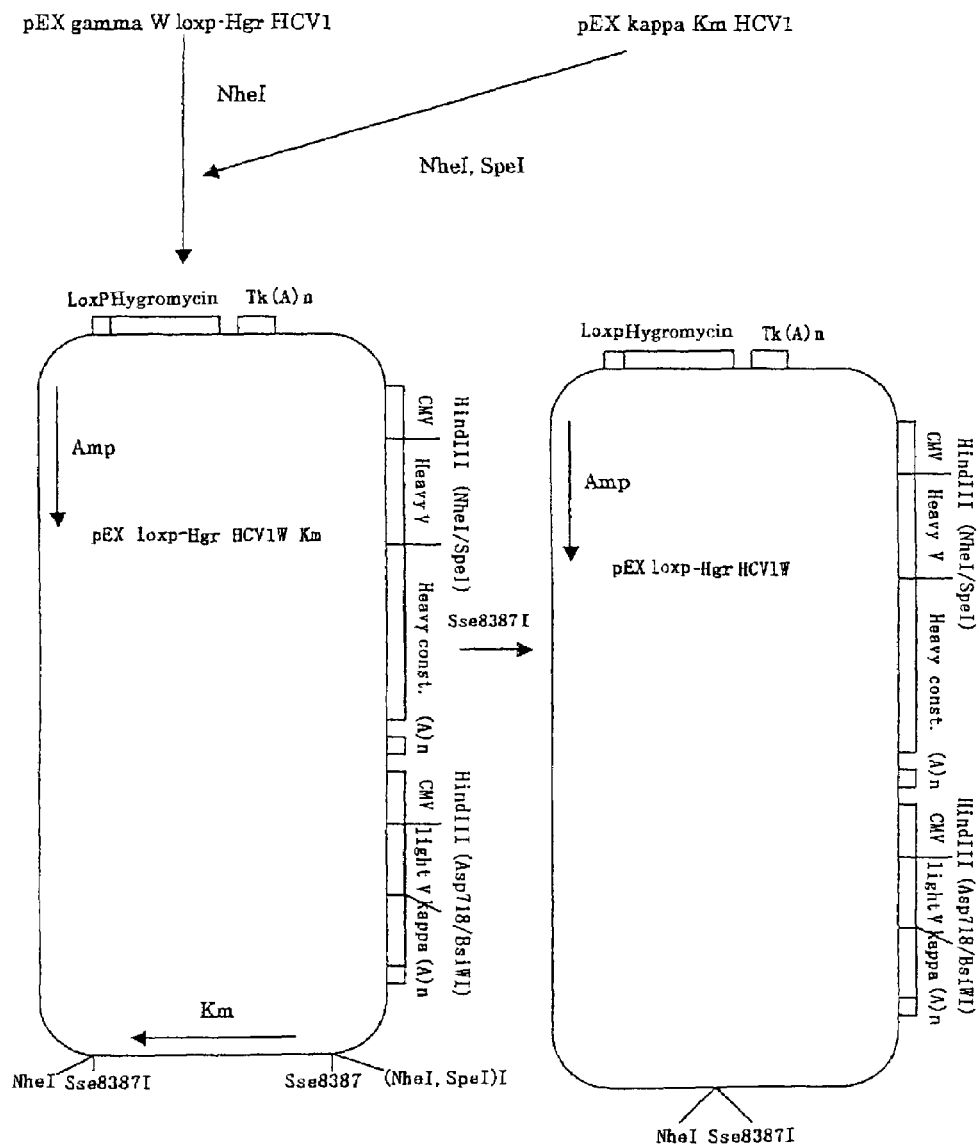
FIG. 9 is a diagram showing a construction of an expression plasmid, pEX loxp-Hyg HCV1 W.

The cleaved plasmid was ligated using a ligase kit (purchased from Takara Shuzo Co., Ltd., the reaction was carried out in accordance with the instructions), *Escherichia coli* strain JM109 (purchased from Takara Shuzo Co., Ltd., the reaction was carried out in accordance with the instructions) was transformed, and the desired expression plasmid, pEX loxp-Hyg HCV1 W, was obtained (FIG. 9).

10. Site-specific Introduction of Antibody Gene into the High Expression Site Searching Strain pBS185 (site-specific recombinant enzyme expression plasmid, purchased from Lifetech) and pEX loxp-Hyg HCV1 W were transfected (1.0 µg each of DNA was used for 2,000,000 cells) using strain MKamp1 (strain described in Japanese Patent Application No. 2000-172684 which is published as International Publication No. WO 01/94571) in accordance with the instructions. The cells were cultured in the CHO-S-SFM-II medium containing 5% FBS (fetal bovine serum, purchased from Lifetech) at 37° C. under 5% $CO_2$ for 48 hours. Then, the cells were selectively cultured in the same medium supplemented with 200 mg/l hygromycin (purchased from SIGMA) at 37° C. under 5% $CO_2$ for 25 days, and a hygromycin-resistant colony was selected (strain MkampHCV1).

11. Measurement of Production Amount of Antibody Using ELISA Assay

A solution of anti-human immunoglobulin goat antibody (diluted to 10 µg/ml with solution 1; purchased from Zymed) was added to a 96-well plate at 50 µl/well, and the plate was treated at 37° C. for 2 hours. Thereafter, the solution in the well was discarded, 250 µl of solution 2 was added to each well, and incubated at 4° C. for 16 hours or longer. After the solution was removed, each well was washed with solution 3 five times. An antibody (standard) diluted with solution 4 or a sample solution (a culture supernatant was optionally diluted with solution 4) was added at 50 µl/well, and incubated at 37° C. for 2 hours. After the removal of the solution and washing with solution 3 five times, solution 5 was added at 50 µl/well, and the mixture was incubated at 20° C. for 40 minutes. After the removal of the solution and washing with PBS five times, solution 9 was added at 100 µl/well, and reaction was performed at room temperature under a shaded condition for about 5 minutes. An equal amount of 10% sulfuric acid was added to terminate the reaction, the absorbance A1 and A2 at 11=490 nm and 12=650 nm in each well were then measured using an immunoreader (manufactured by Inter Med, Immuno Reader NJ-2000) to determine (A1-A2). A calibration curve was prepared using a diluted standard solution to measure the concentration of the 1-3-1 antibody (used as a standard) in the sample.

Formulation of each solution is as follows.

Solution 1: PBS containing 0.1% sodium azide

Solution 2: PBS containing 1% BSA and 0.1% sodium azide

Solution 3: PBS containing 0.05% Tween 20

Solution 4: PBS containing 1% BSA

Solution 5: a solution of 2 µl of stock solution of HRP-labeled anti-human immunoglobulin goat antibody (purchased from Zymed) in 10 ml of solution 4 (prepared at the time of using)

Solution 6: 500 ml of solution prepared by adding water to 14.2 g of sodium hydrogenphosphate Solution 7: 500 ml of solution prepared by adding water to 10.5 g of citric monohydrate Solution 8: 1,000 ml of solution prepared by adding water to the mixture of 257 ml of solution 5 and 243 ml of solution 6 Solution 9: a solution prepared by dissolving 4.0 mg of O-phenylenediamine (purchased from Wako Pure Chemicals Industries, Ltd.) in 10 ml of solution 7 and 5 µl of 30% (v/v) hydrogen peroxide solution (used within 10 minutes after preparation)

12. Antibody Productivity of the Strain Prepared by Site-specifically Introducing an Antibody Expression Gene into Strain MKamp The following production amount was observed by the above ELISA assay.

| Parent strain | Flour-escence | Antibody gene-introduced strain Hygromycin-resistance | Antibody productivity |
|---|---|---|---|
| Mkamp 1 | None | Resistant | 10 mg/l |

13. Characterization of Recombinant Whole Antibody

In the same manner as employed in the assay of the affinity and the neutralizing activity against the antigen of a single-chain antibody, the values were measured for the obtained and purified recombinant whole antibody.

$Kd=2\times10^{-9}$ neutralizing activity $IC_{50}=25$ mg/l

The obtained recombinant whole antibody was designated "whole antibody 1–1" and the amino acid sequence and the nucleotide sequence of the heavy chain and the light chain are shown in SEQ ID NOS: 40 and 41 in the Sequence Listing.

14. Cell Fusion Assay

Cell fusion assay was performed in accordance with the method of Takikawa et al. (Takikawa et al., J. Virol., 74, 5066–5074, 2000). 20,000 CHO cells (Matsuura et al., unpublished) expressing recombinant E1 and E2 proteins on cell surfaces were respectively inoculated in each well on a collagen-coated 96-well plate and cultured under 5% $CO_2$ at 37° C. In the preparation of cells, without using trypsin, the cells were immersed in 10 mM EDTA-added phosphate buffer saline (PBS) for 5 minutes, a flask was shaken to disperse the cells as much as possible, and the cells were detouched while slowly pipetting. After culturing for 24 hours, the cells were washed with 200 µL of Opti-MEM (Gibco BRL) twice. Then, a reporter plasmid pT7EMCLuc (Aoki et al., Virology, 250, 140–150, 1998) having a firefly luciferase gene incorporated downstream of T7 promoter and pRL-CMV (Promega) having a sea pansy luciferase gene incorporated downstream of CMV promoter for standardizing the gene-introducing efficiency were introduced into cells using Trans IT-LT1 (Mirus). The medium was prepared in the following formulation for each plate. After the media were allowed to stand for 15 minutes, 30 µL each thereof was added to each well. 2 hours later, 150 µl of D-MEM (Gibco) supplemented with 10% serum was added, and culturing is continued.

| | |
|---|---|
| Opti-MEM | 3 ml |
| Trans IT-LT1 | 50 µL |
| pT7EMCLuc | 9 µg |
| pRL-CMV | 0.6 µg |

HepG2 cells derived from human hepatocellular cancer were used as receptor cells for cell fusion. HepG2 cells were inoculated in each well on a 6-well plate at $8.0\times10^5$ cells and cultured under 5% $CO_2$ at 37° C. After culturing for 24 hours, plasmid pCAGT7pol (Ishii et al., unpublished) expressing T7 RNA polymerase was introduced into the cell in the following formulation per well, and 2 hours later, 1.5 ml of D-MEM supplemented with 10% serum was added. After culturing for 24 to 36 hours, cells were trypsinized, suspended in 25 to 30 ml of D-MEM supplemented with 10% serum, transferred to 50 ml centrifugation tube, and the suspension culturing was performed under 5% $CO_2$ at 37° C. on a shaking apparatus overnight.

| | |
|---|---|
| Opti-MEM | 100 µL |
| Trans IT-LT11 | 5 µL |
| pCAGT7pol | 1 µg |

On the CHO cells (48 hours after transfection) which was provided on the 96-well plate, had a reporter plasmid introduced therein and expressed an HCV envelope protein, were added $2\times10^4$ cells/100 µL per well of HepG2 cells which had a plasmid expressing T7RNA polymerase introduced therein and was subjected to suspension culture overnight. After culturing for 5 hours, the medium was discarded and the cells were immersed in 100 µL of PBS (pH 5.0) for 2 minutes. Immediately after that, the solution was discarded, and 200 µL of D-MEM supplemented with 10% serum was added to each well, and culturing was continued. After culturing for 5 hours, the cells were assayed for the luciferase activity using dual-luciferase reporter assay system (Promega) in accordance with the attached protocol. Thus, the cell fusion activity was evaluated.

15. Cell Fusion Inhibition Assay

The assay of the cell fusion inhibitory activity by the antibody was performed in basically the same manner as in the above cell fusion assay except that, before the addition of HepG2 cells to the CHO cells, HepG2 cells were washed with Opti-MEM twice, reacted with the test antibody (whole antibody 1-1) which was stepwisely diluted with Opti-MEM for 60 minutes, and then co-culture was performed. Thereafter, the luciferase activity was measured in the same manner, and the cell fusion inhibitory activity was evaluated. As a result, a substance which specifically inhibits the cell fusion by the envelope protein of HCV was observed in the complete antibodies which were prepared based on the single-chain antibody which exhibited the NOB activity.

16. Measurement of Binding Constant using BIACORE X

The binding constant of the obtained ScFv was measured using BIACORE X in accordance with the attached instructions.

E2tag was substituted with 10 mM acetate buffer (pH=5.0) using Centricon 30. This E2tag (100 μg/mL, 20 μL) was injected into separate lanes on sensor chip CM5 (purchased from BIACORE) at 5 μL/min to be immobilized by amino binding. Thus, an E2tag immobilized sensor chip was obtained. ScFv1-1 was substituted with HBS buffer (10 mM HEPES (pH 7.4), 0.15 M NaCl, 3.4 mM EDTA, 0.005% Tween 20) using Centricon 30. This scFv1-1 solution was injected onto the previously prepared E2tag sensor chip using BIACORE X (BIACORE) at 5 μL/min to obtain a sensorgram at the time of binding. Thereafter, only the HBS solution was injected onto the sensor chip at 5 μL/min to obtain a sensorgram at the time of dissociation. By analysis of these sensorgrams, a binding constant of $4.5 \times 10^8$ (M) and a dissociation constant of $2.2 \times 10^{-9}$ (M) between E2tag and scFv1-1 were obtained.

17. Confirmation of Binding Between E2tag and Heparin

As a method for confirming the presence of the site in E2tag for binding with sulfated polysaccharide, the binding between a column Heparin-Sepharose CL-6B (purchased from Pharmacia) to which heparin is covalently bound and E2tag was confirmed. Heparin-Sepharose CL-6B was equilibrated using 0.15 M NaCl, 10 mM phosphate buffer (pH 7.0).

2 μg of E2tag dissolved in PBS and 300 μg of high molecular weight heparin (purchased from SIGMA) or 300 μg of Heparin (purchased from SIGMA) were mixed in 50 μL of system, and the mixture was incubated at 37° C. for 1 hour while stirring. As a control, a sample which was incubated with E2tag only was also prepared. Centrifugation was performed at 10,000 rpm for 5 minutes, and only the supernatant was fractionated into another container. 100 μL of 0.15 M NaCl, 10 mM phosphate buffer (pH 7.0) was added, and the mixture was centrifuged. The supernatant was then transferred to another container. This procedure was repeated 5 times. 50 μL of 0.5 M NaCl, 10 mM phosphate buffer (pH 7.0) was added, and the mixture was stirred at room temperature for 5 minutes and centrifuged. The supernatant was then transferred to another container. 50 μL of 1.5 M NaCl and 10 mM phosphate buffer (pH 7.0) was added, and the mixture was stirred at room temperature for 5 minutes and centrifuged. The supernatant was then transferred to another container. 50 μL of sample buffer was added, and the mixture was incubated at 100° C. for 5 minutes, centrifuged, and the supernatant was transferred to another container.

The elution samples transferred to the other containers were subjected to 10% polyacrylamide gel electrophoresis, and Western blotting was performed in the same manner as employed in the section regarding construction of E2tag expression strain, thereby confirming which of the elution fractions contained E2tag. As a result, it was found that E2tag was all bound to the column when only the E2tag was mixed with Heparin-Sepharose CL-6B, and it was confirmed that the binding of E2tag to the column was inhibited when incubated with high molecular weight heparin or heparin before mixing with Heparin-Sepharose CL-6B. These results indicate that E2tag and E2 have sites which strongly bind to heparin.

INDUSTRIAL APPLICABILITY

The present invention can provide a novel medicament which has an anti-viral effects such as an inhibitory action against HCV infection.

The invention claimed is:

1. An antibody comprising a heavy chain (H chain) having a variable region wherein CDR-1, CDR-2, and CDR-3 respectively comprise amino acid sequences shown by SEQ ID NOS: 1, 2, and 3.

2. The antibody of claim 1 which comprises an amino acid sequence shown by SEQ ID NO: 16 or 34.

3. A nucleic acid which encodes the antibody of claim 1.

4. A medicament composition which comprises the antibody of claim 1 as an active ingredient.

5. An anti-HCV composition which comprises the antibody of claim 1 as an active ingredient.

* * * * *

SEQUENCE LISTING

```
<160> NUMBER OF SEQ ID NOS: 81

<210> SEQ ID NO 1
<211> LENGTH: 5
<212> TYPE: PRT
<213> ORGANISM: Homo sapiens

<400> SEQUENCE: 1

Asp Gln Pro Ile Gly
1               5

<210> SEQ ID NO 2
<211> LENGTH: 16
<212> TYPE: PRT
<213> ORGANISM: Homo sapiens

<400> SEQUENCE: 2

Gly Ile Ile Pro Leu Ser Gly Pro Pro His Tyr Ala Gln Lys Phe Gln
1               5                   10                  15
```

```
<210> SEQ ID NO 3
<211> LENGTH: 16
<212> TYPE: PRT
<213> ORGANISM: Homo sapiens

<400> SEQUENCE: 3

Val Leu Arg Gly Tyr Cys Arg Arg Gly Ser Cys Tyr Asp Trp Leu Asp
1               5                   10                  15

<210> SEQ ID NO 4
<211> LENGTH: 11
<212> TYPE: PRT
<213> ORGANISM: Homo sapiens

<400> SEQUENCE: 4

Gln Ala Ser Gln Asp Ile Ser Asn Tyr Leu Asn
1               5                   10

<210> SEQ ID NO 5
<211> LENGTH: 7
<212> TYPE: PRT
<213> ORGANISM: Homo sapiens

<400> SEQUENCE: 5

Ala Thr Ser Arg Leu Tyr Ser
1               5

<210> SEQ ID NO 6
<211> LENGTH: 9
<212> TYPE: PRT
<213> ORGANISM: Homo sapiens

<400> SEQUENCE: 6

Gln Gln Thr Lys Ser Phe Pro Leu Thr
1               5

<210> SEQ ID NO 7
<211> LENGTH: 11
<212> TYPE: PRT
<213> ORGANISM: Homo sapiens

<400> SEQUENCE: 7

Arg Ala Ser Gln Asp Ile Ser Thr Trp Leu Ala
1               5                   10

<210> SEQ ID NO 8
<211> LENGTH: 7
<212> TYPE: PRT
<213> ORGANISM: Homo sapiens

<400> SEQUENCE: 8

Ala Ala Ser Ser Leu Gln Ser
1               5

<210> SEQ ID NO 9
<211> LENGTH: 9
<212> TYPE: PRT
<213> ORGANISM: Homo sapiens

<400> SEQUENCE: 9

Leu Gln His Asp Ser Tyr Pro Phe Ser
1               5

<210> SEQ ID NO 10
<211> LENGTH: 8
```

```
<212> TYPE: PRT
<213> ORGANISM: Homo sapiens

<400> SEQUENCE: 10

Arg Ala Ser Gln Ser Ile Ser Asn
1               5

<210> SEQ ID NO 11
<211> LENGTH: 7
<212> TYPE: PRT
<213> ORGANISM: Homo sapiens

<400> SEQUENCE: 11

Ala Ala Ser Arg Leu Gln Arg
1               5

<210> SEQ ID NO 12
<211> LENGTH: 9
<212> TYPE: PRT
<213> ORGANISM: Homo sapiens

<400> SEQUENCE: 12

Gln Gln Ser Tyr Ser Thr Asn Pro Thr
1               5

<210> SEQ ID NO 13
<211> LENGTH: 14
<212> TYPE: PRT
<213> ORGANISM: Homo sapiens

<400> SEQUENCE: 13

Thr Gly Ser Ser Ser Asn Ile Gly Ala Gly Tyr Asp Val His
1               5                   10

<210> SEQ ID NO 14
<211> LENGTH: 7
<212> TYPE: PRT
<213> ORGANISM: Homo sapiens

<400> SEQUENCE: 14

Gly Asn Asn Asn Arg Pro Ser
1               5

<210> SEQ ID NO 15
<211> LENGTH: 11
<212> TYPE: PRT
<213> ORGANISM: Homo sapiens

<400> SEQUENCE: 15

Gln Ser Tyr Asp Ser Ser Leu Ser Gly Phe Glu
1               5                   10

<210> SEQ ID NO 16
<211> LENGTH: 128
<212> TYPE: PRT
<213> ORGANISM: Homo sapiens

<400> SEQUENCE: 16

Met Ala Gln Val Gln Leu Val Gln Ser Gly Ala Glu Val Lys Lys Pro
1               5                   10                  15

Gly Ser Ser Val Lys Val Ser Cys Lys Ala Ser Gly Gly Thr Tyr Ile
                20                  25                  30

Asp Gln Pro Ile Gly Trp Val Arg Gln Ala Pro Gly Gln Gly Leu Glu
            35                  40                  45
```

Trp Met Gly Gly Ile Ile Pro Leu Ser Gly Pro His Tyr Ala Gln
            50                  55                  60

Lys Phe Gln Gly Lys Val Ser Ile Thr Ala Asp Glu Ser Thr Ser Thr
65                  70                  75                  80

Ala Tyr Leu Glu Leu Thr Ser Leu Thr Ser Glu Asp Thr Ala Val Tyr
                85                  90                  95

Tyr Cys Ala Arg Val Leu Arg Gly Tyr Cys Arg Arg Gly Ser Cys Tyr
                100                 105                 110

Asp Trp Leu Asp Pro Trp Gly Gln Gly Thr Leu Val Thr Val Ser Ser
            115                 120                 125

<210> SEQ ID NO 17
<211> LENGTH: 111
<212> TYPE: PRT
<213> ORGANISM: Homo sapiens

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Leu
            35                  40                  45

Tyr Ala Thr Ser Arg Leu Tyr Ser Gly Val Pro Ser Arg Phe Ser Gly
        50                  55                  60

Ser Gly Ser Gly Thr Asp Phe Thr Leu Ser Ile Ser Ser Leu Gln Pro
65                  70                  75                  80

Glu Asp Phe Ala Thr Tyr Tyr Cys Gln Gln Thr Lys Ser Phe Pro Leu
                85                  90                  95

Thr Phe Gly Gly Gly Thr Lys Val Glu Ile Lys Arg Ala Ala Ala
                100                 105                 110

<210> SEQ ID NO 18
<211> LENGTH: 111
<212> TYPE: PRT
<213> ORGANISM: Homo sapiens

<400> SEQUENCE: 18

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Thr Trp
                20                  25                  30

Leu Ala Trp Tyr Gln Gln Lys Pro Gly Arg Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ser Tyr Pro Phe
                85                  90                  95

Ser Phe Gly Pro Gly Thr Lys Val Glu Ile Lys Arg Ala Ala Ala
                100                 105                 110

<210> SEQ ID NO 19
<211> LENGTH: 111
<212> TYPE: PRT
<213> ORGANISM: Homo sapiens

<400> SEQUENCE: 19

Asp Ile Val Met Thr Gln Ser Pro Ser Ser Leu Ser Ala Ser Val Gly
1               5                   10                  15

Asp Thr Val Thr Ile Ser Cys Arg Ala Ser Gln Ser Ile Ser Asn Phe
            20                  25                  30

Leu Asn Trp Tyr Arg Gln Lys Pro Gly Lys Ala Pro Glu Leu Met Ile
        35                  40                  45

Tyr Ala Ala Ser Arg Leu Gln Arg Gly Asp Pro Ser Arg Phe Ser Gly
    50                  55                  60

Ser Gly Ser Gly Thr Glu Phe Ser Leu Thr Ile Ser Gly Leu Gln Pro
65                  70                  75                  80

Glu Asp Ser Ala Thr Tyr His Cys Gln Gln Ser Tyr Ser Thr Asn Pro
                85                  90                  95

Thr Phe Gly Gly Gly Thr Lys Val Glu Ile Lys Arg Ala Ala Ala
            100                 105                 110

<210> SEQ ID NO 20
<211> LENGTH: 116
<212> TYPE: PRT
<213> ORGANISM: Homo sapiens

<400> SEQUENCE: 20

Gln Ala Val Leu Thr Gln Pro Ser Ser Val Ser Gly Pro Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Phe Glu Val Phe Gly Thr Gly Thr Lys Val Glu Ile Lys
            100                 105                 110

Arg Ala Ala Ala
        115

<210> SEQ ID NO 21
<211> LENGTH: 384
<212> TYPE: DNA
<213> ORGANISM: Homo sapiens

<400> SEQUENCE: 21
atggcccagg tgcagctggt gcagtctggg gctgaggtga agaagcctgg gtcctcggtg      60
aaggtctcct gcaaggcttc tggaggcacc tacatcgacc aacctatcgg ctgggtgcga     120
caggcccctg gacaagggct tgagtggatg ggagggatca tccctctctc tggtccgcca     180
cactacgcac agaagttcca gggcaaagtc tcgattaccg cggacgagtc cacgagcaca     240
gcttacctgg aactgaccag cctcacatct gaggacacgg ccgtatatta ctgtgcgagg     300
gtccttaggg gttattgtcg tcgtggttcc tgctatgact ggctcgaccc ctggggccag     360
ggcaccctgg tcaccgtctc gagt                                            384

<210> SEQ ID NO 22
<211> LENGTH: 333
<212> TYPE: DNA
<213> ORGANISM: Homo sapiens

<400> SEQUENCE: 22

| | | | | | |
|---|---|---|---|---|---|
| gacatccaga | tgacccagtc | tccatcctcc | ctgtctgcat | ctgtaggaga | cagagtcacc | 60 |
| atcacttgcc | aggcgagtca | ggacattagc | aactatttaa | attggtatca | gcagaaacca | 120 |
| gggaaagccc | ctaagctcct | gctctatgct | acatccagat | tgtacagtgg | ggtcccatcc | 180 |
| aggttcagtg | gcagtggatc | tgggacagat | ttcactctca | gcatcagcag | cctgcagcct | 240 |
| gaagattttg | caacttacta | ttgtcaacag | actaagagtt | tcccccctca | c tttcggcggg | 300 |
| gggaccaagg | tggaaatcaa | acgtgcggcc | gca | | | 333 |

<210> SEQ ID NO 23
<211> LENGTH: 333
<212> TYPE: DNA
<213> ORGANISM: Homo sapiens

<400> SEQUENCE: 23

| | | | | | |
|---|---|---|---|---|---|
| gacatccaga | tgacccagtc | tccatcttcc | gtgtctgctt | ctgtagggga | cagagtcacc | 60 |
| atcacttgtc | gggcgagtca | ggatattagc | acctggttag | cctggtatca | gcagaaacca | 120 |
| gggagagccc | ctaagctcct | gatctatgct | gcatccagtt | tgcaaagtgg | ggtcccatca | 180 |
| aggttcagcg | gcagtgggtc | tgggacagaa | ttcactctca | caatcagcag | cctgcagcct | 240 |
| gaagattttg | caacttatta | ctgtctacag | catgatagtt | accccttctc | tttcggccct | 300 |
| gggaccaagg | tggaaatcaa | acgtgcggcc | gca | | | 333 |

<210> SEQ ID NO 24
<211> LENGTH: 333
<212> TYPE: DNA
<213> ORGANISM: Homo sapiens

<400> SEQUENCE: 24

| | | | | | |
|---|---|---|---|---|---|
| gacatcgtga | tgacccagtc | tccatcctcc | ctgtctgcat | ctgtaggaga | cacagtcacc | 60 |
| atctcttgcc | gggcaagtca | gagcattttc | aacttttttaa | actggtatcg | gcagaaacca | 120 |
| ggaaaggccc | ctgaactgat | gatttatgct | gcgtccagac | tgcaacgtgg | ggacccatca | 180 |
| aggtttagtg | gcagtggatc | tgggacagaa | ttcagtctca | ccatcagcgg | tctgcagcct | 240 |
| gaggattctg | caacctatca | ctgtcaacag | agttacagta | ccaatcccac | gttcggcggg | 300 |
| gggaccaagg | tggagatcaa | acgtgcggcc | gca | | | 333 |

<210> SEQ ID NO 25
<211> LENGTH: 348
<212> TYPE: DNA
<213> ORGANISM: Homo sapiens

<400> SEQUENCE: 25

| | | | | | |
|---|---|---|---|---|---|
| caggctgtgc | tcactcagcc | gtcctcagtg | tctgggcccc | cagggcagag | ggtcaccatc | 60 |
| tcctgcactg | ggagcagctc | caacatcggg | gcaggttatg | atgtacactg | gtaccagcag | 120 |
| cttccaggaa | cagcccccaa | actcctcatc | tatggtaaca | acaatcggcc | ctcagggGTC | 180 |
| cctgaccgat | tctctggctc | caagtctggc | acctcagcct | ccctggccat | cactgggctc | 240 |
| caggctgagg | atgaggctga | ttattactgc | cagtcctatg | acagcagcct | gagtgggttt | 300 |
| gaggtcttcg | gaaccgggac | caaggtggag | atcaaacgtg | cggccgca | | 348 |

<210> SEQ ID NO 26
<211> LENGTH: 900
<212> TYPE: DNA
<213> ORGANISM: Homo sapiens

<400> SEQUENCE: 26

| | | | | | |
|---|---|---|---|---|---|
| gtgaaaaaat | tattattcgc | aattccttta | gttgttcctt | tctatgcggc | ccagccggcc | 60 |
| atggcccagg | tgcagctggt | gcagtctggg | gctgaggtga | agaagcctgg | gtcctcggtg | 120 |
| aaggtctcct | gcaaggcttc | tggaggcacc | tacatcgacc | aacctatcgg | ctgggtgcga | 180 |
| caggcccctg | gacaagggct | tgagtggatg | ggagggatca | tccctctctc | tggtccgcca | 240 |
| cactacgcac | agaagttcca | gggcaaagtc | tcgattaccg | cggacgagtc | cacgagcaca | 300 |
| gcttacctgg | aactgaccag | cctcacatct | gaggacacgg | ccgtatatta | ctgtgcgagg | 360 |
| gtccttaggg | gttattgtcg | tcgtggttcc | tgctatgact | ggctcgaccc | ctggggccag | 420 |
| ggcaccctg | tcaccgtctc | gagtggaggc | ggcggttcag | gcggaggtgg | ctctggcggt | 480 |
| ggcggaagtg | cacttgacat | ccagatgacc | cagtctccat | cctccctgtc | tgcatctgta | 540 |
| ggagacagag | tcaccatcac | ttgccaggcg | agtcaggaca | ttagcaacta | tttaaattgg | 600 |
| tatcagcaga | aaccagggaa | agcccctaag | ctcctgctct | atgctacatc | cagattgtac | 660 |
| agtggggtcc | catccaggtt | cagtggcagt | ggatctggga | cagatttcac | tctcagcatc | 720 |
| agcagcctgc | agcctgaaga | ttttgcaact | tactattgtc | aacagactaa | gagtttcccc | 780 |
| ctcactttcg | gcggggggac | caaggtggaa | atcaaacgtg | cggccgcaga | gcagaagctg | 840 |
| atcagcgaag | aggatctggg | ctcgaggtcg | acccaccatg | cgcatcacca | cgccgcatag | 900 |

<210> SEQ ID NO 27
<211> LENGTH: 900
<212> TYPE: DNA
<213> ORGANISM: Homo sapiens

<400> SEQUENCE: 27

| | | | | | |
|---|---|---|---|---|---|
| gtgaaaaaat | tattattcgc | aattccttta | gttgttcctt | tctatgcggc | ccagccggcc | 60 |
| atggcccagg | tgcagctggt | gcagtctggg | gctgaggtga | agaagcctgg | gtcctcggtg | 120 |
| aaggtctcct | gcaaggcttc | tggaggcacc | tacatcgacc | aacctatcgg | ctgggtgcga | 180 |
| caggcccctg | gacaagggct | tgagtggatg | ggagggatca | tccctctctc | tggtccgcca | 240 |
| cactacgcac | agaagttcca | gggcaaagtc | tcgattaccg | cggacgagtc | cacgagcaca | 300 |
| gcttacctgg | aactgaccag | cctcacatct | gaggacacgg | ccgtatatta | ctgtgcgagg | 360 |
| gtccttaggg | gttattgtcg | tcgtggttcc | tgctatgact | ggctcgaccc | ctggggccag | 420 |
| ggcaccctg | tcaccgtctc | gagtggaggc | ggcggttcag | gcggaggtgg | ctctggcggt | 480 |
| ggcggaagtg | cacttgacat | ccagatgacc | cagtctccat | cttccgtgtc | tgcttctgta | 540 |
| ggggacagag | tcaccatcac | ttgtcgggcg | agtcaggata | ttagcacctg | gttagcctgg | 600 |
| tatcagcaga | aaccagggag | agcccctaag | ctcctgatct | atgctgcatc | cagtttgcaa | 660 |
| agtggggtcc | catcaaggtt | cagcggcagt | gggtctggga | cagaattcac | tctcacaatc | 720 |
| agcagcctgc | agcctgaaga | ttttgcaact | tattactgtc | tacagcatga | tagttacccc | 780 |
| ttctctttcg | gccctgggac | caaggtggaa | atcaaacgtg | cggccgcaga | gcagaagctg | 840 |
| atcagcgaag | aggatctggg | ctcgaggtcg | acccaccatg | cgcatcacca | cgccgcatag | 900 |

<210> SEQ ID NO 28
<211> LENGTH: 900

<212> TYPE: DNA
<213> ORGANISM: Homo sapiens

<400> SEQUENCE: 28

```
gtgaaaaaat tattattcgc aattccttta gttgttcctt tctatgcggc ccagccggcc    60
atggcccagg tgcagctggt gcagtctggg gctgaggtga agaagcctgg gtcctcggtg   120
aaggtctcct gcaaggcttc tggaggcacc tacatcgacc aacctatcgg ctgggtgcga   180
caggcccctg gacaagggct tgagtggatg ggagggatca tccctctctc tggtccgcca   240
cactacgcac agaagttcca gggcaaagtc tcgattaccg cggacgagtc cacgagcaca   300
gcttacctgg aactgaccag cctcacatct gaggacacgg ccgtatatta ctgtgcgagg   360
gtccttaggg gttattgtcg tcgtggttcc tgctatgact ggctcgaccc ctggggccag   420
ggcaccctgg tcaccgtctc gagtggaggc ggcggttcag gcggaggtgg ctctggcggt   480
ggcggaagtg cacttgacat cgtgatgacc cagtctccat cctccctgtc tgcatctgta   540
ggagacacag tcaccatctc ttgccgggca agtcagagca tttccaactt tttaaactgg   600
tatcggcaga aaccaggaaa ggcccctgaa ctgatgattt atgctgcgtc cagactgcaa   660
cgtggggacc catcaaggtt tagtggcagt ggatctggga cagaattcag tctcaccatc   720
agcggtctgc agcctgagga ttctgcaacc tatcactgtc aacagagtta cagtaccaat   780
cccacgttcg gcgggggac caaggtggag atcaaacgtg cggccgcaga gcagaagctg   840
atcagcgaag aggatctggg ctcgaggtcg acccaccatg cgcatcacca cgccgcatag   900
```

<210> SEQ ID NO 29
<211> LENGTH: 915
<212> TYPE: DNA
<213> ORGANISM: Homo sapiens

<400> SEQUENCE: 29

```
gtgaaaaaat tattattcgc aattccttta gttgttcctt tctatgcggc ccagccggcc    60
atggcccagg tgcagctggt gcagtctggg gctgaggtga agaagcctgg gtcctcggtg   120
aaggtctcct gcaaggcttc tggaggcacc tacatcgacc aacctatcgg ctgggtgcga   180
caggcccctg gacaagggct tgagtggatg ggagggatca tccctctctc tggtccgcca   240
cactacgcac agaagttcca gggcaaagtc tcgattaccg cggacgagtc cacgagcaca   300
gcttacctgg aactgaccag cctcacatct gaggacacgg ccgtatatta ctgtgcgagg   360
gtccttaggg gttattgtcg tcgtggttcc tgctatgact ggctcgaccc ctggggccag   420
ggcaccctgg tcaccgtctc gagtggaggc ggcggttcag gcggaggtgg ctctggcggt   480
ggcggaagtg cacttcaggc tgtgctcact cagccgtcct cagtgtctgg ccccccaggg   540
cagagggtca ccatctcctg cactgggagc agctccaaca tcggggcagg ttatgatgta   600
cactggtacc agcagcttcc aggaacagcc cccaaactcc tcatctatgg taacaacaat   660
cggccctcag gggtccctga ccgattctct ggctccaagt ctggcacctc agcctccctg   720
gccatcactg gctccaggc tgaggatgag gctgattatt actgccagtc ctatgacagc   780
agcctgagtg ggtttgaggt cttcggaacc gggaccaagg tggagatcaa acgtgcggcc   840
gcagagcaga agctgatcag cgaagaggat ctgggctcga ggtcgaccca ccatgcgcat   900
caccacgccg catag                                                     915
```

<210> SEQ ID NO 30
<211> LENGTH: 110
<212> TYPE: DNA

<210> SEQ ID NO 30
<211> LENGTH: 110
<212> TYPE: DNA
<213> ORGANISM: Artificial
<220> FEATURE:
<223> OTHER INFORMATION: PCR Primer

<400> SEQUENCE: 30
cccaagctta ccatggatgc aatgaagaga gggctctgct gtgtgctgct gctgtgtgga      60
gcagtcttcg tttcggctag ccatacccgc gtgacggggg gggtgcaagg               110

<210> SEQ ID NO 31
<211> LENGTH: 82
<212> TYPE: DNA
<213> ORGANISM: Artificial
<220> FEATURE:
<223> OTHER INFORMATION: PCR Primer

<400> SEQUENCE: 31 cccctcgag tctagattaa cgcggttcca gcggatccgg atacggcacc ggcgcaccgg      60
agacgaccgc cgaccctata cc                                             82

<210> SEQ ID NO 32
<211> LENGTH: 26
<212> TYPE: DNA
<213> ORGANISM: Artificial
<220> FEATURE:
<223> OTHER INFORMATION: PCR Primer

<400> SEQUENCE: 32
gcgccgccat gggagtggag ggctgc                                          26

<210> SEQ ID NO 33
<211> LENGTH: 24
<212> TYPE: DNA
<213> ORGANISM: Artificial
<220> FEATURE:
<223> OTHER INFORMATION: PCR Primer

<400> SEQUENCE: 33
ctcagtacac ggagctgttc cgga                                            24

<210> SEQ ID NO 34
<211> LENGTH: 127
<212> TYPE: PRT
<213> ORGANISM: Homo sapiens

<400> SEQUENCE: 34

Met Ala Glu Val Gln Leu Val Glu Ser Gly Ala Glu Val Lys Lys Pro
1               5                   10                  15

Gly Ser Ser Val Lys Val Ser Cys Lys Ala Ser Gly Gly Thr Tyr Ile
            20                  25                  30

Asp Gln Pro Ile Gly Trp Val Arg Gln Ala Pro Gly Gln Gly Leu Glu
        35                  40                  45

Trp Met Gly Gly Ile Ile Pro Leu Ser Gly Pro Pro His Tyr Ala Gln
    50                  55                  60

Lys Phe Gln Gly Lys Val Ser Ile Thr Ala Asp Glu Ser Thr Ser Thr
65                  70                  75                  80

Ala Tyr Leu Glu Leu Thr Ser Leu Thr Ser Glu Asp Thr Ala Val Tyr
                85                  90                  95

Tyr Cys Ala Arg Val Leu Gly Thr Cys Arg Arg Gly Ser Cys Tyr Asp
            100                 105                 110

Trp Leu Asp Pro Trp Gly Gln Gly Thr Leu Val Thr Val Ser Ser
        115                 120                 125

<210> SEQ ID NO 35
<211> LENGTH: 384
<212> TYPE: DNA
<213> ORGANISM: Homo sapiens

<400> SEQUENCE: 35

| | | | | | |
|---|---|---|---|---|---|
| atggccgagg | tgcagctggt | ggagtctggg | gctgaggtga | agaagcctgg | gtcctcggtg | 60 |
| aaggtctcct | gcaaggcttc | tggaggcacc | tacatcgacc | aacctatcgg | ctgggtgcga | 120 |
| caggcccctg | gacaagggct | tgagtggatg | ggagggatca | tccctctctc | tggtccgcca | 180 |
| cactacgcac | agaagttcca | gggcaaagtc | tcgattaccg | cggacgagtc | cacgagcaca | 240 |
| gcttacctgg | aactgaccag | cctcacatct | gaggacacgg | ccgtatatta | ctgtgcgagg | 300 |
| gtccttaggg | gttattgtcg | tcgtggttcc | tgctatgact | ggctcgaccc | ctggggccag | 360 |
| ggcaccctgg | tcaccgtctc | gagt | | | | 384 |

<210> SEQ ID NO 36
<211> LENGTH: 900
<212> TYPE: DNA
<213> ORGANISM: Homo sapiens

<400> SEQUENCE: 36

| | | | | | |
|---|---|---|---|---|---|
| gtgaaaaaat | tattattcgc | aattcccttta | gttgttcctt | tctatgcggc | ccagccggcc | 60 |
| atggccgagg | tgcagctggt | ggagtctggg | gctgaggtga | agaagcctgg | gtcctcggtg | 120 |
| aaggtctcct | gcaaggcttc | tggaggcacc | tacatcgacc | aacctatcgg | ctgggtgcga | 180 |
| caggcccctg | gacaagggct | tgagtggatg | ggagggatca | tccctctctc | tggtccgcca | 240 |
| cactacgcac | agaagttcca | gggcaaagtc | tcgattaccg | cggacgagtc | cacgagcaca | 300 |
| gcttacctgg | aactgaccag | cctcacatct | gaggacacgg | ccgtatatta | ctgtgcgagg | 360 |
| gtccttaggg | gttattgtcg | tcgtggttcc | tgctatgact | ggctcgaccc | ctggggccag | 420 |
| ggcaccctgg | tcaccgtctc | gagtggaggc | ggcggttcag | gcggaggtgg | ctctggcggt | 480 |
| ggcggaagtg | cacttgacat | ccagatgacc | cagtctccat | cctccctgtc | tgcatctgta | 540 |
| ggagacagag | tcaccatcac | ttgccaggcg | agtcaggaca | ttagcaacta | tttaaattgg | 600 |
| tatcagcaga | aaccagggaa | agcccctaag | ctcctgctct | atgctacatc | cagattgtac | 660 |
| agtggggtcc | catccaggtt | cagtggcagt | ggatctggga | cagatttcac | tctcagcatc | 720 |
| agcagcctgc | agcctgaaga | ttttgcaact | tactattgtc | aacagactaa | gagttttccc | 780 |
| ctcactttcg | gcggggggac | caaggtggaa | atcaaacgtg | cggccgcaga | gcagaagctg | 840 |
| atcagcgaag | aggatctggg | ctcgaggtcg | acccaccatg | cgcatcacca | cgccgcatag | 900 |

<210> SEQ ID NO 37
<211> LENGTH: 900
<212> TYPE: DNA
<213> ORGANISM: Homo sapiens

<400> SEQUENCE: 37

| | | | | | |
|---|---|---|---|---|---|
| gtgaaaaaat | tattattcgc | aattcccttta | gttgttcctt | tctatgcggc | ccagccggcc | 60 |
| atggccgagg | tgcagctggt | ggagtctggg | gctgaggtga | agaagcctgg | gtcctcggtg | 120 |
| aaggtctcct | gcaaggcttc | tggaggcacc | tacatcgacc | aacctatcgg | ctgggtgcga | 180 |
| caggcccctg | gacaagggct | tgagtggatg | ggagggatca | tccctctctc | tggtccgcca | 240 |
| cactacgcac | agaagttcca | gggcaaagtc | tcgattaccg | cggacgagtc | cacgagcaca | 300 |

| | |
|---|---:|
| gcttacctgg aactgaccag cctcacatct gaggacacgg ccgtatatta ctgtgcgagg | 360 |
| gtccttaggg gttattgtcg tcgtggttcc tgctatgact ggctcgaccc ctggggccag | 420 |
| ggcaccctgg tcaccgtctc gagtggaggc ggcggttcag gcggaggtgg ctctggcggt | 480 |
| ggcggaagtg cacttgacat ccagatgacc cagtctccat cttccgtgtc tgcttctgta | 540 |
| ggggacagag tcaccatcac ttgtcgggcg agtcaggata ttagcacctg gttagcctgg | 600 |
| tatcagcaga aaccagggag agcccctaag ctcctgatct atgctgcatc cagtttgcaa | 660 |
| agtggggtcc catcaaggtt cagcggcagt gggtctggga cagaattcac tctcacaatc | 720 |
| agcagcctgc agcctgaaga ttttgcaact tattactgtc tacagcatga tagttacccc | 780 |
| ttctctttcg gccctgggac caaggtggaa atcaaacgtg cggccgcaga gcagaagctg | 840 |
| atcagcgaag aggatctggg ctcgaggtcg acccaccatg cgcatcacca cgccgcatag | 900 |

<210> SEQ ID NO 38
<211> LENGTH: 900
<212> TYPE: DNA
<213> ORGANISM: Homo sapiens
<400> SEQUENCE: 38

| | |
|---|---:|
| gtgaaaaaat tattattcgc aattcctttta gttgttcctt tctatgcggc ccagccggcc | 60 |
| atggccgagg tgcagctggt ggagtctggg gctgaggtga agaagcctgg gtcctcggtg | 120 |
| aaggtctcct gcaaggcttc tggaggcacc tacatcgacc aacctatcgg ctgggtgcga | 180 |
| caggcccctg gacaagggct tgagtggatg ggagggatca tccctctctc tggtccgcca | 240 |
| cactacgcac agaagttcca gggcaaagtc tcgattaccg cggacgagtc cacgagcaca | 300 |
| gcttacctgg aactgaccag cctcacatct gaggacacgg ccgtatatta ctgtgcgagg | 360 |
| gtccttaggg gttattgtcg tcgtggttcc tgctatgact ggctcgaccc ctggggccag | 420 |
| ggcaccctgg tcaccgtctc gagtggaggc ggcggttcag gcggaggtgg ctctggcggt | 480 |
| ggcggaagtg cacttgacat cgtgatgacc cagtctccat cctccctgtc tgcatctgta | 540 |
| ggagacacag tcaccatctc ttgccgggca agtcagagca tttccaactt tttaaactgg | 600 |
| tatcggcaga aaccaggaaa ggcccctgaa ctgatgattt atgctgcgtc cagactgcaa | 660 |
| cgtgggacc catcaaggtt tagtggcagt ggatctggga cagaattcag tctcaccatc | 720 |
| agcggtctgc agcctgagga ttctgcaacc tatcactgtc aacagagtta cagtaccaat | 780 |
| cccacgttcg gcgggggac caaggtggag atcaaacgtg cggccgcaga gcagaagctg | 840 |
| atcagcgaag aggatctggg ctcgaggtcg acccaccatg cgcatcacca cgccgcatag | 900 |

<210> SEQ ID NO 39
<211> LENGTH: 915
<212> TYPE: DNA
<213> ORGANISM: Homo sapiens
<400> SEQUENCE: 39

| | |
|---|---:|
| gtgaaaaaat tattattcgc aattcctttta gttgttcctt tctatgcggc ccagccggcc | 60 |
| atggccgagg tgcagctggt ggagtctggg gctgaggtga agaagcctgg gtcctcggtg | 120 |
| aaggtctcct gcaaggcttc tggaggcacc tacatcgacc aacctatcgg ctgggtgcga | 180 |
| caggcccctg gacaagggct tgagtggatg ggagggatca tccctctctc tggtccgcca | 240 |
| cactacgcac agaagttcca gggcaaagtc tcgattaccg cggacgagtc cacgagcaca | 300 |
| gcttacctgg aactgaccag cctcacatct gaggacacgg ccgtatatta ctgtgcgagg | 360 |
| gtccttaggg gttattgtcg tcgtggttcc tgctatgact ggctcgaccc ctggggccag | 420 |

-continued

```
ggcaccctgg tcaccgtctc gagtggaggc ggcggttcag gcggaggtgg ctctggcggt        480
ggcggaagtg cacttcaggc tgtgctcact cagccgtcct cagtgtctgg gcccccaggg        540
cagagggtca ccatctcctg cactgggagc agctccaaca tcggggcagg ttatgatgta        600
cactggtacc agcagcttcc aggaacagcc cccaaactcc tcatctatgg taacaacaat        660
cggccctcag gggtccctga ccgattctct ggctccaagt ctggcacctc agcctccctg        720
gccatcactg gctccaggc tgaggatgag gctgattatt actgccagtc ctatgacagc        780
agcctgagtg ggtttgaggt cttcggaacc gggaccaagg tggagatcaa acgtgcggcc        840
gcagagcaga agctgatcag cgaagaggat ctgggctcga ggtcgaccca ccatgcgcat        900
caccacgccg catag                                                        915

<210> SEQ ID NO 40
<211> LENGTH: 1428
<212> TYPE: DNA
<213> ORGANISM: Homo sapiens

<400> SEQUENCE: 40
atgaaacacc tgtggttctt cctcctgctg gtggcagctc ccagatgggt cctgtcccag         60
gtgcagctgg tgcagtctgg ggctgaggtg aagaagcctg gtcctcggt gaaggtctcc        120 tgcaaggctt ctggaggcac ctacatcgac caacctatcg ctgggtgcg acaggcccct        180 ggacaagggc ttgagtggat gggagggatc atccctctct ctggtccgcc acactacgca        240
cagaagttcc agggcaaagt ctcgattacc gcggacgagt ccacgagcac agcttacctg        300
gaactgacca gcctcacatc tgaggacacg gccgtatatt actgtgcgag gtccttagg        360 ggttattgtc gtcgtggttc ctgctatgac tggctcgacc cctggggcca gggcaccctg        420
gtcaccgtct cgagtgctag taccaagggc ccatccgtct tccccctggc accctcctcc        480
aagagcacct ctgggggcac agcggccctg gctgcctgg tcaaggacta cttccctgaa        540
ccggtgacgg tgtcgtggaa ctcaggcgcc ctgaccagcg gcgtgcacac cttcccggct        600
gtcctacagt cctcaggact ctactccctc agcagcgtgg tgaccgtgcc ctccagcagc        660
ttgggcaccc agacctacat ctgcaacgtg aatcacaagc ccagcaacac caaggtggac        720
aagaaagttg agcccaaatc ttgtgacaaa actcacacat gcccaccgtg cccagcacct        780
gaactcctgg ggggaccgtc agtcttcctc ttccccccaa aacccaagga caccctcatg        840
atctcccgga cccctgaggt cacatgcgtg gtggtggacg tgagccacga agaccctgag        900
gtcaagttca actggtacgt ggacggcgtg gaggtgcata atgccaagac aaagccgcgg        960
gaggagcagt acaacagcac gtaccgggtg gtcagcgtcc tcaccgtcct gcaccaggac       1020
tggctgaatg gcaaggagta caagtgcaag gtctccaaca agccctccc agccccatc        1080 gagaaaacca tctccaaagc caagggcag ccccgagaac cacaggtgta caccctgccc       1140
ccatcccggg atgagctgac caagaaccag gtcagcctga cctgcctggt caaaggcttc       1200
tatcccagcg acatcgccgt ggagtgggag agcaatgggc agccggagaa caactacaag       1260
accacgcctc ccgtgctgga ctccgacggc tccttcttcc tctacagcaa gctcaccgtg       1320
gacaagagca ggtggcagca ggggaacgtc ttctcatgct ccgtgatgca tgaggctctg       1380
cacaaccact acacgcagaa gagcctctcc ctgtctccgg gtaaatga                   1428

<210> SEQ ID NO 41
<211> LENGTH: 720
<212> TYPE: DNA
```

-continued

<213> ORGANISM: Homo sapiens

<400> SEQUENCE: 41

```
atggcgttgc agacccaggt cttcatttct ctgttgctct ggatctctgg tgcctacggg      60
gacatccaga tgacccagtc tccatcctcc ctgtctgcat ctgtaggaga cagagtcacc     120
atcacttgcc aggcgagtca ggacattagc aactatttaa attggtatca gcagaaacca     180
gggaaagccc ctaagctcct gctctatgct acatccagat tgtacagtgg ggtcccatcc     240
aggttcagtg gcagtggatc tgggacagat ttcactctca gcatcagcag cctgcagcct     300
gaagattttg caacttacta ttgtcaacag actaagagtt ccccctcac tttcggcggg      360
gggaccaagg tggaaatcaa acgtaccgtg gaaatcaaac gaactgtggc tgcaccatct     420
gtcttcatct cccgccatc tgatgagcag ttgaaatctg gaactgcctc tgttgtgtgc     480
ctgctgaata acttctatcc cagagaggcc aaagtacagt ggaaggtgga taacgccctc     540
caatcgggta actcccagga gagtgtcaca gagcaggaca gcaaggacag cacctacagc     600
ctcagcagca ccctgacgct gagcaaagca gactacgaga aacacaaagt ctacgcctgc     660
gaagtcaccc atcagggcct gagctcgccc gtcacaaaga gcttcaacag gggagagtgt     720
```

<210> SEQ ID NO 42
<211> LENGTH: 11
<212> TYPE: PRT
<213> ORGANISM: Homo sapiens

<400> SEQUENCE: 42

Arg Ala Asn Gln Asn Ile Gly Asn Phe Leu Asn
1               5                   10

<210> SEQ ID NO 43
<211> LENGTH: 7
<212> TYPE: PRT
<213> ORGANISM: Homo sapiens

<400> SEQUENCE: 43

Ala Ala Ser Asn Leu Gln Ser
1               5

<210> SEQ ID NO 44
<211> LENGTH: 9
<212> TYPE: PRT
<213> ORGANISM: Homo sapiens

<400> SEQUENCE: 44

Gln Gln Ser His Asn Ile Pro Leu Thr
1               5

<210> SEQ ID NO 45
<211> LENGTH: 11
<212> TYPE: PRT
<213> ORGANISM: Homo sapiens

<400> SEQUENCE: 45

Arg Ala Ser Gln Ser Ile Asn Asn Tyr Leu Asn
1               5                   10

<210> SEQ ID NO 46
<211> LENGTH: 7
<212> TYPE: PRT
<213> ORGANISM: Homo sapiens

<400> SEQUENCE: 46

Ala Ala Ser Ser Leu Gln Ser
1               5

<210> SEQ ID NO 47
<211> LENGTH: 10
<212> TYPE: PRT
<213> ORGANISM: Homo sapiens

<400> SEQUENCE: 47

Gln Gln Ser Tyr Asp Ser Thr Leu Phe Thr
1               5                   10

<210> SEQ ID NO 48
<211> LENGTH: 11
<212> TYPE: PRT
<213> ORGANISM: Homo sapiens

<400> SEQUENCE: 48

Arg Ala Ser Gln Ser Ile Ser Ser Tyr Leu Asn
1               5                   10

<210> SEQ ID NO 49
<211> LENGTH: 7
<212> TYPE: PRT
<213> ORGANISM: Homo sapiens

<400> SEQUENCE: 49

Ala Ala Ser Ser Leu Gln Ser
1               5

<210> SEQ ID NO 50
<211> LENGTH: 9
<212> TYPE: PRT
<213> ORGANISM: Homo sapiens

<400> SEQUENCE: 50

Gln Gln Ser Tyr Ser Thr Pro Leu Thr
1               5

<210> SEQ ID NO 51
<211> LENGTH: 11
<212> TYPE: PRT
<213> ORGANISM: Homo sapiens

<400> SEQUENCE: 51

Arg Ala Ser Gln Arg Ile Ser Asn Tyr Leu Asn
1               5                   10

<210> SEQ ID NO 52
<211> LENGTH: 7
<212> TYPE: PRT
<213> ORGANISM: Homo sapiens

<400> SEQUENCE: 52

Ala Ala Ser Asn Leu Gln Ser
1               5

<210> SEQ ID NO 53
<211> LENGTH: 9
<212> TYPE: PRT
<213> ORGANISM: Homo sapiens

<400> SEQUENCE: 53

Gln Gln Ser Tyr Thr Ile Pro Tyr Thr

<210> SEQ ID NO 54
<211> LENGTH: 111
<212> TYPE: PRT
<213> ORGANISM: Homo sapiens

<400> SEQUENCE: 54

Asp Val Val Met Thr Gln Ser Pro Ser Ser Leu Ser Ala Ser Val Gly
1               5                   10                  15

Asp Arg Val Thr Ile Thr Cys Arg Ala Asn Gln Asn Ile Gly Asn Phe
            20                  25                  30

Leu Asn Trp Tyr Gln Gln Lys Pro Gly Lys Ala Pro Lys Pro Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln Gln Ser His Asn Ile Pro Leu
                85                  90                  95

Thr Phe Gly Gly Gly Thr Lys Val Glu Ile Lys Arg Ala Ala Ala
            100                 105                 110

<210> SEQ ID NO 55
<211> LENGTH: 112
<212> TYPE: PRT
<213> ORGANISM: Homo sapiens

<400> SEQUENCE: 55

Asp Ile Gln Met Thr Gln Ser Pro Ser Ser Leu Ser Ala Ser Val Gly
1               5                   10                  15

Asp Arg Val Thr Met Thr Cys Arg Ala Ser Gln Ser Ile Asn Asn Tyr
            20                  25                  30

Leu Asn Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ser Tyr Asp Ser Thr Leu
                85                  90                  95

Phe Thr Phe Gly Pro Gly Thr Lys Val Glu Ile Lys Arg Ala Ala Ala
            100                 105                 110

<210> SEQ ID NO 56
<211> LENGTH: 111
<212> TYPE: PRT
<213> ORGANISM: Homo sapiens

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys Arg Ala Ala Ala
            100                 105                 110
```

<210> SEQ ID NO 57
<211> LENGTH: 111
<212> TYPE: PRT
<213> ORGANISM: Homo sapiens

<400> SEQUENCE: 57

```
Asp Ile Val Met Thr Gln Ser Pro Ser Ser Leu Ser Ala Ser Val Gly
 1               5                  10                  15

Asp Arg Val Thr Ile Thr Cys Arg Ala Ser Gln Arg Ile Ser Asn Tyr
             20                  25                  30

Leu Asn Trp Tyr Gln Gln Lys Pro Gly Lys Ala Pro Lys Leu Leu Val
         35                  40                  45

Tyr Ala Ala Ser Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Thr Ile Pro Tyr
                 85                  90                  95

Thr Phe Gly Gln Gly Thr Lys Leu Glu Ile Lys Arg Ala Ala Ala
            100                 105                 110
```

<210> SEQ ID NO 58
<211> LENGTH: 333
<212> TYPE: DNA
<213> ORGANISM: Homo sapiens

<400> SEQUENCE: 58

```
gatgttgtga tgactcagtc tccatcctcc ctgtctgcat ctgtagggga cagagtcacc      60
atcacttgcc gggcaaatca gaacattggt aattttttaa attggtatca gcagaaacca     120
gggaaagccc ctaagcccct gatctatgct gcatccaatt tgcaaagtgg ggtcccatca     180
aggttcagtg gcagtggatc tgggacagat ttcagtctca ccatcagcag tctgcaacct     240
gaagattttg caacttatta ctgtcaacag agtcacaata tcccgctcac tttcggcgga     300
gggaccaagg tggagatcaa acgtgcggcc gca                                  333
```

<210> SEQ ID NO 59
<211> LENGTH: 336
<212> TYPE: DNA
<213> ORGANISM: Homo sapiens

<400> SEQUENCE: 59

```
gacatccaga tgacccagtc tccatcttcc ctgtctgcat ctgtaggaga cagagtcacc      60
atgacttgcc gggcaagtca gagtattaac aactatttaa attggtatca acaaaaacca     120
gggaaagccc ctaagctcct gatctctgct gcatccagtt tgcaaagtgg ggtcccatcg     180
aggttcagtg gcagtggatc tgggacagat ttcactctca ccatcaccag tctgcaacct     240
gaggattttg caacttacta ctgtcaacag agttacgatt ccaccctatt cactttcggc     300
cctgggacca aggtggaaat caaacgtgcg gccgca                               336
```

<210> SEQ ID NO 60
<211> LENGTH: 333
<212> TYPE: DNA
<213> ORGANISM: Homo sapiens

<400> SEQUENCE: 60

| | | | | | |
|---|---|---|---|---|---|
| gacatccaga | tgacccagtc | tccatcctcc | ctgtctgcat | ctgtaggaga | cagagtcacc | 60 |
| atcacttgcc | gggcaagtca | gagcattagc | agctatttaa | attggtatca | gcagaaacca | 120 |
| gggaaagccc | ctaagctcct | gatctatgct | gcatccagtt | tgcaaagtgg | ggtcccatca | 180 |
| aggttcagtg | gcagtggatc | tgggacagat | ttcactctca | ccatcagcag | tctgcaacct | 240 |
| gaagattttg | caacttacta | ctgtcaacag | agttacagta | ccccgctcac | tttcggcgga | 300 |
| gggaccaagg | tggagatcaa | acgtgcggcc | gca | | | 333 |

<210> SEQ ID NO 61
<211> LENGTH: 333
<212> TYPE: DNA
<213> ORGANISM: Homo sapiens

<400> SEQUENCE: 61

| | | | | | |
|---|---|---|---|---|---|
| gacatcgtga | tgacccagtc | tccatcctcc | ctgtctgcat | ctgtaggaga | cagagtcacc | 60 |
| atcacttgcc | gggcaagtca | gcgcattagc | aactatttaa | attggtatca | gcagaaacca | 120 |
| gggaaagccc | ctaagctcct | ggtctatgct | gcatctaatt | tgcaaagtgg | ggtcccatca | 180 |
| aggttcagtg | gcagtggatc | tgggacagat | ttcactctca | ccatcagcag | tctgcaacct | 240 |
| gaagattttg | caacttacta | ctgtcaacag | agttacacta | ttccgtacac | ttttggccag | 300 |
| gggaccaagc | tggagatcaa | acgtgcggcc | gca | | | 333 |

<210> SEQ ID NO 62
<211> LENGTH: 900
<212> TYPE: DNA
<213> ORGANISM: Homo sapiens

<400> SEQUENCE: 62

| | | | | | |
|---|---|---|---|---|---|
| gtgaaaaaat | tattattcgc | aattccttta | gttgttcctt | tctatgcggc | ccagccggcc | 60 |
| atggccgagg | tgcagctggt | ggagtctggg | gctgaggtga | agaagcctgg | gtcctcggtg | 120 |
| aaggtctcct | gcaaggcttc | tggaggcacc | tacatcgacc | aacctatcgg | ctgggtgcga | 180 |
| caggcccctg | gacaagggct | tgagtggatg | ggagggatca | tccctctctc | tggtccgcca | 240 |
| cactacgcac | agaagttcca | gggcaaagtc | tcgattaccg | cggacgagtc | cacgagcaca | 300 |
| gcttacctgg | aactgaccag | cctcacatct | gaggacacgg | ccgtatatta | ctgtgcgagg | 360 |
| gtccttaggg | gttattgtcg | tcgtggttcc | tgctatgact | ggctcgaccc | ctggggccag | 420 |
| ggcaccctgg | tcaccgtctc | gagtggaggc | ggcggttcag | cggaggtgg | ctctggcggt | 480 |
| ggcggaagtg | cacttgatgt | tgtgatgact | cagtctccat | cctccctgtc | tgcatctgta | 540 |
| ggggacagag | tcaccatcac | ttgccgggca | atcagaaca | ttggtaattt | tttaaattgg | 600 |
| tatcagcaga | aaccagggaa | agcccctaag | cccctgatct | atgctgcatc | caatttgcaa | 660 |
| agtggggtcc | catcaaggtt | cagtggcagt | ggatctggga | cagatttcag | tctcaccatc | 720 |
| agcagtctgc | aacctgaaga | ttttgcaact | tattactgtc | aacagagtca | caatatcccg | 780 |
| ctcactttcg | gcggagggac | caaggtggag | atcaaacgtg | cggccgcaga | gcagaagctg | 840 |
| atcagcgaag | aggatctggg | ctcgaggtcg | acccaccatg | cgcatcacca | cgccgcatag | 900 |

<210> SEQ ID NO 63
<211> LENGTH: 903
<212> TYPE: DNA
<213> ORGANISM: Homo sapiens

<400> SEQUENCE: 63

| | | | | | |
|---|---|---|---|---|---|
| gtgaaaaaat | tattattcgc | aattccttta | gttgttcctt | tctatgcggc | ccagccggcc | 60 |
| atggccgagg | tgcagctggt | ggagtctggg | gctgaggtga | agaagcctgg | gtcctcggtg | 120 |
| aaggtctcct | gcaaggcttc | tggaggcacc | tacatcgacc | aacctatcgg | ctgggtgcga | 180 |
| caggcccctg | gacaagggct | tgagtggatg | ggagggatca | tccctctctc | tggtccgcca | 240 |
| cactacgcac | agaagttcca | gggcaaagtc | tcgattaccg | cggacgagtc | cacgagcaca | 300 |
| gcttacctgg | aactgaccag | cctcacatct | gaggacacgg | ccgtatatta | ctgtgcgagg | 360 |
| gtccttaggg | gttattgtcg | tcgtggttcc | tgctatgact | ggctcgaccc | ctggggccag | 420 |
| ggcaccctgg | tcaccgtctc | gagtggaggc | ggcggttcag | gcggaggtgg | ctctggcggt | 480 |
| ggcggaagtg | cacttgacat | ccagatgacc | cagtctccat | cttccctgtc | tgcatctgta | 540 |
| ggagacagag | tcaccatgac | ttgccgggca | agtcagagta | ttaacaacta | tttaaattgg | 600 |
| tatcaacaaa | aaccagggaa | agcccctaag | ctcctgatct | ctgctgcatc | cagtttgcaa | 660 |
| agtggggtcc | catcgaggtt | cagtggcagt | ggatctggga | cagatttcac | tctcaccatc | 720 |
| accagtctgc | aacctgagga | ttttgcaact | tactactgtc | aacagagtta | cgattccacc | 780 |
| ctattcactt | tcggccctgg | gaccaaggtg | gaaatcaaac | gtgcggccgc | agagcagaag | 840 |
| ctgatcagcg | aagaggatct | gggctcgagg | tcgacccacc | atgcgcatca | ccacgccgca | 900 |
| tag | | | | | | 903 |

<210> SEQ ID NO 64
<211> LENGTH: 900
<212> TYPE: DNA
<213> ORGANISM: Homo sapiens

<400> SEQUENCE: 64

| | | | | | |
|---|---|---|---|---|---|
| gtgaaaaaat | tattattcgc | aattccttta | gttgttcctt | tctatgcggc | ccagccggcc | 60 |
| atggccgagg | tgcagctggt | ggagtctggg | gctgaggtga | agaagcctgg | gtcctcggtg | 120 |
| aaggtctcct | gcaaggcttc | tggaggcacc | tacatcgacc | aacctatcgg | ctgggtgcga | 180 |
| caggcccctg | gacaagggct | tgagtggatg | ggagggatca | tccctctctc | tggtccgcca | 240 |
| cactacgcac | agaagttcca | gggcaaagtc | tcgattaccg | cggacgagtc | cacgagcaca | 300 |
| gcttacctgg | aactgaccag | cctcacatct | gaggacacgg | ccgtatatta | ctgtgcgagg | 360 |
| gtccttaggg | gttattgtcg | tcgtggttcc | tgctatgact | ggctcgaccc | ctggggccag | 420 |
| ggcaccctgg | tcaccgtctc | gagtggaggc | ggcggttcag | gcggaggtgg | ctctggcggt | 480 |
| ggcggaagtg | cacttgacat | ccagatgacc | cagtctccat | cctccctgtc | tgcatctgta | 540 |
| ggagacagag | tcaccatcac | ttgccgggca | agtcagagca | ttagcagcta | tttaaattgg | 600 |
| tatcagcaga | aaccagggaa | agcccctaag | ctcctgatct | atgctgcatc | cagtttgcaa | 660 |
| agtggggtcc | catcaaggtt | cagtggcagt | ggatctggga | cagatttcac | tctcaccatc | 720 |
| agcagtctgc | aacctgaaga | ttttgcaact | tactactgtc | aacagagtta | cagtaccccg | 780 |
| ctcactttcg | gcggagggac | caaggtggag | atcaaacgtg | cggccgcaga | gcagaagctg | 840 |
| atcagcgaag | aggatctggg | ctcgaggtcg | acccaccatg | cgcatcacca | cgccgcatag | 900 |

<210> SEQ ID NO 65

<211> LENGTH: 900
<212> TYPE: DNA
<213> ORGANISM: Homo sapiens

<400> SEQUENCE: 65
gtgaaaaaat tattattcgc aattcctttta gttgttcctt tctatgcggc ccagccggcc    60
atggccgagg tgcagctggt ggagtctggg gctgaggtga agaagcctgg gtcctcggtg   120
aaggtctcct gcaaggcttc tggaggcacc tacatcgacc aacctatcgg ctgggtgcga   180
caggcccctg gacaagggct tgagtggatg ggagggatca tccctctctc tggtccgcca   240
cactacgcac agaagttcca gggcaaagtc tcgattaccg cggacgagtc cacgagcaca   300
gcttacctgg aactgaccag cctcacatct gaggacacgg ccgtatatta ctgtgcgagg   360
gtccttaggg gttattgtcg tcgtggttcc tgctatgact ggctcgaccc ctggggccag   420
ggcaccctgg tcaccgtctc gagtggaggc ggcggttcag gcggaggtgg ctctggcggt   480
ggcggaagtg cacttgacat cgtgatgacc cagtctccat cctccctgtc tgcatctgta   540
ggagacagag tcaccatcac ttgccgggca agtcagcgca ttagcaacta tttaaattgg   600
tatcagcaga aaccagggaa agcccctaag ctcctggtct atgctgcatc taatttgcaa   660
agtggggtcc catcaaggtt cagtggcagt ggatctggga cagatttcac tctcaccatc   720
agcagtctgc aacctgaaga ttttgcaact tactactgtc aacagagtta cactattccg   780
tacacttttg gccaggggac caagctggag atcaaacgtg cggccgcaga gcagaagctg   840
atcagcgaag aggatctggg ctcgaggtcg acccaccatg cgcatcacca cgccgcatag   900

<210> SEQ ID NO 66
<211> LENGTH: 59
<212> TYPE: DNA
<213> ORGANISM: Artificial
<220> FEATURE:
<223> OTHER INFORMATION: PCR Primer

<400> SEQUENCE: 66
ccctgatcag aattcgcagg atccctcgag actagtgatg atcgggccag atatacgcg    59

<210> SEQ ID NO 67
<211> LENGTH: 51
<212> TYPE: DNA
<213> ORGANISM: Artificial
<220> FEATURE:
<223> OTHER INFORMATION: PCR Primer

<400> SEQUENCE: 67
ccctgatcaa gatctgctag cgtcgactcc ccagcatgcc tgctgctatt g    51

<210> SEQ ID NO 68
<211> LENGTH: 33
<212> TYPE: DNA
<213> ORGANISM: Artificial
<220> FEATURE:
<223> OTHER INFORMATION: PCR Primer

<400> SEQUENCE: 68
ccccagatct ctattccttt gccctcggac gag    33

<210> SEQ ID NO 69
<211> LENGTH: 34
<212> TYPE: DNA
<213> ORGANISM: Artificial
<220> FEATURE:
<223> OTHER INFORMATION: PCR Primer -continued

<400> SEQUENCE: 69
ccccaagctt atgaaaaagc ctgaactcac cgcg     34

<210> SEQ ID NO 70
<211> LENGTH: 26
<212> TYPE: DNA
<213> ORGANISM: Artificial
<220> FEATURE:
<223> OTHER INFORMATION: PCR Primer

<400> SEQUENCE: 70
cccgccggct gggtgtggcg gaccgc     26

<210> SEQ ID NO 71
<211> LENGTH: 29
<212> TYPE: DNA
<213> ORGANISM: Artificial
<220> FEATURE:
<223> OTHER INFORMATION: PCR Primer

<400> SEQUENCE: 71
cccctctaga aagtatagga acttcaagc     29

<210> SEQ ID NO 72
<211> LENGTH: 45
<212> TYPE: DNA
<213> ORGANISM: Artificial
<220> FEATURE:
<223> OTHER INFORMATION: PCR Primer

<400> SEQUENCE: 72
ccccaagctt ctcgagacta gtaccaaggg cccatcggtc ttccc     45

<210> SEQ ID NO 73
<211> LENGTH: 41
<212> TYPE: DNA
<213> ORGANISM: Artificial
<220> FEATURE:
<223> OTHER INFORMATION: PCR Primer

<400> SEQUENCE: 73
ccccgggccc tctagtagct ttcatttacc cggagacagg g     41

<210> SEQ ID NO 74
<211> LENGTH: 92
<212> TYPE: DNA
<213> ORGANISM: Artificial
<220> FEATURE:
<223> OTHER INFORMATION: PCR Primer

<400> SEQUENCE: 74
cccaagcttc accatgaaac acctgtggtt cttcctcctg ctggtggcag ctcccagatg     60
ggtcctgtcc caggtgcagc tggtgcagtc tg     92

<210> SEQ ID NO 75
<211> LENGTH: 33
<212> TYPE: DNA
<213> ORGANISM: Artificial
<220> FEATURE:
<223> OTHER INFORMATION: PCR Primer

<400> SEQUENCE: 75
cccgctagca ctcgagacgg tgaccagggt gcc     33

```
<210> SEQ ID NO 76
<211> LENGTH: 45
<212> TYPE: DNA
<213> ORGANISM: Artificial
<220> FEATURE:
<223> OTHER INFORMATION: PCR Primer

<400> SEQUENCE: 76
ccccagagct agtcctgcag gcggggaaat gtgcgcggaa cccct            45

<210> SEQ ID NO 77
<211> LENGTH: 39
<212> TYPE: DNA
<213> ORGANISM: Artificial
<220> FEATURE:
<223> OTHER INFORMATION: PCR Primer

<400> SEQUENCE: 77
ccccgctagc ctgcaagtca tttcgaaccc cagcgtccc                   39

<210> SEQ ID NO 78
<211> LENGTH: 49
<212> TYPE: DNA
<213> ORGANISM: Artificial
<220> FEATURE:
<223> OTHER INFORMATION: PCR Primer

<400> SEQUENCE: 78
ccccaagctt ctagagtcga cggtaccgtg gaaatcaaac gaactgtgg        49

<210> SEQ ID NO 79
<211> LENGTH: 45
<212> TYPE: DNA
<213> ORGANISM: Artificial
<220> FEATURE:
<223> OTHER INFORMATION: PCR Primer

<400> SEQUENCE: 79
ccccgggccc tctagcggcc gcctaacact ctcccctgtt gaagc            45

<210> SEQ ID NO 80
<211> LENGTH: 96
<212> TYPE: DNA
<213> ORGANISM: Artificial
<220> FEATURE:
<223> OTHER INFORMATION: PCR Primer

<400> SEQUENCE: 80
cccaagcttc accatggcgt tgcagaccca ggtcttcatt tctctgttgc tctggatctc    60
tggtgcctac ggggacatcc agatgaccca gtctcc                              96

<210> SEQ ID NO 81
<211> LENGTH: 34
<212> TYPE: DNA
<213> ORGANISM: Artificial
<220> FEATURE:
<223> OTHER INFORMATION: PCR Primer

<400> SEQUENCE: 81
ccccgtacgt ttgatttcca ccttggtccc cccg                        34
```